(12) United States Patent
Fleck et al.

(10) Patent No.: US 8,530,460 B2
(45) Date of Patent: Sep. 10, 2013

(54) AZETIDINE DERIVATIVES

(71) Applicants: Martin Fleck, Warthausen (DE); Bernd Nosse, Biberach an der Riss (DE); Niklas Heine, Biberach an der Riss (DE); Gerald Juergen Roth, Biberach an der Riss (DE)

(72) Inventors: Martin Fleck, Warthausen (DE); Bernd Nosse, Biberach an der Riss (DE); Niklas Heine, Biberach an der Riss (DE); Gerald Juergen Roth, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/714,511

(22) Filed: Dec. 14, 2012

(65) Prior Publication Data
US 2013/0158004 A1  Jun. 20, 2013

(30) Foreign Application Priority Data
Dec. 19, 2011 (EP) .................................. 11 94 277

(51) Int. Cl.
| A61K 31/397 | (2006.01) |
| A61K 31/44 | (2006.01) |
| A01N 43/54 | (2006.01) |
| A01N 43/76 | (2006.01) |
| A01N 43/78 | (2006.01) |
| C07D 205/02 | (2006.01) |
| C07D 263/34 | (2006.01) |
| C07D 277/02 | (2006.01) |
| C07D 213/72 | (2006.01) |
| C07D 239/02 | (2006.01) |
| C07D 311/04 | (2006.01) |

(52) U.S. Cl.
USPC .................. 514/210.01; 514/210.2; 514/275; 514/352; 514/371; 514/374; 544/330; 546/297; 548/185; 548/201; 548/236; 548/952; 549/404

(58) Field of Classification Search
None
See application file for complete search history.

(56) References Cited

U.S. PATENT DOCUMENTS
| 2008/0274947 A1 | 11/2008 | Jaehne et al. |
| 2009/0203663 A1* | 8/2009 | Arnould et al. .......... 514/210.01 |
| 2011/0263562 A1 | 10/2011 | Yamashita et al. |

FOREIGN PATENT DOCUMENTS
| WO | 03072197 A1 | 9/2003 |
| WO | 2007075629 A2 | 7/2007 |
| WO | 2007143823 A1 | 12/2007 |
| WO | 2010043052 A1 | 4/2010 |
| WO | 2010127212 A1 | 11/2010 |

OTHER PUBLICATIONS

Abstract in English for JP2006-131559, Date May 25, 2006.
Abstract in English for JP2008-179621, Date Aug. 7, 2008.
Abstract in English for JP2010-043019, Date Feb. 25, 2010.
International Search Report, Form PCT/ISR/210, and Written Opinion, Form PCT/ISA/237, for cooresponding application PCT/EP2012/075996, Date of mailing Jan. 31, 2013.

* cited by examiner

*Primary Examiner* — Jason M Nolan
*Assistant Examiner* — Po-Chih Chen
(74) *Attorney, Agent, or Firm* — Michael P. Morris; Alan R. Stempel

(57) ABSTRACT

Azetidine derivatives of which the following is exemplary

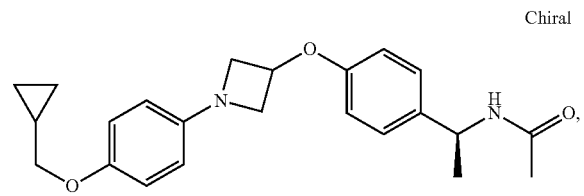

and their use in the treatment of obesity, diabetes or dyslipidemia.

11 Claims, No Drawings

AZETIDINE DERIVATIVES

FIELD OF THE INVENTION

This invention relates to new compounds, in particular azetidine derivatives, to processes for preparing such compounds, to their use as inhibitors of acetyl-CoA carboxylases, to methods for their therapeutic use, in particular in diseases and conditions mediated by the inhibition of acetyl-CoA carboxylase(s), and to pharmaceutical compositions comprising them.

BACKGROUND OF THE INVENTION

Obesity is major public health issues not only for the EU, USA, Japan but also for the world in general. It is associated with a number of serious diseases including diabetes, dyslipidemia, hypertension, cardiovascular and cerebrovascular diseases. Although the underlying mechanisms are not yet fully understood, the impairement of insulin action in target tissues by accumulation of excess lipids is generally regarded as a key mechanism linking obesity to secondary pathologies (G. Wolf, Nutrition Reviews Vol. 66(10):597-600; D B Savage, K F Petersen, G I Shulman, Physiol Rev. 2007; 87:507-520). Therefore, understanding of cellular lipid metabolism in insulin target tissues is crucial in order to elucidate the development of diseases associated with obesity.

A central event in lipid metabolism is the generation of malonyl-CoA via carboxylation of acetyl-CoA by the two mammalian ACC isoforms ACC1 (ACC-alpha, also termed ACCA) and ACC2 (ACC-beta, also designated ACCB) (Saggerson D. Annu Rev Nutr. 2008; 28:253-72). The malonyl-CoA generated is used for de novo fatty acid synthesis and acts as inhibitor of CPT-1, thereby regulating mitochondrial fatty acid oxidation. Furthermore, malonyl-CoA is also described to act centrally to control food intake, and may play an important role in controlling insulin secretion from the pancreas (G D Lopaschuk, J R Ussher, J S Jaswal. Pharmacol Rev. 2010; 62(2):237-64; D Saggerson Annu Rev Nutr. 2008; 28:253-72), further coordinating the regulation of intermediary metabolism.

Therefore ACC1 and ACC2 have been shown to be major regulators of fatty acid metabolism and are presently considered as an attractive target to regulate the human diseases of obesity, diabetes and cardiovascular complications (S J Wakil and L A Abu-Elheiga, J. Lipid Res. 2009. 50: S138-S143; L. Tong, H J Harwood Jr. Journal of Cellular Biochemistry 99:1476-1488, 2006).

As a result of its unique position in intermediary metabolism, inhibition of ACC offers the ability to inhibit de novo fatty acid production in lipogenic tissues (liver and adipose) while at the same time stimulating fatty acid oxidation in oxidative tissues (liver, heart, and skeletal muscle) and therefore offers an attractive modality for favorably affecting, in a concerted manner, a multitude of cardiovascular risk factors associated with obesity, diabetes, insulin resistance, and the metabolic syndrome (L. Tong, H J Harwood Jr. Journal of Cellular Biochemistry 99:1476-1488, 2006; Corbett J W, Harwood J H Jr., Recent Pat Cardiovasc Drug Discov. 2007 Nov.; 2(3):162-80). In addition ACC inhibitors also have the potential to intervene in the progression of diseases that result from the rapid growth of malignant cells or invading organisms that are dependent on endogenous lipid synthesis to sustain their rapid proliferation. The potential of ACC inhibitors as antifungal agents and as antibacterial agents is well documented (L. Tong, H J Harwood Jr. Journal of Cellular Biochemistry 99:1476-1488, 2006). Furthermore, de novo lipogenesis is known to be required for growth of many tumor cells and ACC up-regulation has been recognized in multiple human cancers, promoting lipogenesis to meet the need of cancer cells for rapid growth and proliferation (C Wang, S Rajput, K Watabe, D F Liao, D Cao Front Biosci 2010; 2:515-26). This is further demonstrated in studies using ACC inhibitors which induced growth arrest and selective cytotoxicity in cancer cells and by RNA interference-mediated knock-down of ACC which inhibited growth and induced apoptosis in different types of cancer cells. Furthermore, ACC1 associates with and is regulated by the breast cancer susceptibility gene 1 (BRCA1). Commonly occurring BRCA1 mutations lead to ACC1 activation and breast cancer susceptibility (C Wang, S Rajput, K Watabe, D F Liao, D Cao Front Biosci 2010; 2:515-26).

Furthermore in central nervous system disorders including but not limited to Alzheimer's disease, Parkinson disease and epilepsy, impairements in neuronal energy metabolism have been described (Ogawa M, Fukuyama H, Ouchi Y, Yamauchi H, Kimura J, J Neurol Sci. 1996; 139(1):78-82). Interventions targeting this metabolic defect may prove beneficial to the patients. One promising intervention is therefore to provide the glucose-compromised neuronscerebral brain neurons with ketone bodies as an alternative substrate (S T Henderson Neurotherapeutics, 2008, 5:470-480; L C Costantini, L J Barr, J L Vogel, S T Henderson BMC Neurosci. 2008, 9 Suppl 2:S16; K W Baranano, A L Hartman. Curr Treat Options Neurol. 2008; 10:410-9). ACC inhibition leading to increased fatty acid oxidation may thereby result in increases in the blood levels of ketone bodies thereby providing an alternative energy substrate for the brain.

Preclinical and clinical evidence indicates that ketone bodies can provide neuroprotective effects in models of Parkinson's disease, AD, hypoxia, ischemia, amyotrophic lateral sclerosis and glioma (L C Costantini, L J Barr, J L Vogel, S T Henderson BMC Neurosci. 2008, 9 Suppl 2:S16) and improved cognitive scores in Alzheimers Diseases patients (M A Reger, S T Henderson, C Hale, B Cholerton, L D Baker, G S Watson, K Hydea, D Chapmana, S Craft Neurobiology of Aging 25 (2004) 311-314). The end result of increased ketone levels is an improvement in mitochondrial efficiency and reduction in the generation of reactive oxygen species (for reviews see L C Costantini, L J Barr, J L Vogel, S T Henderson BMC Neurosci. 2008, 9 Suppl 2:S16; K W Baranano, A L Hartman. Curr Treat Options Neurol. 2008; 10:410-9).

AIM OF THE PRESENT INVENTION

The aim of the present invention is to provide new compounds, in particular new azetidine derivatives, which are active with regard to acetyl-CoA carboxylase(s).

Another aim of the present invention is to provide new compounds, in particular new azetidine derivatives, which are active with regard to ACC2

A further aim of the present invention is to provide new compounds, in particular new azetidine derivatives, which have an inhibitory effect on acetyl-CoA carboxylase(s) in vitro and/or in vivo and possess suitable pharmacological and pharmacokinetic properties to use them as medicaments.

A further aim of the present invention is to provide new compounds, in particular new azetidine derivatives, which have an inhibitory effect on ACC2 in vitro and/or in vivo and possess suitable pharmacological and pharmacokinetic properties to use them as medicaments.

A further aim of the present invention is to provide effective ACC inhibitors, in particular for the treatment of metabolic disorders, for example of obesity and/or diabetes.

A further aim of the present invention is to provide methods for treating a disease or condition mediated by the inhibition of acetyl-CoA carboxylase(s) in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular azetidine derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

Within the scope of the present invention it has now surprisingly been found that the new compounds of general formula (I) as described hereinafter exhibit an inhibiting activity with regard to acetyl-CoA carboxylase(s).

According to another aspect of the present invention it has been found that the new compounds of general formula (I) as described hereinafter exhibit an inhibiting activity with regard to ACC2.

Therefore, in a first aspect the present invention provides a compound of general formula (I)

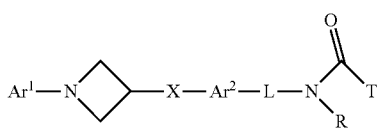

(I)

wherein $Ar^1$ is selected from the group $Ar^1$-G1 consisting of:
6- to 10-membered aryl and 5- to 10-membered heteroaryl, which may each be substituted with one or more substituents $R^1$,
wherein two substituents $R^1$ linked to adjacent C-atoms of $Ar^1$ together may form a $C_{3-5}$-alkylene bridge in which 1, 2 or 3 $CH_2$-groups may be replaced independently of each other by O, C(=O), S, S(=O), $S(=O)_2$, NH or $N(C_{1-4}$-alkyl)-, wherein the alkylene bridge may optionally be substituted by one or two F atoms or one or two $C_{1-3}$-alkyl groups; and $R^1$ is selected from the group $R^1$-G1 consisting of:
H, F, Cl, Br, I, CN, OH, —$NO_2$, $C_{2-6}$-alkenyl, $C_{2-6}$-alkynyl, $C_{3-10}$-carbocyclyl, $C_{3-10}$-carbocyclyl-$C_{1-3}$-alkyl, $C_{3-6}$-alkenyl-O—, $C_{3-6}$-alkynyl-O—, $C_{3-10}$-carbocyclyl-O—, $C_{3-10}$-carbocyclyl-$C_{1-3}$-alkyl-O—, $C_{1-6}$-alkyl-S(=O)—, $C_{1-6}$-alkyl-S(=O)$_2$—, $C_{3-10}$-carbocyclyl-S—, $C_{3-10}$-carbocyclyl-$C_{1-3}$-alkyl-S—, $C_{1-4}$-alkyl-C(=O)—, $C_{3-10}$-carbocyclyl-C(=O)—, $R^{N1}R^{N2}N$—, $R^{N1}R^{N2}N$—$C_{2-3}$-alkyl-O—, $R^{N1}R^{N2}N$—C(=O)—, $R^{N1}R^{N2}N$—S(=O)$_2$—, $C_{1-6}$-alkyl-C(=O)—$NR^{N1}$—, $C_{1-6}$-alkyl-S(=O)$_2$—$NR^{N1}$—, HO—C(=O)—, $C_{1-6}$-alkyl-O—C(=O)—, heterocyclyl, heterocyclyl-O—, heterocyclyl-$C_{1-3}$-alkyl, heterocyclyl-$C_{1-3}$-alkyl-O—, heterocyclyl-C(=O)—, aryl, aryl-$C_{1-3}$-alkyl, aryl-O—, heteroaryl, heteroaryl-$C_{1-3}$-alkyl, heteroaryl-O— and heteroaryl-$C_{1-3}$-alkyl-O—, wherein in each carbocyclyl and heterocyclyl a $CH_2$-group may optionally be replaced by —C(=O)— or —C(=$CR^{N2}_2$)—, and wherein each carbocyclyl and heterocyclyl may be optionally substituted with one or more $C_{1-4}$-alkyl, which may be optionally substituted with one or more substituents $R^C$, and wherein each alkyl, carbocyclyl and heterocyclyl may be optionally substituted with one or more substituents $R^C$, and wherein each heterocyclyl may be optionally substituted with aryl or heteroaryl, and wherein each aryl and heteroaryl group may be optionally substituted with one or more substituents $R^2$, $R^C$ is selected from the group $R^C$-G1 consisting of:
F, Cl, Br, CN, OH, $C_{1-4}$-alkyl-O—, $C_{3-7}$-cycloalkyl-O—, $C_{3-7}$-cycloalkyl-$C_{1-3}$-alkyl-O—, $H_2N$—, ($C_{1-4}$-alkyl)NH—, ($C_{1-4}$-alkyl)$_2$N—, $C_{1-4}$-alkyl-C(=O)—, $C_{1-4}$-alkyl-S(=O)$_2$—, HO—C(=O)— and $C_{1-4}$-alkyl-O—C(=O)—, wherein each alkyl or cycloalkyl may be optionally substituted with one or more substituents selected from F and OH, and $R^{N1}$ is selected from the group $R^{N1}$-G1 consisting of:
H, $C_{1-6}$-alkyl, $C_{3-10}$-carbocyclyl, $C_{3-10}$-carbocyclyl-$C_{1-3}$-alkyl, $C_{3-6}$-alkenyl, $C_{3-6}$-alkynyl, heterocyclyl, heterocyclyl-$C_{1-3}$-alkyl, aryl, aryl-$C_{1-3}$-alkyl, heteroaryl and heteroaryl-$C_{1-3}$-alkyl, wherein each carbocyclyl and heterocyclyl may be optionally substituted with one or more $C_{1-4}$-alkyl, and wherein in each carbocyclyl and heterocyclyl a $CH_2$-group may optionally be replaced by —C(=O)—, and wherein each alkyl, carbocyclyl and heterocyclyl may be optionally substituted with one or more substituents $R^C$, and wherein each aryl and heteroaryl group may be optionally substituted with one or more substituents $R^2$, $R^{N2}$ is selected from the group $R^{N2}$-G1 consisting of: H and $C_{1-6}$-alkyl, and $Ar^2$ is selected from the group $Ar^2$-G1 consisting of:
phenylene and a 5- or 6-membered monocyclic heteroaryl group containing 1, 2 or 3 heteroatoms selected from N, O, or S, wherein all of the before mentioned groups may be optionally substituted with one or more substituents $R^2$, and $R^2$ is selected from the group $R^2$-G1 consisting of:
F, Cl, Br, CN, OH, $C_{1-4}$-alkyl-, $C_{1-4}$-alkyl-O—, $C_{1-4}$-alkyl-S—, $C_{1-4}$-alkyl-S(=O)$_2$—, $H_2N$—, ($C_{1-4}$-alkyl)NH—, ($C_{1-4}$-alkyl)$_2$N—, $C_{1-4}$-alkyl-C(=O)—NH— and heterocyclyl, wherein each alkyl may be optionally substituted with one or more F-atoms and/or with a substituent selected from OH, $C_{1-3}$-alkyl-O— and CN; and wherein two substituents $R^2$ attached to an aryl or heteroaryl group may be linked to each other and form a $C_{2-5}$-alkylene bridging group in which 1 or 2-$CH_2$-groups may be replaced by a group independently of each other selected from O, S, NH and N($C_{1-4}$-alkyl)-, wherein the $C_{2-5}$-alkylene bridging group is optionally be substituted by 1 or 2 $C_{1-3}$-alkyl groups;

L is selected from the group L-G1 consisting of:
a $C_{1-4}$-alkylene group that is optionally substituted by one or two $CH_3$;

X is selected from the group X-G1 consisting of: O and S;

R is selected from the group R-G1 consisting of: H and $C_{1-3}$-alkyl; and

T is selected from the group T-G1 consisting of:
$C_{1-6}$-alkyl, $C_{2-6}$-alkenyl, $C_{2-6}$-alkynyl, $C_{3-10}$-carbocyclyl, $C_{3-10}$-carbocyclyl-$C_{1-3}$-alkyl, $C_{1-6}$-alkyl-O—, $C_{3-10}$-carbocyclyl-O—, $C_{3-10}$-carbocyclyl-$C_{1-3}$-alkyl-O—, $C_{1-6}$-alkyl-S—, $C_{3-10}$-carbocyclyl-S—, $C_{3-10}$-carbocyclyl-$C_{1-3}$-alkyl-S—, $C_{1-4}$-alkyl-C(=O)—$C_{1-4}$-alkyl-S(=O)$_2$—, $R^{N1}R^{N2}$—N—, $R^{N1}R^{N2}$—N—$C_{1-3}$-alkyl-, $R^{N1}R^{N2}$—N—CO—, $C_{1-4}$'-alkyl-C(=O)—$R^{N2}$N—$C_{1-3}$-alkyl, heterocyclyl, aryl and heteroaryl, wherein in each carbocyclyl and heterocyclyl a $CH_2$-group may optionally be replaced by —C(=O)—, and wherein each carbocyclyl and heterocyclyl may be optionally substituted with one or more $C_{1-4}$-alkyl, which may be optionally substituted with one or more substituents $R^C$, and wherein each alkyl, carbocyclyl and heterocyclyl may be optionally substituted with one or more substituents $R^C$, and wherein each alkyl may optionally be substituted with a heteroaryl group; and wherein each aryl and heteroaryl group may be optionally substituted with one or more substituents $R^2$;

including any tautomers and stereoisomers thereof, or a salt thereof or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of acetyl-CoA carboxylase(s) in a patient in need thereof characterized in that a compound of general formula (I) or a pharmaceutically acceptable salt thereof is administered to the patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided a method for treating a cardiovascular disease or disorder in a patient in need thereof characterized in that a compound of general formula (I) or a pharmaceutically acceptable salt thereof is administered to the patient.

According to another aspect of the invention, there is provided a method for treating a neurodegenerative disease or disorder or for treating a disease or disorder of the central nervous system in a patient in need thereof characterized in that a compound of general formula (I) or a pharmaceutically acceptable salt thereof is administered to the patient.

According to another aspect of the invention, there is provided a method for treating a cancer, a malignant disorder or a neoplasia in a patient in need thereof characterized in that a compound of general formula (I) or a pharmaceutically acceptable salt thereof is administered to the patient.

According to another aspect of the invention, there is provided the use of a compound of the general formula (I) or a physiologically acceptable salt thereof for the manufacture of a medicament for a therapeutic method as described hereinbefore and hereinafter.

According to another aspect of the invention, there is provided a compound of the general formula (I) or a physiologically acceptable salt thereof for a therapeutic method as described hereinbefore and hereinafter.

In a further aspect this invention relates to a method for treating a disease or condition mediated by the inhibition of acetyl-CoA carboxylase(s) in a patient that includes the step of administering to the patient in need of such treatment a therapeutically effective amount of a compound of the general formula (I) in combination with a therapeutically effective amount of one or more additional therapeutic agents.

In a further aspect this invention relates to a use of a compound of the general formula (I) in combination with one or more additional therapeutic agents for the treatment or prevention of diseases or conditions which are mediated by the inhibition of acetyl-CoA carboxylase(s).

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $Ar^1$, $Ar^2$, X, R, T, $R^1$, $R^2$, $R^C$, $R^{N1}$, $R^{N2}$, and L are defined as above and hereinafter. If residues, substituents, or groups occur several times in a compound, as for example $R^C$, $R^{N1}$, $R^{N2}$ or $R^2$, they may have the same or different meanings. Some preferred meanings of individual groups and substituents of the compounds according to the invention will be given hereinafter. Any and each of these definitions may be combined with each other.

$Ar^1$:

$Ar^1$-G1:

The group $Ar^1$ is preferably selected from the group $Ar^1$-G1 as defined hereinbefore and hereinafter.

$Ar^1$-G2:

In one embodiment the group $Ar^1$ is selected from the group $Ar^1$-G2 consisting of: phenyl, naphthyl, dihydronaphthyl, tetrahydronaphthyl, naphthyl and a 5- or 6-membered monocyclic or 9- or 10-membered bicyclic ring system containing 1, 2 or 3 heteroatoms selected from N, O, S, or $S(O)_r$, with r=1 or 2, wherein at least one of the heteroatoms is part of an aromatic ring, and wherein all of the before mentioned groups may be optionally substituted with one or more substituents $R^1$ particularly wherein all of the before mentioned groups may be optionally substituted with a substituent $R^1$ and optionally one or more substituents $R^2$, and wherein two substituents $R^1$ linked to adjacent C-atoms of $Ar^1$ may be connected with each other and together form a $C_{3-5}$-alkylene bridging group in which 1, 2 or 3 $CH_2$-groups may be replaced independently of each other by O, C(=O), S, S(=O), $S(=O)_2$, NH or $N(C_{1-4}$-alkyl)-, wherein the alkylene bridging group may optionally be substituted by one or two F atoms or one or two $C_{1-3}$-alkyl groups.

$Ar^1$-G3:

In another embodiment the group $Ar^1$ is selected from the group $Ar^1$-G3 consisting of: phenyl, naphthyl, pyridyl, 2H-pyridin-2-onyl, pyrimidinyl, pyridazinyl, pyrazinyl, furanyl, thienyl, pyrrolyl, imidazolyl, triazolyl, oxazolyl, isoxazolyl, pyrazolyl, thiazolyl, quinolinyl, isoquinolinyl, quinoxalinyl, indolyl, benzofuranyl, benzoimidazolyl, benzoxazolyl, benzoisoxazolyl, benzthiazolyl, benzotriazolyl, oxazolopyrimidinyl, 2,3-dihydrobenzofuranyl, benzo[1,3]dioxolyl, 2,3-dihydro-benzo[1,4]dioxinyl, 2,3,4,5-tetrahydro-benzo[b]oxepinyl, and 3,4-dihydro-2H-benzo[b][1,4]dioxepinyl, wherein the before mentioned bicyclic groups preferably are linked to the azetidine ring of the core structure of the formula (I) via an aromatic or heteroaromatic ring of the bicyclic group, and wherein all of the before mentioned mono- and bicyclic groups may be optionally substituted with one or more substituents $R^1$, particularly wherein all of the before mentioned mono- or bicyclic groups may be optionally substituted with a substituent $R^1$ and optionally one or more substituents $R^2$.

$Ar^1$-G4:

In another embodiment the group $Ar^1$ is selected from the group $Ar^1$-G4 consisting of: phenyl, pyridinyl, pyrimidinyl, benzoxazolyl, benzoisoxazolyl, benzthiazolyl, quinolinyl, isoquinolinyl, quinoxalinyl and oxazolopyrimidinyl, wherein the above-mentioned phenyl, pyridinyl and pyrimidinyl are each substituted with one to three groups independently selected from $R^1$, and/or wherein two adjacent carbon atoms of a phenyl group may be linked to each other via a —O—CH$_2$—O—, —O—CF$_2$—O—, —O—CH$_2$—CH$_2$—O—, —O—CH$_2$—CH$_2$—CH$_2$—CH$_2$—, —O—CH$_2$—CH$_2$—CH$_2$—C(CH$_3$)$_2$—, —O—CH$_2$—CH$_2$—CH$_2$—O— or —O—CH$_2$—C(CH$_3$)$_2$—CH$_2$—O— bridge, and wherein the above-mentioned benzoxazolyl, benzoisoxazolyl, benzthiazolyl, quinolinyl, isoquinolinyl, quinoxalinyl and oxazolopyrimidinyl groups are each optionally substituted with Cl, CH$_3$ or phenyl.

$R^1$ may be any of the subgroups of $R^1$ as defined below. However, with respect to $Ar^1$-G4, $R^1$ is preferably a group selected from the group $R^1$-G4 as defined below.

$Ar^1$-G5:

In another embodiment the group $Ar^1$ is selected from the group $Ar^1$-G5 consisting of: phenyl, pyridinyl and pyrimidinyl, wherein the above-mentioned phenyl and pyridinyl groups are each substituted with one to three groups independently selected from $R^1$, and wherein the above-mentioned pyrimidinyl groups is substituted with one or two $R^1$, and wherein two adjacent carbon atoms of a phenyl group may be linked to each other via a —O—CH$_2$—CH$_2$—O—, —O—CH$_2$—CH$_2$—CH$_2$—C(CH$_3$)$_2$—, —O—CH$_2$—CH$_2$—CH$_2$—O—, or —O—CH$_2$—C(CH$_3$)$_2$—CH$_2$—O— bridge.

$R^1$ may be any of the subgroups of $R^1$ as defined below. However, with respect to $Ar^1$-G5, $R^1$ is preferably a group selected from the group $R^1$-G5 as defined below.

$Ar^1$-G6:

In another embodiment the group $Ar^1$ is selected from the group $Ar^1$-G6 consisting of: phenyl and pyridinyl, which are each optionally substituted with one to three substituents independently selected from the group consisting of:

F, Cl, Br, CN, CF$_3$, C$_{1-4}$ alkyl, phenyl, —CO—O—C$_{1-4}$-alkyl, —O— phenyl, —O -pyrimidinyl, —O—C$_{1-4}$ alkyl, —O—C$_{3-7}$ cycloalkyl and —O—CH$_2$—C$_{3-5}$cycloalkyl, wherein the cycloalkyl groups may optionally be substituted with one CN or one or two F.

Preferred substituents of the phenyl group are:

F, Cl, Br, CN, CF$_3$, C$_{1-4}$ alkyl, —O—C$_{1-4}$ alkyl, —O—C$_{3-5}$ cycloalkyl, —O—CH$_2$-cyclopropyl and

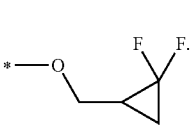

Preferred substituents of the pyridinyl group are:

F, Cl, Br, CN, CF$_3$, phenyl, —CO—O—CH$_2$CH$_3$, —O— phenyl, —O— pyrimidinyl, C$_{1-3}$ alkyl, —O—C$_{1-4}$ alkyl, —O—CH$_2$-cyclopropyl and

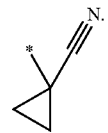

$Ar^1$-G6a:

In another embodiment the group $Ar^1$ is selected from the group $Ar^1$-G6a consisting of:

phenyl, which is optionally substituted with one to three substituents independently selected from the group consisting of:

F, Cl, Br, CN, CF$_3$, C$_{1-4}$ alkyl, —O—C$_{1-4}$ alkyl, —O—C$_{3-7}$ cycloalkyl and —O—CH$_2$—C$_{3-5}$ cycloalkyl, wherein the cycloalkyl groups may optionally be substituted with one or two F.

Preferred substituents of the phenyl group are:

F, Cl, Br, CN, CF$_3$, C$_{1-4}$ alkyl, —O—C$_{1-4}$ alkyl, —O—C$_{3-5}$ cycloalkyl, cyclopropyl and

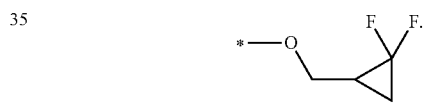

$R^1$:

$R^1$-G1:

The group $R^1$ is preferably selected from the group $R^1$-G1 as defined hereinbefore and hereinafter, $R^1$-G2:

In another embodiment the group $R^1$ is selected from the group $R^1$-G2 consisting of: H, F, Cl, Br, I, ON, OH, —NO$_2$, C$_{1-6}$-alkyl, C$_{2-6}$-alkenyl, C$_{3-7}$-cycloalkyl, C$_{1-3}$-alkyl, C$_{1-6}$-alkyl-O—, C$_{3-7}$-cycloalkyl-O—, C$_{3-7}$-cycloalkyl-C$_{1-3}$-alkyl-O—, C$_{1-6}$-alkyl-S—, C$_{1-6}$-alkyl-S(=O)$_2$—, C$_{1-4}$-alkyl-C(=O)—, C$_{3-7}$-cycloalkyl-C(=O)—, R$^{N1}$R$^{N2}$N—, R$^{N1}$R$^{N2}$N—C$_{2-3}$-alkyl-O—, R$^{N1}$R$^{N2}$N—C(=O)—, R$^{N1}$R$^{N2}$N—S(=O)$_2$—, C$_{1-4}$-alkyl-C(=O)—NR$^{N1}$—, C$_{1-4}$-alkyl-S(=O)$_2$—NR$^{N1}$—, C$_{1-4}$-alkyl-C(=O)—NR$^{N1}$—C$_{1-3}$-alkyl-, HO—C(=O)—, C$_{1-6}$-alkyl-O—C(=O)—, heterocyclyl, heterocyclyl-O—, heterocyclyl-C$_{1-3}$-alkyl, heterocyclyl-C$_{1-3}$-alkyl-O—, heterocyclyl-C(=O)—, phenyl, phenyl-C$_{1-3}$-alkyl, phenyl-O—, phenyl-C$_{1-3}$-alkyl-O—, heteroaryl, heteroaryl-C$_{1-3}$-alkyl, heteroaryl-O— and heteroaryl-C$_{1-3}$-alkyl-O—, wherein in each cycloalkyl and heterocyclyl a CH$_2$-group may optionally be replaced by —C(=O)—, and wherein each cycloalkyl and heterocyclyl may be optionally substituted with one or more C$_{1-4}$-alkyl, which may be optionally substituted with one or more substituents R$^C$, and wherein each alkyl, cycloalkyl and heterocyclyl may be optionally substituted with one or more substituents R$^C$, and wherein each heterocyclyl may be optionally substituted with aryl or heteroaryl, and wherein each phenyl and heteroaryl group may be optionally substituted with one or more substituents $R^2$, and wherein each heterocyclyl group is selected form the group consisting of: piperidinyl, piperazinyl, morpholinyl, pyrrolidinyl, tetrahydrofuranyl and azetidinyl, and wherein each heteroaryl group is selected form the group consisting of: pyridinyl, pyrimidinyl, pyrazinyl, furanyl, thienyl, pyridazinyl, pyrrolyl, pyrazolyl, imidazolyl, oxazolyl, isoxazolyl, thiazolyl, indolyl, and benzimidazolyl.

$R^1$-G3:

In another embodiment the group $R^1$ is selected from the group $R^1$-G3 consisting of: H, F, Cl, Br, CN, OH, $C_{1-4}$-alkyl, $C_{2-4}$-alkenyl, $C_{3-7}$-cycloalkyl, $C_{3-7}$-cycloalkyl-$CH_2$—, $C_{1-4}$-alkyl-O—, $C_{3-7}$-cycloalkyl-O—, $C_{3-7}$-cycloalkyl-$C_{1-3}$-alkyl-O—, $C_{1-4}$-alkyl-S(=O)$_2$, $R^{N1}R^{N2}N$—, HO—C(=O)—, $C_{1-4}$-alkyl-O—C(=O)—, phenyl, phenyl-O—, phenyl-$CH_2$—O—, pyridinyl, wherein each alkyl, cycloalkyl and heterocyclyl may be optionally substituted with one to three substituents independently selected from the group consisting of F and CN, and wherein each phenyl and pyridinyl group may be optionally substituted with one F or —OCH$_3$.

$R^1$-G4:

In another embodiment the group $R^1$ is selected from the group $R^1$-G4 consisting of: F, Cl, Br, CN, $C_{1-4}$ alkyl, —O—$C_{1-4}$ alkyl, $C_{3-7}$ cycloalkyl, —O—$C_{3-7}$ cycloalkyl, —O—($C_{1-2}$alkyl)-$C_{3-7}$ cycloalkyl, —NH—$C_{3-7}$ cycloalkyl, —NH($C_{1-4}$ alkyl), —CO—O($C_{1-4}$ alkyl), phenyl, —O—phenyl, pyrimidinyl and pyridinyl, wherein the alkyl and cycloalkyl groups may optionally be substituted with one to three F and/or one CN, and wherein the phenyl and pyridinyl groups may optionally be substituted with one F or OCH$_3$.

$R^1$-G5:

In another embodiment the group $R^1$ is selected from the group $R^1$-G5 consisting of: F, Cl, CN, CF$_3$, $C_{1-4}$ alkyl, —O—$C_{1-4}$ alkyl, cyclopropyl, —O—$C_{3-5}$cycloalkyl, cyclopropyl, and

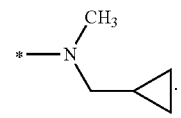

$R^1$-G5a:

In another embodiment the group $R^1$ is selected from the group $R^1$-G5a consisting of: F, Cl, Br, CN, CF$_3$, phenyl, —CO—O—CH$_2$CH$_3$, —O— phenyl, —O— pyrimidinyl, $C_{1-3}$ alkyl, —O—$C_{1-4}$ alkyl, —O—CH$_2$-cyclopropyl and

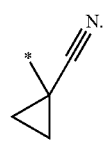

$R^1$-G5b:

In another embodiment the group $R^1$ is selected from the group $R^1$-G5b consisting of: Cl, Br, CF$_3$, $C_{1-4}$ alkyl, —O—$C_{1-4}$ alkyl, —CO—O—CH$_2$CH$_3$, cyclopropyl, phenyl, pyridinyl, —O—CH$_2$— cyclopropyl, and

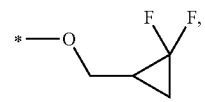

wherein the phenyl and pyridinyl may be substitued by F or —O—CH$_3$.

$R^1$-G5c:

In another embodiment the group $R^1$ is selected from the group $R^1$-G5c consisting of: —NH-cyclobutyl, —O—cyclobutyl and —NH(CH$_2$CH$_3$).

$R^1$-G5d:

In another embodiment the group $R^1$ is selected from the group $R^1$-G5d consisting of: CF$_3$, —O—($C_{1-2}$-alkyl), —O—($C_{3-4}$-cycloalkyl), —O—CH$_2$-cyclopropyl and $R^C$ $R^C$-G1

The group $R^C$ is preferably selected from the group $R^C$-G1 as defined hereinbefore and hereinafter.

In one embodiment the group $R^C$ is selected from the group $R^C$-G2 consisting of: F, Cl, Br, CN, OH, $C_{1-3}$-alkyl-O—, $C_{3-6}$-cycloalkyl-O—, H$_2$N—, ($C_{1-3}$-alkyl)NH—, ($C_{1-3}$-alkyl)$_2$N—, $C_{1-3}$-alkyl-C(=O)—, $C_{1-3}$-alkyl-S(=O)$_2$—, HO—C(=O)— and $C_{1-3}$-alkyl-O—C(=O)—, wherein each alkyl may be optionally substituted with one or more F-atoms and/or may be substituted with OH.

$R^C$-G3:

In another embodiment the group $R^C$ is selected from the group $R^C$-G3 consisting of: F, Cl, CN, OH and $C_{1-3}$-alkyl-O—.

In another embodiment the group $R^C$ is selected from the group $R^C$-G4 consisting of: F, CN, OH and —O—CH$_3$.

$R^{N1}$ $R^{N1}$-G1:

The group $R^{N1}$ is preferably selected from the group $R^{N1}$-G1 as defined hereinbefore and hereinafter.

With regard to an alkenyl or alkynyl group, for example $R^{N1}$, attached to the N-atom of an amino-group it is to be understood that the double or triple bond is preferably not conjugated with the N-atom.

$R^{N1}$-G2:

In one embodiment, the group $R^{N1}$ is selected from the group $R^{N1}$-G2 consisting of: H, $C_{1-4}$-alkyl, $C_{3-6}$-cycloalkyl, $C_{3-6}$-cycloalkyl-CH$_2$—, heterocyclyl, heterocyclyl-CH$_2$—, phenyl, phenyl-CH$_2$—, pyridyl, pyridyl-CH$_2$—, pyrazolyl-CH$_2$— and oxazolyl-$C_{1-3}$-alkyl;

wherein heterocyclyl is defined as hereinbefore and hereinafter, or each heterocyclyl is preferably selected from tetrahydrofuranyl, tetrahydropyranyl, pyrrolidinyl and piperidinyl; and wherein each cycloalkyl and heterocyclyl may be optionally substituted with one or two $C_{1-4}$-alkyl; and wherein each alkyl, cycloalkyl and heterocyclyl may be optionally substituted with one to three F; and wherein each alkyl, cycloalkyl and heterocyclyl may be optionally substituted with a substituent selected from OH, $C_{1-3}$-alkyl-O—, H$_2$N—, HO—C(=O)— and $C_{1-4}$-alkyl-O—C(=O)—; and wherein each phenyl, pyridyl, pyrazolyl and oxazolyl may be optionally substituted with one to three substituents $R^2$.

$R^{N1}$-G3:

In another embodiment the group $R^{N1}$ is selected from the group $R^{N1}$-G3 consisting of H, $C_{1-4}$-alkyl, $C_{3-6}$-cycloalkyl-$C_{1-3}$-alkyl- and $C_{3-6}$-cycloalkyl.

$R^{N2}$

The group $R^{N2}$ is preferably selected from the group $R^{N2}$-G1 as defined hereinbefore and hereinafter.

$R^{N2}$-G2:

In another embodiment the group $R^{N2}$ is selected from the group $R^{N2}$-G2 consisting of H and $C_{1-4}$-alkyl.

$R^{N2}$-G3:

In another embodiment the group $R^{N2}$ is selected from the group $R^{N2}$-G3 consisting of H and $CH_3$.

$Ar^2$:

$Ar^2$-G1:

The group $Ar^2$ is preferably selected from the group $Ar^2$-G1 as defined hereinbefore and hereinafter.

$Ar^2$-G2:

In another embodiment the group $Ar^2$ is selected from the group $Ar^2$-G2 consisting of: phenylene, pyridylene, pyrimidinylene, pyridazinylene, pyrazinylene, furanylene, thienylene, pyrrolylene, imidazolylene, triazolylene, oxazolylene, isoxazolylene, pyrazolylene and thiazolylene, wherein all of the before mentioned groups may be optionally substituted with one or more substituents $R^2$.

$Ar^2$-G3:

In another embodiment the group $Ar^2$ is selected from the group $Ar^2$-G3 consisting of phenylene and pyridylene, wherein all of the before mentioned groups may be optionally substituted with one to three substituents $R^2$.

$Ar^2$-G3a:

In another embodiment the group $Ar^2$ is selected from the group $Ar^2$-G3a consisting of phenylene and pyridylene.

$Ar^2$-G4:

In another embodiment the group $Ar^2$ is selected from the group $Ar^2$-G4 consisting of: phenylene, which may be optionally substituted with one or two substituents $R^2$.

$Ar^2$-G4a:

In another embodiment the group $Ar^2$ is selected from the group $Ar^2$-G4a consisting of phenylene.

$Ar^2$-G5:

In another embodiment the group $Ar^2$ is selected from the group $Ar^2$-G5 consisting of:

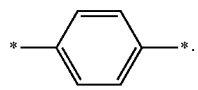

$R^2$:

$R^2$-G1:

The group $R^2$ is preferably selected from the group $R^2$-G1 as defined hereinbefore and hereinafter.

$R^2$-G2:

In another embodiment the group $R^2$ is selected from the group $R^2$-G2 consisting of: F, Cl, Br, CN, OH, $C_{1-3}$-alkyl-, $C_{1-3}$-alkyl-O—, $C_{1-3}$-alkyl-S—, $H_2N$—, $(C_{1-3}$-alkyl)NH—, $(C_{1-3}$-alkyl)$_2$N—, $C_{1-3}$-alkyl-C(=O)—NH— and heterocyclyl;
wherein each alkyl may be optionally substituted with one or more F-atoms and/or a substituent selected from OH, $C_{1-3}$-alkyl-O— and CN; and
wherein heterocyclyl is defined as hereinbefore and hereinafter, or heterocyclyl preferably denotes a $C_{3-6}$-cycloalkyl ring wherein one or two —$CH_2$-groups are replaced by a group selected from —O—, —NH—, —N($CH_3$)—; and
wherein two substituents $R^2$ attached to an aryl or heteroaryl group may be linked to each other and form a $C_{2-5}$-alkylene bridging group in which 1 or 2-$CH_2$-groups may be replaced by a group independently of each other selected from O, NH and N($CH_3$)—, wherein the $C_{2-5}$-alkylene bridging group is optionally be substituted by 1 or 2 $CH_3$— groups.

$R^2$-G3:

In another embodiment the group $R^2$ is selected from the group $R^2$-G3 consisting of: F, Cl, CN, OH, $C_{1-3}$-alkyl-, $C_{1-3}$-alkyl-O—, $C_{1-3}$-alkyl-S—, $H_2N$—, $(C_{1-3}$-alkyl)NH—, $(C_{1-3}$-alkyl)$_2$N— and $C_{1-3}$-alkyl-C(=O)—NH—;
wherein each alkyl may be optionally substituted with one or more F-atoms and/or a substituent selected from OH, $CH_3$—O— and CN; and
wherein two substituents $R^2$ attached to adjacent C-atoms of an aryl or heteroaryl group may be linked to each other and form a —$CH_2$—$CH_2$—O—, —O—$CH_2$—$CH_2$—O— or —O—$CH_2$—O— bridging group which is optionally substituted by 1 or 2 $CH_3$— groups.

$R^2$-G4:

In another embodiment the group $R^2$ is selected from the group $R^2$-G4 consisting of: F, Cl, $C_{1-2}$-alkyl-, $C_{1-2}$-alkyl-O—, $C_{1-3}$-alkyl-C(=O)—NH and HO—$CH_2$—C(=O)—NH—.

$R^2$-G4a:

In another embodiment the group $R^2$ is selected from the group $R^2$-G4a consisting of: F and —$OCH_3$.

$R^2$-G4b:

In another embodiment the group $R^2$ is selected from the group $R^2$-G4b consisting of: $CH_3$, $CH_3$—C(=O)—NH— and HO—$CH_2$—C(=O)—NH—.

L:

L-G1:

The group L is preferably selected from the group L-G1 as defined hereinbefore and hereinafter.

L-G2:

In one embodiment the group L is selected from the group L-G2 consisting of: a linear $C_{1-3}$-alkylene group that is optionally substituted with one or two $CH_3$.

L-G3:

In another embodiment the group L is selected from the group L-G3 consisting of: a linear $C_{1-2}$-alkylene group that is optionally substituted with one $CH_3$.

L-G4:

In another embodiment the group L is selected from the group L-G4 consisting of: —CH($CH_3$)— and —CH($CH_3$)—($CH_2$)—.

L-G5:

In another embodiment the group L is selected from the group L-G5 consisting of: —CH($CH_3$)— and —CH($CH_3$)—($CH_2$)—,
wherein the —CH($CH_3$)— moiety of the —CH($CH_3$)—($CH_2$)— group is attached to the N atom in formula (I) and the —$CH_2$—* moeity of the —CH($CH_3$)—($CH_2$)— group is attached to the $Ar^2$ group.

L-G6:

In another embodiment the group L is selected from the group L-G6 consisting of —CH($CH_3$)—.

L-G6a:

According an embodiment L-G6a the group L is

embracing

and

wherein the right-hand side of each of the before-mentiones moieties is attached to the N atom in formula (I) and the left-hand side of each of the before-mentiones moieties is attached to the $Ar^2$ group.

A preferred example of the group L-G6a is

wherein the right-hand side of each of the before-mentiones moieties is attached to the N atom in formula (I) and the left-hand side of each of the before-mentiones moieties is attached to the $Ar^2$ group.

Another preferred example of the group L-G6a is

wherein the right-hand side of each of the before-mentiones moieties is attached to the N atom in formula (I) and the left-hand side of each of the before-mentiones moieties is attached to the $Ar^2$ group.

L-G7:

In another embodiment the group L is selected from the group L-G7 consisting of: —CH(CH$_3$)—(CH$_2$)—, wherein the —CH(CH$_3$)— moiety of the —CH(CH$_3$)—(CH$_2$)— group is attached to the N atom in formula (I) and the —CH$_2$—* moeity of the —CH(CH$_3$)—(CH$_2$)— group is attached to the $Ar^2$ group.

L-G7a:

In another embodiment the group L is selected from the group L-G7a consisting of:

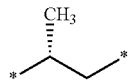

wherein the —CH(CH$_3$)— moiety of the above group is attached to the N atom in formula (I) and the —CH$_2$—* moeity of the above group is attached to the $Ar^2$ group.

L-G7b:

In another embodiment the group L is selected from the group L-G7b consisting of:

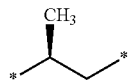 [SMILES: *C[C@@H](*)C]

wherein the —CH(CH$_3$)— moiety of the above group is attached to the N atom in formula (I) and the —CH$_2$—* moeity of the above group is attached to the $Ar^2$ group.

X:

X-G1:

The group X is preferably selected from the group X-G1 as defined hereinbefore and hereinafter.

X-G2:

In another embodiment the group X is selected from the group X-G2 consisting of O.

X-G3:

In another embodiment the group X is selected from the group X-G3 consisting of S.

R:

R-G1:

The group R is preferably selected from the group $R^N$-G1 as defined hereinbefore and hereinafter.

R-G2:

In another embodiment the group R is selected from the group $R^N$-G2 consisting of H and methyl.

R-G3:

In another embodiment the group R is selected from the group $R^N$-G3 consisting of H.

T:

T-G1:

The group T is preferably selected from the group T-G1 as defined hereinbefore and hereinafter.

T-G2:

In another embodiment the group T is selected from the group T-G2 consisting of: $C_{1-6}$-alkyl, $C_{2-6}$-alkenyl, $C_{2-6}$-alkynyl, $C_{3-7}$-cycloalkyl, $C_{3-7}$-cycloalkenyl, $C_{1-6}$-alkyl-O—, $C_{3-7}$-cycloalkyl-O—, $C_{1-6}$-alkyl-S—, $C_{3-7}$-cycloalkyl-$C_{1-3}$-alkyl-S—, $C_{1-4}$-alkyl-C(=O)—, $C_{1-4}$-alkyl-S(=O)$_2$—, $R^{T1}R^{T2}$—N—, $R^{T1}R^{T2}$—N—$C_{1-3}$-alkyl-, $R^{T1}R^{T2}$—N—CO—, $C_{1-4}$-alkyl-C(=O)—$R^{T2}$N—$C_{1-3}$-alkyl, heterocyclyl, phenyl and heteroaryl;

wherein in each cycloalkyl and heterocyclyl a CH$_2$-group may optionally be replaced by —C(=O)—; and wherein each cycloalkyl and heterocyclyl may be optionally substituted with one or more $C_{1-4}$-alkyl, which may be optionally substituted with one or more substituents $R^C$; and wherein each alkyl, cycloalkyl and heterocyclyl may be optionally substituted with one or more substituents $R^C$; and wherein each alkyl may optionally be substituted with a heteroaryl group; and wherein heterocyclyl is defined as hereinbefore and hereinafter; preferably heterocyclyl is azetidinyl, pyrrolidinyl, piperidinyl, morpholinyl, oxetanyl, tetrahydrofuranyl or tetrahydropyranyl; and wherein each heteroaryl is selected from the group consisting of phenyl, pyridyl, pyrimidinyl, pyridazinyl, pyrazinyl, furanyl, thienyl, pyrrolyl, imidazolyl, pyrazolyl, triazolyl, oxazolyl, isoxazolyl, isothiazolyl and thiazolyl; and wherein each aryl and heteroaryl group may be optionally substituted with one or more substituents $R^2$.

T-G3:

In another embodiment the group T is selected from the group T-G3 consisting of: $C_{1-4}$-alkyl, $C_{2-4}$-alkenyl, $C_{3-6}$-cycloalkyl, $C_{3-7}$-cycloalkenyl, $C_{3-5}$-cycloalkyl-$C_{1-3}$-alkyl-, heteroaryl-$C_{1-3}$-alkyl-, $C_{1-3}$-alkyl-O—, $R^{T1}R^{T2}$—N—, $C_{1-3}$-alkyl-C(=O)—$R^{T2}$N—$C_{1-3}$-alkyl-, heterocyclyl, phenyl and heteroaryl, wherein in each heterocyclyl, a $CH_2$-group may optionally be replaced by —C(=O)—; and wherein each cycloalkyl and heterocyclyl may be optionally substituted with one or more $C_{1-3}$-alkyl, which may be optionally substituted with one or more substituents $R^C$; and wherein each alkyl, cycloalkyl and heterocyclyl may be optionally substituted with one or more F; and wherein heterocyclyl is defined as hereinbefore and hereinafter, preferably heterocyclyl is selected from the group consisting of

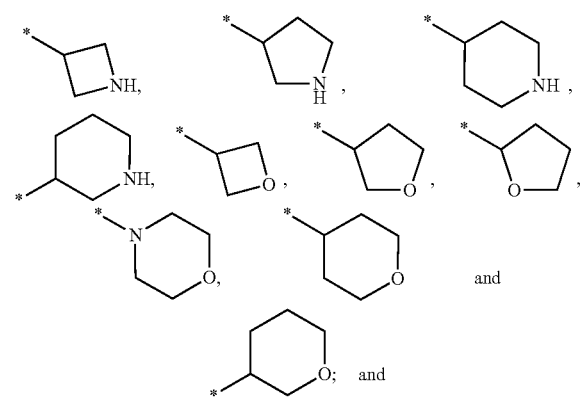

wherein heteroaryl is selected from the group consisting of pyridyl, pyrimidinyl, pyridazinyl, pyrazinyl, furanyl, thienyl, pyrrolyl, imidazolyl, pyrazolyl, triazolyl, oxazolyl, isoxazolyl, thiazolyl and isothiazolyl; and wherein each phenyl and heteroaryl group may be optionally substituted with one or more substituents $R^2$.

T-G4:

In another embodiment the group T is selected from the group T-G4 consisting of: $C_{1-4}$-alkyl, $C_{2-4}$-alkenyl, $C_{3-5}$-cycloalkyl, $C_{5-6}$-cycloalkenyl, $C_{3-5}$-cycloalkyl-$CH_2$—, $C_{1-3}$-alkyl-O—, $R^{T1}R^{T2}$—N—, $C_{1-3}$-alkyl-C(=O)—$R^{T2}$N—$C_{1-3}$-alkyl, heterocyclyl, phenyl and heteroaryl, wherein $R^{T1}$ is H, $CH_3$ or $CH_2CH_3$; and $R^{T2}$ is H or $CH_3$; and wherein each alkyl, cycloalkyl and heterocyclyl may be optionally substituted with one F, CN, $CH_3$, $CF_3$, cyclopropyl, —$NH_2$, —$N(CH_3)_2$, pyridinyl, OH or —$OCH_3$; and wherein heterocyclyl is selected from the group consisting of:

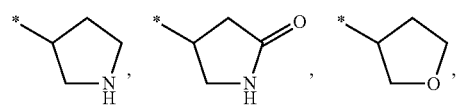

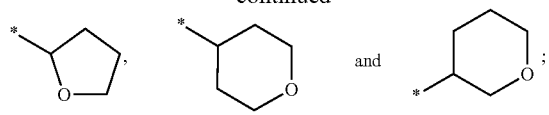

and wherein heteroaryl is selected from the group consisting of pyridyl, pyrimidinyl, pyridazinyl, pyrazinyl, furanyl, thienyl, pyrrolyl, imidazolyl, pyrazolyl, oxazolyl, isoxazolyl, thiazolyl and isothiazolyl; and wherein each phenyl and heteroaryl group may be optionally substituted with one or two substituents independently selected from $CH_3$, —NH—CO—$CH_3$, —NH—CO—$CH_2$—OH.

T-G5:

In another embodiment the group T is selected from the group T-G5 consisting of: $C_{1-4}$-alkyl, $C_{2-4}$-alkenyl, $C_{3-5}$-cycloalkyl, $C_{5-6}$-cycloalkenyl, cyclopropyl-$CH_2$—, $CH_3O$—, N—, $CH_3$—C(=O)—NH—$C_{1-3}$-alkyl, heterocyclyl, phenyl and heteroaryl, wherein $R^{T1}$ is H, $CH_3$ or $CH_2CH_3$; and $R^{T2}$ is H or $CH_3$; and wherein each alkyl, cycloalkyl and heterocyclyl may be optionally substituted with one F, CN, $CH_3$, $CF_3$, cyclopropyl, —$N(CH_3)_2$, pyridinyl, OH or —$OCH_3$; and wherein heterocyclyl is selected from the group consisting of:

wherein heteroaryl is selected from the group consisting of pyridyl, pyrimidinyl, pyridazinyl, furanyl, pyrazolyl, oxazolyl, isoxazolyl, thiazolyl and isothiazolyl; and wherein each phenyl and heteroaryl group may be optionally substituted with one or two substituents independently selected from $CH_3$, —NH—CO—$CH_3$, —NH—CO—$CH_2$—OH.

T-G5a:

In another embodiment the group T is selected from the group T-G5a consisting of: $CH_3$, cyclopropyl and —$N(CH_3)_2$, wherein the $CH_3$ group may optionally be substituted with one F, CN, $CH_3$, $CF_3$, cyclopropyl, —$N(CH_3)_2$, pyridinyl, OH, or —$OCH_3$.

T-G5b:

In another embodiment the group T is selected from the group T-G5a consisting of: $CH_3$ and —$N(CH_3)_2$, wherein the $CH_3$ group may optionally be substituted with one F, CN, $CH_3$, $CF_3$, cyclopropyl, —$N(CH_3)_2$, pyridinyl, OH, or —$OCH_3$.

T-G6:

In another embodiment the group T is selected from the group T-G6 consisting of: $CH_3$ optionally substituted with one F, CN, $CH_3$, $CF_3$, cyclopropyl, OH or —$OCH_3$.

T-G6a:

In another embodiment the group T is selected from the group T-G6a consisting of: $CH_3$.

$R^{T1}$

The group $R^{T1}$ is preferably selected from the group $R^{T1}$-G1 consisting of H, $C_{1-6}$-alkyl, $C_{3-6}$-cycloalkyl, $C_{3-6}$-cycloalkyl-$C_{1-3}$-alkyl, phenyl and pyridyl, wherein each cycloalkyl may be optionally substituted with one or more $C_{1-4}$-alkyl, and wherein each alkyl and cycloalkyl may be optionally substituted with one or more substituents selected from F, and
wherein each alkyl and cycloalkyl may be optionally substituted with a substituent selected from OH, $C_{1-3}$-alkyl-O—, $C_{1-3}$-alkyl-C(=O)—, HO—C(=O)— and $C_{1-4}$-alkyl-O—C(=O)—; and
wherein each phenyl and pyridyl group may be optionally substituted with one or more substituents $R^2$.

$R^{T1}$-G2:

In another embodiment the group $R^{T1}$ is selected from the group $R^{T1}$-G2 consisting of:
H, $C_{1-4}$-alkyl, phenyl and pyridinyl.

In another embodiment the group $R^{T1}$ is selected from the group $R^{T1}$-G3 consisting of H, methyl and ethyl.

$R^{T2}$ $R^{T2}$-G1:

The group $R^{T2}$ is preferably selected from the group $R^{T2}$-G1 consisting of H and $C_{1-4}$-alkyl.

$R^{T2}$-G2:

In another embodiment the group $R^{T2}$ is selected from the group $R^{T2}$-G2 consisting of H and methyl.

Examples of preferred subgeneric embodiments according to the present invention are set forth in the following table, wherein each substituent group of each embodiment is defined according to the definitions set forth hereinbefore and wherein all other substituents of the formula (I) are defined according to the definitions set forth hereinbefore:

| Embodiment | $Ar^1$ and $R^1$ | $Ar^2$ | L | X | R | T |
|---|---|---|---|---|---|---|
| E-1 | $Ar^1$-G1, $R^1$-G1 | $Ar^2$-G1 | L-G1 | X-G1 | R-G1 | T-G1 |
| E-2 | $Ar^1$-G2, $R^1$-G1 | $Ar^2$-G2 | L-G1 | X-G1 | R-G1 | T-G2 |
| E-3 | $Ar^1$-G2, $R^1$-G2 | $Ar^2$-G3 | L-G1 | X-G1 | R-G1 | T-G3 |
| E-4 | $Ar^1$-G3, $R^1$-G2 | $Ar^2$-G3a | L-G1 | X-G1 | R-G2 | T-G3 |
| E-5 | $Ar^1$-G4, $R^1$-G3 | $Ar^2$-G3 | L-G1 | X-G1 | R-G2 | T-G3 |
| E-6 | $Ar^1$-G4, $R^1$-G3 | $Ar^2$-G3a | L-G2 | X-G1 | R-G2 | T-G3 |
| E-7 | $Ar^1$-G4, $R^1$-G3 | $Ar^2$-G4 | L-G3 | X-G2 | R-G3 | T-G4 |
| E-8 | $Ar^1$-G4, $R^1$-G3 | $Ar^2$-G4 | L-G3 | X-G2 | R-G3 | T-G5 |
| E-9 | $Ar^1$-G4, $R^1$-G3 | $Ar^2$-G4 | L-G3 | X-G2 | R-G3 | T-G5a |
| E-10 | $Ar^1$-G4, $R^1$-G3 | $Ar^2$-G4 | L-G3 | X-G2 | R-G3 | T-G6 |
| E-11 | $Ar^1$-G4, $R^1$-G3 | $Ar^2$-G4 | L-G3 | X-G2 | R-G3 | T-G6a |
| E-12 | $Ar^1$-G4, $R^1$-G4 | $Ar^2$-G4a | L-G4 | X-G2 | R-G3 | T-G5 |
| E-13 | $Ar^1$-G4, $R^1$-G4 | $Ar^2$-G4a | L-G4 | X-G2 | R-G3 | T-G5a |
| E-14 | $Ar^1$-G4, $R^1$-G4 | $Ar^2$-G4a | L-G4 | X-G2 | R-G3 | T-G6 |
| E-15 | $Ar^1$-G4, $R^1$-G4 | $Ar^2$-G4a | L-G4 | X-G2 | R-G3 | T-G6a |
| E-16 | $Ar^1$-G5, $R^1$-G4 | $Ar^2$-G4 | L-G3 | X-G2 | R-G2 | T-G5 |
| E-17 | $Ar^1$-G5, $R^1$-G4 | $Ar^2$-G4a | L-G5 | X-G2 | R-G2 | T-G5 |
| E-18 | $Ar^1$-G5, $R^1$-G4 | $Ar^2$-G4a | L-G6 | X-G2 | R-G2 | T-G6a |
| E-19 | $Ar^1$-G5, $R^1$-G4 | $Ar^2$-G5 | L-G3 | X-G2 | R-G2 | T-G4 |
| E-20 | $Ar^1$-G5, $R^1$-G4 | $Ar^2$-G5 | L-G4 | X-G2 | R-G2 | T-G5 |
| E-21 | $Ar^1$-G5, $R^1$-G4 | $Ar^2$-G5 | L-G6 | X-G2 | R-G2 | T-G5 |
| E-22 | $Ar^1$-G5, $R^1$-G4 | $Ar^2$-G5 | L-G5 | X-G2 | R-G2 | T-G5 |
| E-23 | $Ar^1$-G6 | $Ar^2$-G4 | L-G2 | X-G2 | R-G2 | T-G3 |
| E-24 | $Ar^1$-G6 | $Ar^2$-G4 | L-G3 | X-G2 | R-G2 | T-G4 |
| E-25 | $Ar^1$-G6 | $Ar^2$-G4 | L-G5 | X-G2 | R-G2 | T-G4 |
| E-26 | $Ar^1$-G6 | $Ar^2$-G4a | L-G2 | X-G2 | R-G2 | T-G3 |
| E-27 | $Ar^1$-G6 | $Ar^2$-G4a | L-G3 | X-G2 | R-G2 | T-G4 |
| E-28 | $Ar^1$-G6 | $Ar^2$-G4a | L-G3 | X-G2 | R-G2 | T-G5 |
| E-29 | $Ar^1$-G6 | $Ar^2$-G4a | L-G5 | X-G2 | R-G2 | T-G5 |
| E-30 | $Ar^1$-G6 | $Ar^2$-G5 | L-G2 | X-G2 | R-G2 | T-G3 |
| E-31 | $Ar^1$-G6 | $Ar^2$-G5 | L-G3 | X-G2 | R-G2 | T-G4 |
| E-32 | $Ar^1$-G6 | $Ar^2$-G5 | L-G3 | X-G2 | R-G2 | T-G5 |
| E-33 | $Ar^1$-G6 | $Ar^2$-G5 | L-G5 | X-G2 | R-G2 | T-G5 |
| E-34 | $Ar^1$-G6a | $Ar^2$-G4 | L-G2 | X-G2 | R-G2 | T-G3 |
| E-35 | $Ar^1$-G6a | $Ar^2$-G4a | L-G3 | X-G2 | R-G2 | T-G4 |
| E-36 | $Ar^1$-G6a | $Ar^2$-G4a | L-G5 | X-G2 | R-G2 | T-G4 |
| E-37 | $Ar^1$-G6a | $Ar^2$-G5 | L-G3 | X-G2 | R-G2 | T-G4 |
| E-38 | $Ar^1$-G6a | $Ar^2$-G5 | L-G5 | X-G2 | R-G2 | T-G4 |
| E-39 | $Ar^1$-G6a | $Ar^2$-G5 | L-G6 | X-G2 | R-G2 | T-G4 |

The following preferred embodiments of compounds of the formula (I) are described using generic formulas (I.1) to (I.8b), wherein any tautomers and stereoisomers, solvates, hydrates and salts thereof, in particular the pharmaceutically acceptable salts thereof, are encompassed.

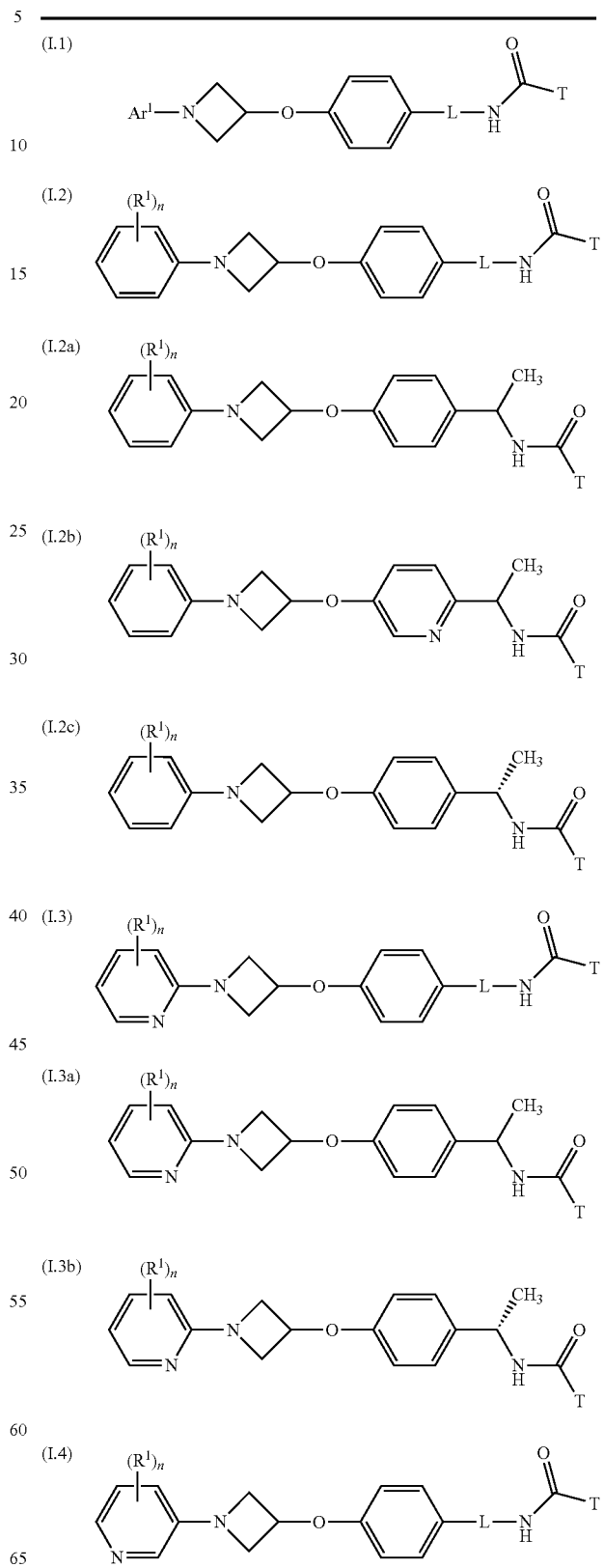

-continued (I.4a) 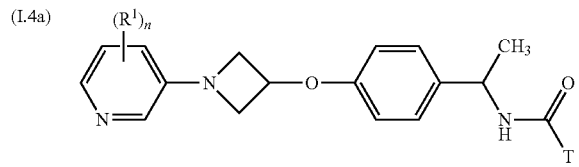

(I.4b) 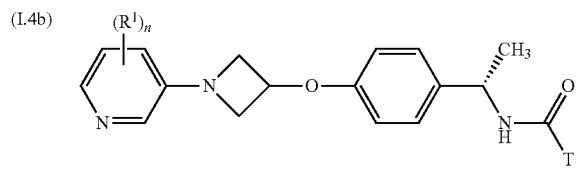

(I.5) 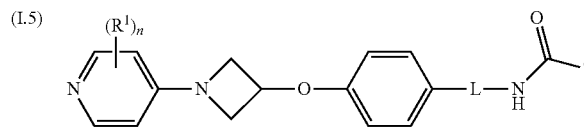

(I.5a) 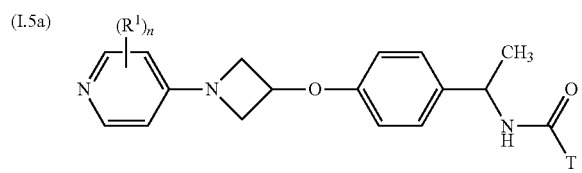

(I.5b) 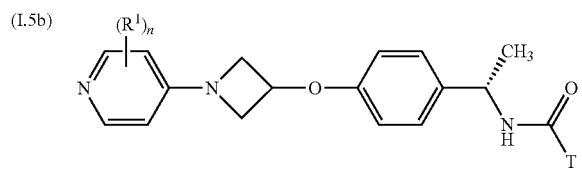

(I.6) 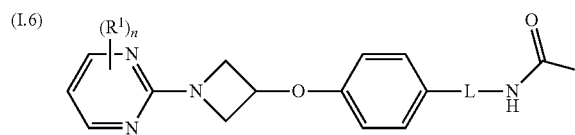

(I.6a) 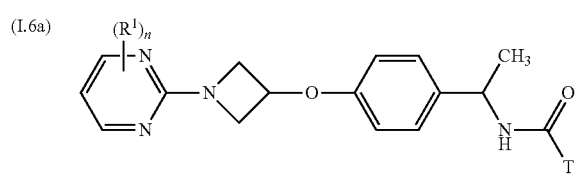

(I.6b) 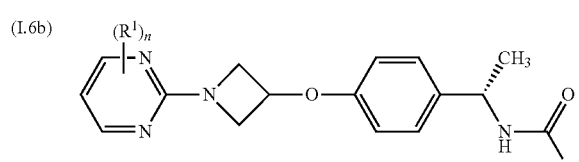

(I.7) 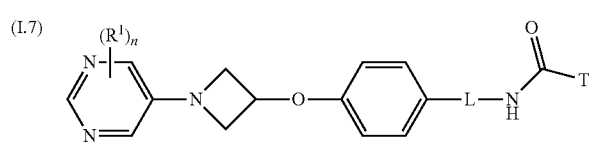

(I.7a) 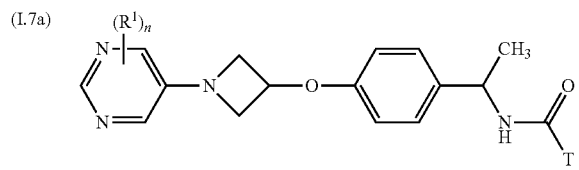

-continued (I.7b) 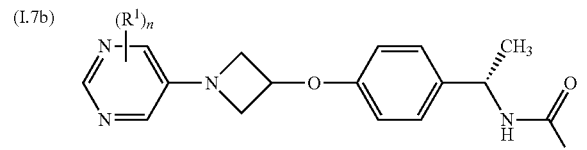

(I.8) 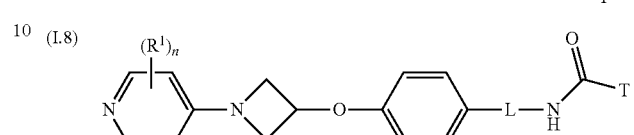

(I.8a) 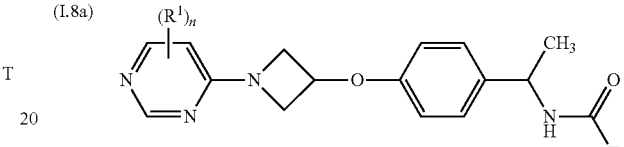

(I.8b) 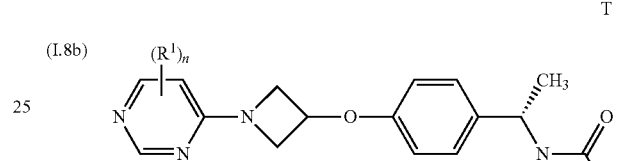

wherein in each of the above formulas (I.1) to (I.8b) the groups $Ar^1$, $R^1$, L and T are defined as hereinbefore and hereinafter; and
n is 0, 1, 2 or 3.

Preferred embodiments of the above formulas (I.1) to (I.8b) according to the present invention are set forth in the following table, wherein each group $Ar^1$, $R^1$, L and T of each embodiment is defined according to the definitions set forth hereinbefore and wherein all other substituents of the formula (I) are defined according to the definitions set forth hereinbefore and n is 0, 1, 2 or 3:

| Embodiment | Formula | $Ar^1$ | $R^1$ | n | L | T |
|---|---|---|---|---|---|---|
| E-A | (I.1) | $Ar^1$-G4 | $R^1$-G3 | 1, 2 or 3 | L-G2 | T-G3 |
| E-Aa | (I.1) | $Ar^1$-G4 | $R^1$-G4 | 1 or 2 | L-G3 | T-G5 |
| E-Ab | (I.1) | $Ar^1$-G5 | $R^1$-G3 | 1, 2 or 3 | L-G3 | T-G4 |
| E-B | (I.2) | — | $R^1$-G3 | 1, 2 or 3 | L-G3 | T-G3 |
| E-Ba | (I.2) | — | $R^1$-G3 | 1 or 2 | L-G5 | T-G5 |
| E-Bb | (I.2) | — | $R^1$-G4 | 1, 2 or 3 | L-G3 | T-G3 |
| E-Bc | (I.2) | — | $R^1$-G4 | 1, 2 or 3 | L-G3 | T-G5 |
| E-Bd | (I.2) | — | $R^1$-G4 | 1 or 2 | L-G3 | T-G4 |
| E-Be | (I.2) | — | $R^1$-G4 | 1 or 2 | L-G3 | T-G5 |
| E-Bf | (I.2) | — | $R^1$-G4 | 1 or 2 | L-G3 | T-G5a |
| E-Bg | (I.2) | — | $R^1$-G4 | 1 or 2 | L-G3 | T-G6 |
| E-Bh | (I.2) | — | $R^1$-G4 | 1 | L-G3 | T-G4 |
| E-Bi | (I.2) | — | $R^1$-G5 | 1 | L-G3 | T-G5 |
| E-Bj | (I.2) | — | $R^1$-G5 | 1 | L-G3 | T-G5a |
| E-Bk | (I.2) | — | $R^1$-G5 | 1 | L-G3 | T-G6 |
| E-C | (I.2a) | — | $R^1$-G3 | 1, 2 or 3 | — | T-G4 |
| E-Ca | (I.2a) | — | $R^1$-G3 | 1, 2 or 3 | — | T-G5 |
| E-Cb | (I.2a) | — | $R^1$-G4 | 1, 2 or 3 | — | T-G4 |
| E-Cc | (I.2a) | — | $R^1$-G4 | 1 or 2 | — | T-G5 |
| E-Cd | (I.2a) | — | $R^1$-G5 | 1 or 2 | — | T-G4 |
| E-D | (I.2a) | — | $R^1$-G5 | 1 or 2 | — | T-G5 |
| E-Da | (I.2b) | — | $R^1$-G4 | 1, 2 or 3 | — | T-G4 |
| E-Db | (I.2b) | — | $R^1$-G5 | 1 or 2 | — | T-G5 |
| E-E | (I.3) | — | $R^1$-G3 | 1 or 2 | L-G3 | T-G3 |
| E-Ea | (I.3) | — | $R^1$-G4 | 1 or 2 | L-G3 | T-G4 |
| E-Eb | (I.3) | — | $R^1$-G5a | 1 | L-G3 | T-G5 |

-continued

| Embodiment | Formula | Ar¹ | R¹ | n | L | T |
|---|---|---|---|---|---|---|
| E-F | (I.3a) | — | R¹-G3 | 1 or 2 | — | T-G4 |
| E-Fa | (I.3a) | — | R¹-G4 | 1 or 2 | — | T-G4 |
| E-Fb | (I.3a) | — | R¹-G4 | 1 or 2 | — | T-G5 |
| E-Fc | (I.3a) | — | R¹-G5a | 1 or 2 | — | T-G4 |
| E-Fd | (I.3a) | — | R¹-G5a | 1 or 2 | — | T-G5 |
| E-G | (I.3b) | — | R¹-G3 | 1 | — | T-G4 |
| E-Ga | (I.3b) | — | R¹-G4 | 1 | — | T-G4 |
| E-Gb | (I.3b) | — | R¹-G4 | 1 | — | T-G5 |
| E-Gc | (I.3b) | — | R¹-G5a | 1 | — | T-G4 |
| E-Gd | (I.3b) | — | R¹-G5a | 1 | — | T-G5 |
| E-H | (I.4) | — | R¹-G3 | 1 or 2 | L-G3 | T-G3 |
| E-Ha | (I.4) | — | R¹-G4 | 1 or 2 | L-G3 | T-G4 |
| E-Hb | (I.4) | — | R¹-G5a | 1 | L-G3 | T-G5 |
| E-I | (I.4a) | — | R¹-G3 | 1 or 2 | — | T-G4 |
| E-Ia | (I.4a) | — | R¹-G4 | 1 or 2 | — | T-G4 |
| E-Ib | (I.4a) | — | R¹-G4 | 1 or 2 | — | T-G5 |
| E-Ic | (I.4a) | — | R¹-G5a | 1 or 2 | — | T-G4 |
| E-Id | (I.4a) | — | R¹-G5a | 1 or 2 | — | T-G5 |
| E-J | (I.4b) | — | R¹-G3 | 1 | — | T-G4 |
| E-Ja | (I.4b) | — | R¹-G4 | 1 | — | T-G4 |
| E-Jb | (I.4b) | — | R¹-G4 | 1 | — | T-G5 |
| E-Jc | (I.4b) | — | R¹-G5a | 1 | — | T-G4 |
| E-Jd | (I.4b) | — | R¹-G5a | 1 | — | T-G5 |
| E-K | (I.5) | — | R¹-G3 | 1 or 2 | L-G3 | T-G3 |
| E-Ka | (I.5) | — | R¹-G4 | 1 or 2 | L-G3 | T-G4 |
| E-Kb | (I.5) | — | R¹-G5a | 1 | L-G3 | T-G5 |
| E-L | (I.5a) | — | R¹-G3 | 1 or 2 | — | T-G4 |
| E-La | (I.5a) | — | R¹-G4 | 1 or 2 | — | T-G4 |
| E-Lb | (I.5a) | — | R¹-G4 | 1 or 2 | — | T-G5 |
| E-Lc | (I.5a) | — | R¹-G5a | 1 or 2 | — | T-G4 |
| E-Ld | (I.5a) | — | R¹-G5a | 1 or 2 | — | T-G5 |
| E-M | (I.5b) | — | R¹-G3 | 1 | — | T-G4 |
| E-Ma | (I.5b) | — | R¹-G4 | 1 | — | T-G4 |
| E-Mb | (I.5b) | — | R¹-G4 | 1 | — | T-G5 |
| E-Mc | (I.5b) | — | R¹-G5a | 1 | — | T-G4 |
| E-Md | (I.5b) | — | R¹-G5a | 1 | — | T-G5 |
| E-N | (I.6) | — | R¹-G3 | 1 or 2 | L-G3 | T-G3 |
| E-Na | (I.6) | — | R¹-G4 | 1 | L-G3 | T-G4 |
| E-Nb | (I.6) | — | R¹-G5b | 1 | L-G3 | T-G5 |
| E-O | (I.6a) | — | R¹-G3 | 1 or 2 | — | T-G4 |
| E-Oa | (I.6a) | — | R¹-G4 | 1 | — | T-G4 |
| E-Ob | (I.6a) | — | R¹-G4 | 1 | — | T-G5 |
| E-Oc | (I.6a) | — | R¹-G5b | 1 | — | T-G4 |
| E-Od | (I.6a) | — | R¹-G5b | 1 | — | T-G5 |
| E-P | (I.6b) | — | R¹-G3 | 1 | — | T-G4 |
| E-Pa | (I.6b) | — | R¹-G4 | 1 | — | T-G4 |
| E-Pb | (I.6b) | — | R¹-G4 | 1 | — | T-G5 |
| E-Pc | (I.6b) | — | R¹-G5b | 1 | — | T-G4 |
| E-Pd | (I.6b) | — | R¹-G5b | 1 | — | T-G5 |
| E-Q | (I.7) | — | R¹-G3 | 1 or 2 | L-G3 | T-G3 |
| E-Qa | (I.7) | — | R¹-G4 | 1 | L-G3 | T-G4 |
| E-Qb | (I.7) | — | R¹-G5c | 1 | L-G3 | T-G5 |
| E-R | (I.7a) | — | R¹-G3 | 1 or 2 | — | T-G4 |
| E-Ra | (I.7a) | — | R¹-G4 | 1 | — | T-G4 |
| E-Rb | (I.7a) | — | R¹-G4 | 1 | — | T-G5 |
| E-Rc | (I.7a) | — | R¹-G5c | 1 | — | T-G4 |
| E-Rd | (I.7a) | — | R¹-G5c | 1 | — | T-G5 |
| E-S | (I.7b) | — | R¹-G3 | 1 | — | T-G4 |
| E-Sa | (I.7b) | — | R¹-G4 | 1 | — | T-G4 |
| E-Sb | (I.7b) | — | R¹-G4 | 1 | — | T-G5 |
| E-Sc | (I.7b) | — | R¹-G5c | 1 | — | T-G4 |
| E-Sd | (I.7b) | — | R¹-G5c | 1 | — | T-G5 |
| E-T | (I.8) | — | R¹-G3 | 1 or 2 | L-G3 | T-G3 |
| E-Ta | (I.8) | — | R¹-G4 | 1 | L-G3 | T-G4 |
| E-Tb | (I.8) | — | R¹-G5d | 1 | L-G3 | T-G5 |
| E-U | (I.8a) | — | R¹-G3 | 1 or 2 | — | T-G4 |
| E-Ua | (I.8a) | — | R¹-G4 | 1 | — | T-G4 |
| E-Ub | (I.8a) | — | R¹-G4 | 1 | — | T-G5 |
| E-Uc | (I.8a) | — | R¹-G5d | 1 | — | T-G4 |
| E-Ud | (I.8a) | — | R¹-G5d | 1 | — | T-G5 |
| E-V | (I.8b) | — | R¹-G3 | 1 | — | T-G4 |
| E-Va | (I.8b) | — | R¹-G4 | 1 | — | T-G4 |
| E-Vb | (I.8b) | — | R¹-G4 | 1 | — | T-G5 |
| E-Vc | (I.8b) | — | R¹-G5d | 1 | — | T-G4 |
| E-Vd | (I.8b) | — | R¹-G5d | 1 | — | T-G5 | including any tautomers and stereoisomers, solvates, hydrates and salts thereof, in particular the pharmaceutically acceptable salts thereof.

Preferred are those compounds of formula (I), wherein

Ar¹ is selected from the group consisting of phenyl, pyridinyl and pyrimidinyl,
  wherein the above-mentioned phenyl and pyridinyl groups are each substituted with one to three groups independently selected from R¹, and
  wherein the above-mentioned pyrimidinyl groups is substituted with one or two R¹, and
  wherein two adjacent carbon atoms of a phenyl group may be linked to each other via a —O—CH$_2$—CH$_2$—O—, —O—CH$_2$—CH$_2$—CH$_2$—C(CH$_3$)$_2$—, —O—CH$_2$—CH$_2$—CH$_2$—O—, or —O—CH$_2$—C(CH$_3$)$_2$—CH$_2$—O— bridge;

R¹ is selected from the group consisting of F, Cl, Br, CN, CF$_3$, C$_{1-4}$ alkyl, —O—C$_{1-4}$ alkyl, cyclopropyl, —O—C$_{3-5}$ cycloalkyl, —O—CH$_2$—cyclopropyl, and

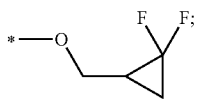

Ar² is phenylene;
L is a linear C$_{1-2}$-alkylene group that is optionally substituted with one CH$_3$,
X is O;
R is H; and
T is selected from the group consisting of: C$_{1-4}$-alkyl, C$_{2-4}$-alkenyl, C$_{3-5}$-cycloalkyl, C$_{5-6}$-cycloalkenyl, cyclopropyl-CH$_2$—, CH$_3$O—, R$^{T1}$R$^{T2}$—N—, CH$_3$—C(=O)—NH—C$_{1-3}$-alkyl, heterocyclyl, phenyl and heteroaryl,
  wherein R$^{T1}$ is H, CH$_3$ or CH$_2$CH$_3$; and
  R$^{T2}$ is H or CH$_3$; and
  wherein each alkyl, cycloalkyl and heterocyclyl may be optionally substituted with one F, CN, CH$_3$, CF$_3$, cyclopropyl, —N(CH$_3$)$_2$, pyridinyl, OH or —OCH$_3$; and
  wherein heterocyclyl is selected from the group consisting of:

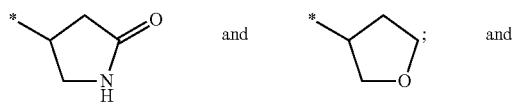

wherein heteroaryl is selected from the group consisting of pyridyl, pyrimidinyl, pyridazinyl, furanyl, pyrazolyl, oxazolyl, isoxazolyl, thiazolyl and isothiazolyl; and
  wherein each phenyl and heteroaryl group may be optionally substituted with one or two substituents independently selected from CH$_3$, —NH—CO—CH$_3$, —NH—CO—CH$_2$—OH;

including any tautomers and stereoisomers thereof, or a salt thereof.

Particularly preferred compounds, including their tautomers and stereoisomers, the salts thereof, or any solvates or hydrates thereof, are described in the experimental section hereinafter.

Specifically mentioned are the following compounds of the invention:

-continued

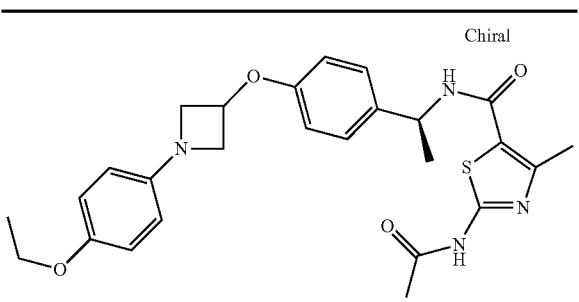

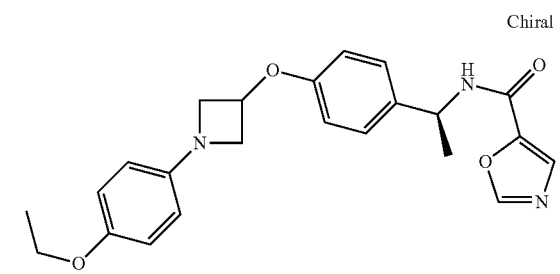 [SMILES: CCOc1ccc(N2CC(Oc3ccc([C@H](C)NC(=O)c4cnco4)cc3)C2)cc1]

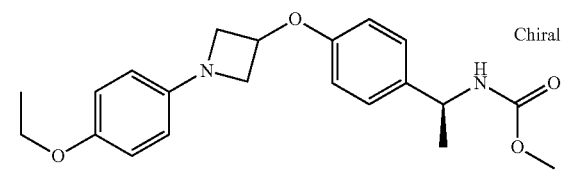 [SMILES: CCOc1ccc(N2CC(Oc3ccc([C@H](C)NC(=O)OC)cc3)C2)cc1]

and their pharmaceutically acceptable salts.

The compounds according to the invention may be obtained using methods of synthesis which are known to the one skilled in the art and described in the literature of organic synthesis. Preferably the compounds are obtained analogously to the methods of preparation explained more fully hereinafter, in particular as described in the experimental section.

Synthesis Schemes

Compounds of general formula (I) may be prepared by palladium-mediated Buchwald reactions or copper-mediated Ullmann reactions of aryl halogenides or aryl triflates (II) with azetidines (III) wherein Z is a leaving group which for example denotes Cl, Br, I or OTf (triflate).

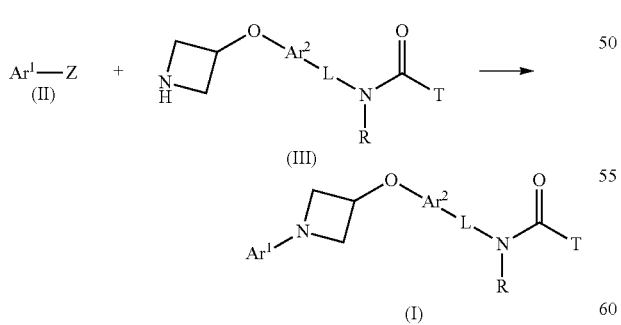

Compounds of general formula (I) may alternatively be prepared by nucleophilic aromatic substitution reactions ($S_NAr$) of aryl/heteroaryl halogenides or aryl/heteroaryl triflates (II) with azetidines (III), wherein Z is a leaving group which for example denotes Cl, Br, I, S(=O)CH$_3$ or triflate.

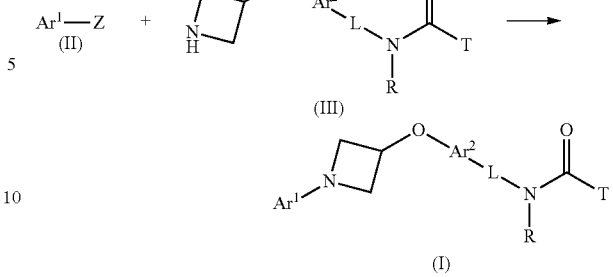

Compounds of general formula (I) may be prepared by amide coupling reactions of amines (IV) with carboxylic acids (V-I) mediated by coupling reagents such as eg 2-(1H-benzotriazol-1-yl)-1,1,3,3-tetramethyluronium tetrafluoroborat (TBTU), N-hydroxybenzotriazole (HOBt), 2-(1H-7-azabenzotriazol-1-yl)-1,1,3,3-tetramethyl-uronium hexafluorophosphate (HATU) or N,N-carbonyldiimidazole (CDI).

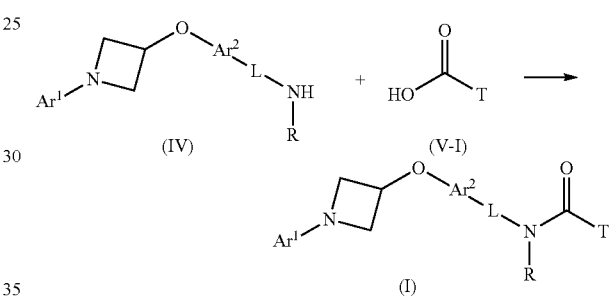

Alternatively, compounds of general formula (I) may be prepared by amide coupling reactions of amines (IV) with carboxylic acids chlorides (V-II) or carboxylic acid anhydrides (V-III).

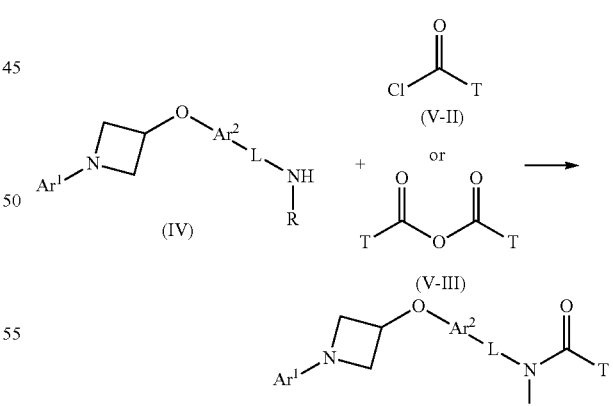

Compounds of general formula (VI) may be prepared by nucleophilic aromatic substitution reactions ($S_NAr$) of pyrimidines (VII) with nucleophiles HR$^1$ (VIII), wherein Z is a leaving group which for example denotes Cl, Br, I, S(=O) CH$_3$ or triflate and wherein HR$^1$ is a nucleophile, such as for example an alcohol or an amine and wherein the reaction may be performed with other regioisomers of pyrimidine or other heteroaryls also. Alcohols may be deprotonated by an appropriate base before used as nucleophiles.

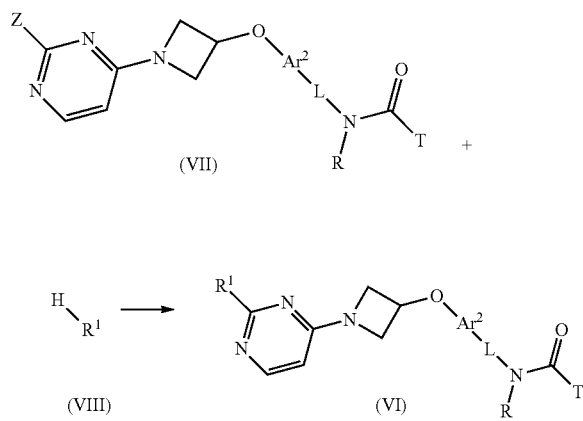

(VII)

(VIII)      (VI)

Compounds of general formula (IX) may be prepared by alkylation reactions of aromatic alcohols (X) with electrophiles (XI) wherein Z is a leaving group which for example denotes Cl, Br, I, mesylate, tosylate or triflate and $R^3$ is $C_{1-6}$-alkyl, $C_{3-6}$-alkenyl, $C_{3-6}$-alkynyl, $C_{3-10}$-carbocyclyl, $C_{3-10}$-carbocyclyl-$C_{1-3}$-alkyl, $R^{N1}R^{N2}N$—$C_{2-3}$-alkyl, heterocyclyl, heterocyclyl-$C_{1-3}$-alkyl, aryl, aryl-$C_{1-3}$-alkyl, heteroaryl or heteroaryl-$C_{1-3}$-alkyl, wherein in each carbocyclyl and heterocyclyl a $CH_2$-group may optionally be replaced by —C(=O)— or —C(=$CR^{N2}_2$)—; wherein each carbocyclyl and heterocyclyl may be optionally substituted with one or more $C_{1-4}$-alkyl, which may be optionally substituted with one or more substituents $R^C$; wherein each alkyl, carbocyclyl and heterocyclyl may be optionally substituted with one or more substituents $R^C$; wherein each heterocyclyl may be optionally substituted with aryl or heteroaryl; and wherein each aryl and heteroaryl group may be optionally substituted with one or more substituents $R^2$.

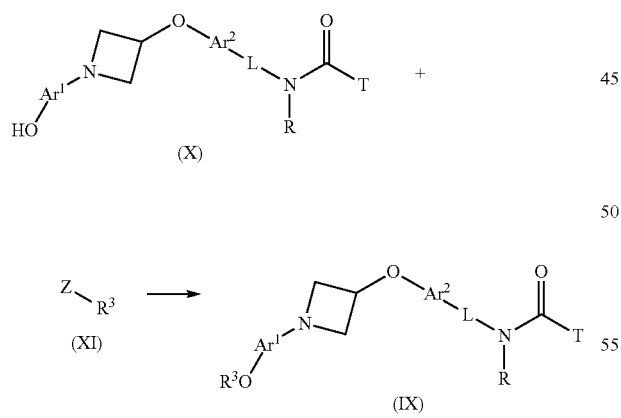

(X)

(XI)

(IX)

Compounds of general formula (XII) may be prepared by palladium-catalyzed Suzuki coupling reactions of aryl/heteroaryl halogenides or aryl/heteroaryl triflates (XIII) with boronic acids (XIV) or trimethylboroxine wherein Z is a leaving group which for example denotes Cl, Br, I or triflate and $R^5$ is $C_{2-6}$-alkenyl, $C_{2-6}$-alkynyl, aryl or heteroaryl, wherein each aryl and heteroaryl group may be optionally substituted with one or more substituents $R^2$.

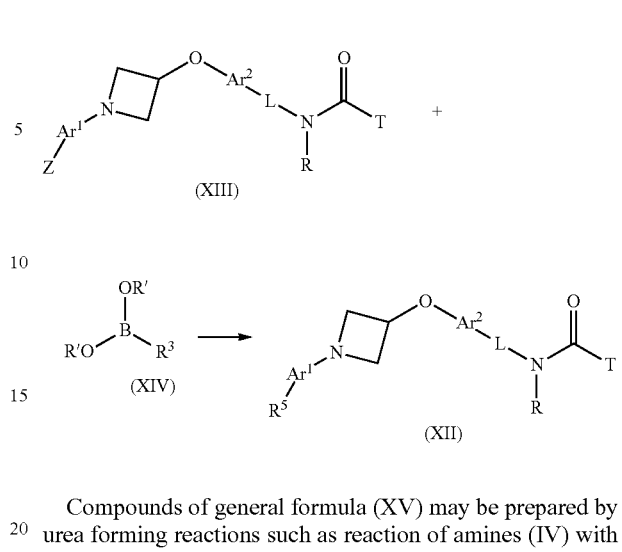

(XIII)

(XIV)

(XII)

Compounds of general formula (XV) may be prepared by urea forming reactions such as reaction of amines (IV) with amines (XVI) after reaction with reagents such as N,N-carbonylditriazole (CDT) or N,N-carbonyldiimidazole (CD).

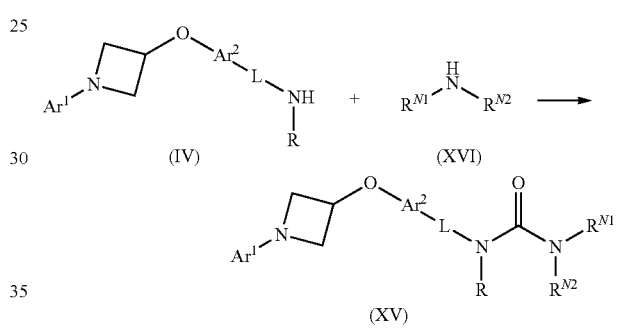

(IV)     (XVI)

(XV)

Alternatively, compounds of general formula (XV) may be prepared by urea forming reactions such as reaction of amines (IV) with carbamoyl chlorides (XVII) or isocyanates (XVIII).

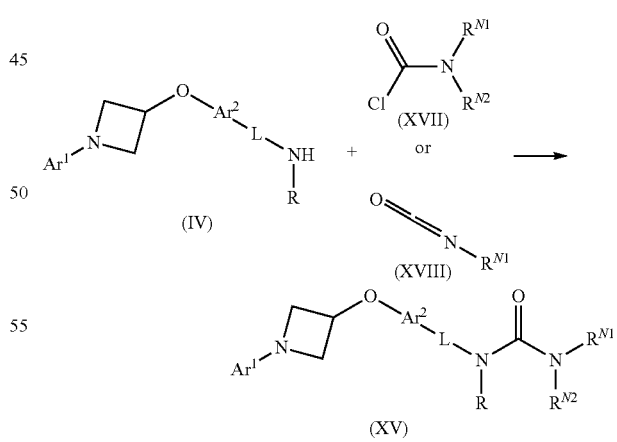

(XVII)

(IV)

(XVIII)

(XV)

Compounds of general formula (XX), wherein $R^8$ is $C_{1-6}$-alkyl, $C_{3-10}$-carbocyclyl or $C_{3-10}$-carbocyclyl-$C_{1-3}$-alkyl, may be prepared by urethane forming reactions such as reaction of amines (IV) with alcohols (IXX) after reaction with reagents such as CDT or CDI. Alcohols may be used in their deprotonated form.

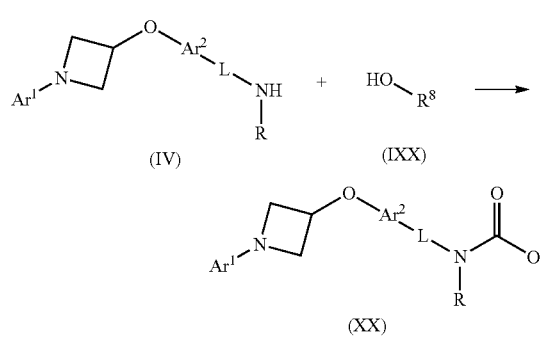

(IV)  (IXX)

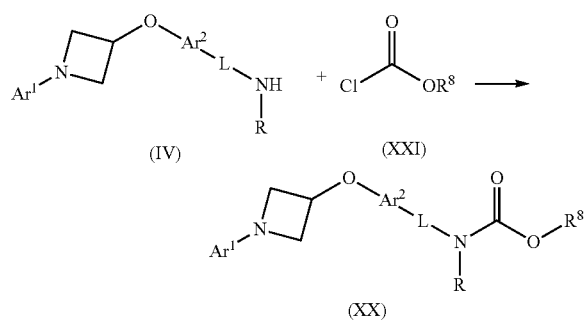

(XX)

Alternatively, compounds of general formula (XX) may be prepared by urethane forming reactions such as reaction of amines (IV) with chloro formates (XXI).

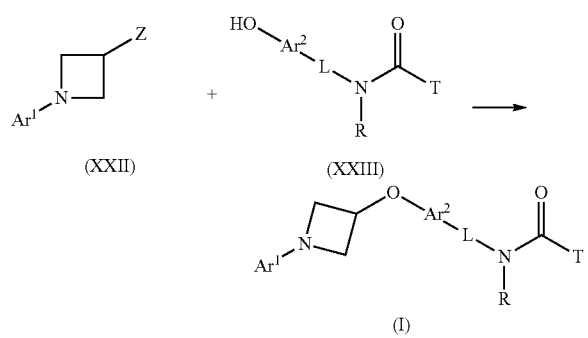

(IV)  (XXI)

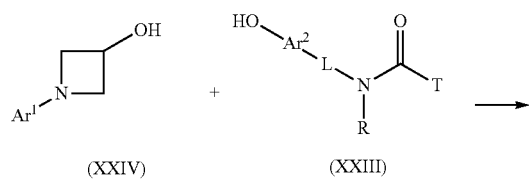

(XX)

Compounds of general formula (I) may be prepared by alkylation reactions of aromatic alcohols (XXIII) with electrophiles (XXII) wherein Z is a leaving group sucha as for example Cl, Br, I, mesylate, tosylate or triflate

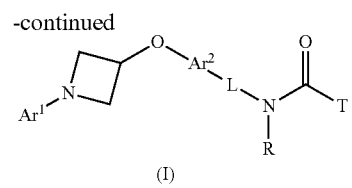

(XXII)  (XXIII)

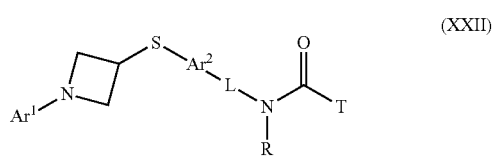

(I)

Alternatively compounds of general formula (I) may be prepared by a Mitsunobu reaction of aromatic alcohols (XXIII) with alcohols (XXIV).

(XXIV)  (XXIII)

(I)

Compounds of general formula XXII, wherein X is S, may be prepared by analoguous reactions as described before for X=O, except for the Mitsunobu reaction.

(XXII)

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of acetyl-CoA carboxylase(s) (ACC)(s) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached. For example, the term "3-carboxypropyl-group" represents the following substituent:

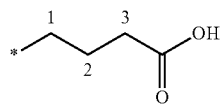 [SMILES: *CCCC(=O)O]

wherein the carboxy group is attached to the third carbon atom of the propyl group. The terms "1-methylpropyl-", "2,2-dimethylpropyl-" or "cyclopropylmethyl-" group represent the following groups:

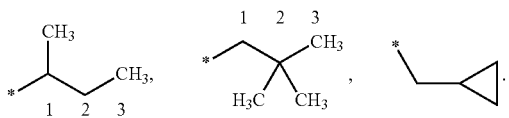

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with Lex as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention can be synthesized from the parent compound which contains a basic or acidic moiety by conventional chemical methods.

Salts of other acids than those mentioned above which for example are useful for purifying or isolating the compounds of the present invention are also part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CHCH(CH_3)_2$)— and —$C(CH_3)$($CH_2CH_3$)—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —$CH$=$CH_2$, —$CH$=$CH$—$CH_3$, —$CH_2$—$CH$=$CH_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term C$_{2-3}$-alkenylene includes —CH=CH—, —CH=CH—CH$_2$—, —CH$_2$—CH=CH—.

The term "C$_{2-n}$-alkynyl", is used for a group as defined in the definition for "C$_{1-n}$-alkyl" with at least two carbon atoms, if at least two of those carbon atoms of said group are bonded to each other by a triple bond. For example the term C$_{2-3}$-alkynyl includes —C≡CH, —C≡C—CH$_3$—, —CH$_2$—C≡CH.

The term "C$_{2-n}$-alkynylene" is used for a group as defined in the definition for "C$_{1-n}$-alkynylene" with at least two carbon atoms, if at least two of those carbon atoms of said group are bonded to each other by a triple bond. For example the term C$_{2-3}$-alkynylene includes —C≡C—, C≡C—CH$_2$—, —CH$_2$—C≡C—.

The term "C$_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term C$_{3-10}$-carbocyclyl includes C$_{3-10}$-cylcoalkyl, C$_{3-10}$-cycloalkenyl, octahydropentalenyl, octahydroindenyl, decahydronaphthyl, indanyl, tetrahydronaphthyl. Most preferably the term C$_{3-n}$-carbocyclyldenotes C$_{3-n}$-cylcoalkyl, in particular C$_{3-7}$-cycloalkyl.

The term "C$_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "C$_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term C$_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spirocyclic, perferably mono- or bicyclic-ring system containing one or more heteroatoms selected from N, O or S(O)$_r$ with r=0, 1 or 2, which in addition may have a carbonyl group. More preferably the term "heterocyclyl" as used herein, either alone or in combination with another radical, means a saturated or unsaturated, even more preferably a saturated mono- or bicyclic-ring system containing 1, 2, 3 or 4 heteroatoms selected from N, O or S(O)$_r$ with r=0, 1 or 2 which in addition may have a carbonyl group. The term "heterocyclyl is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

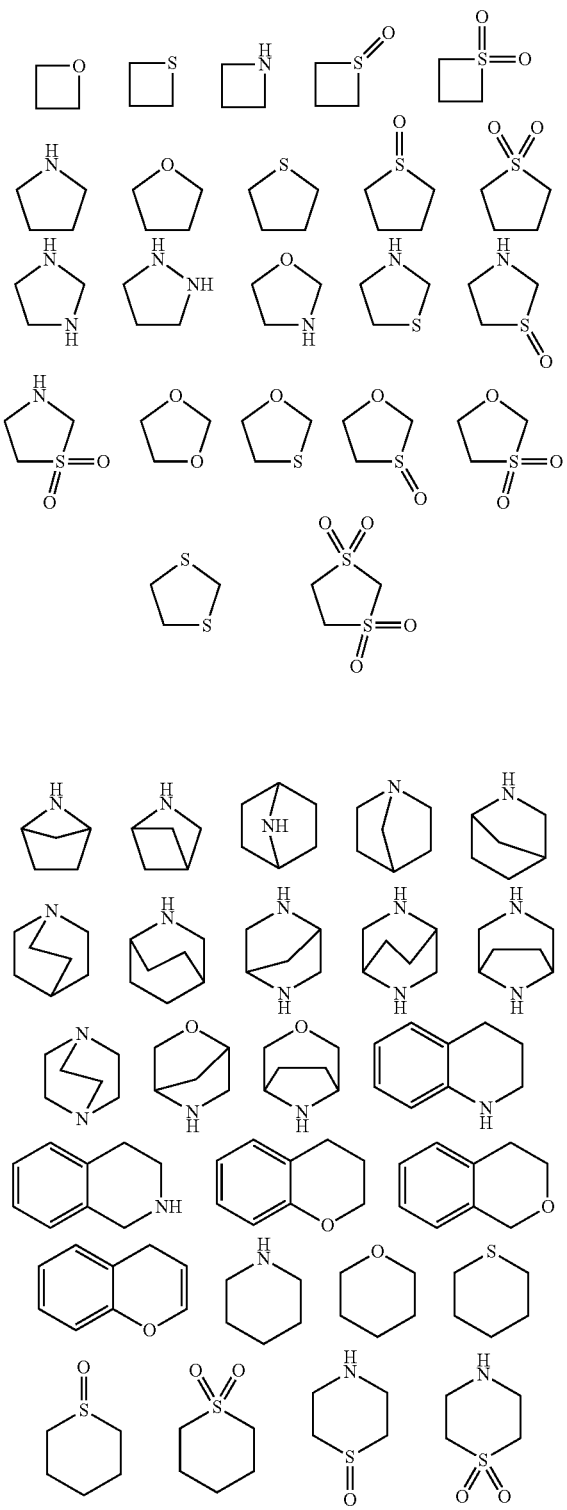

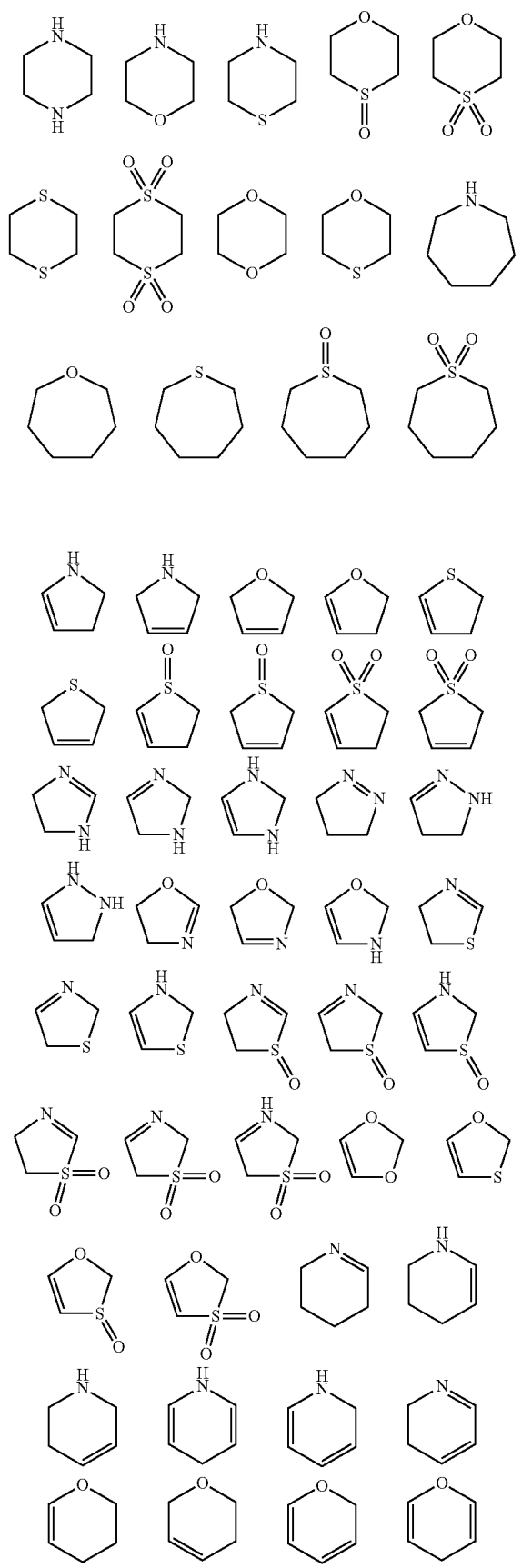
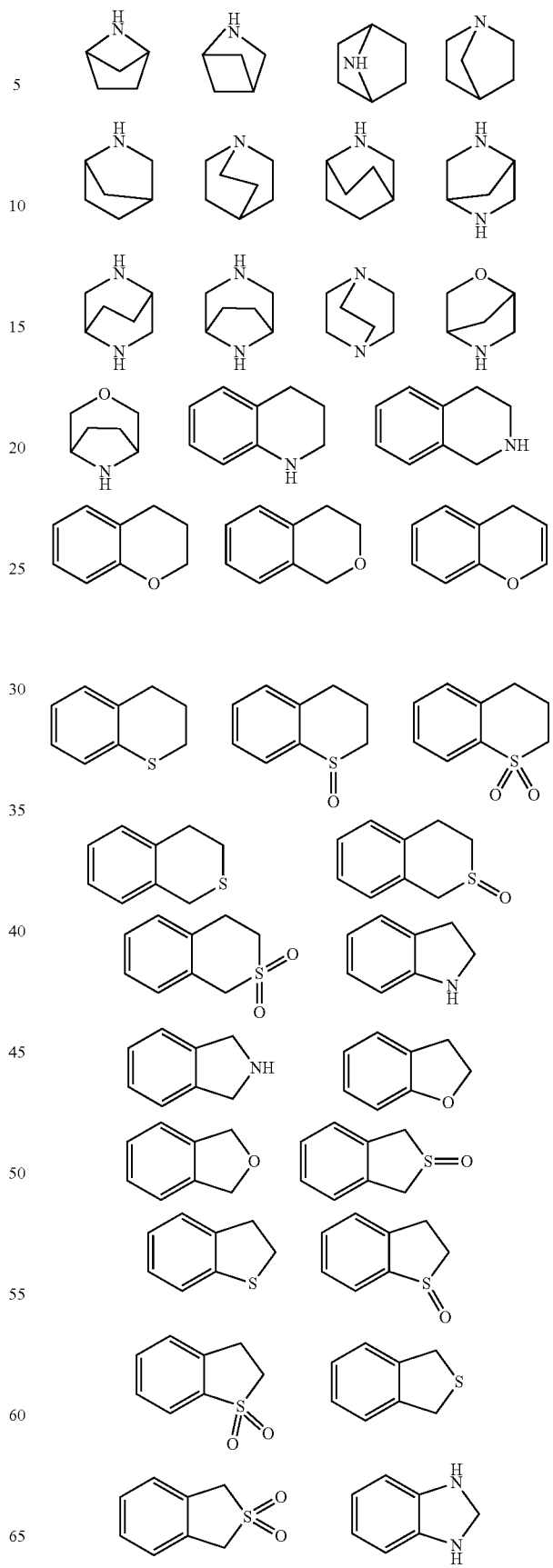

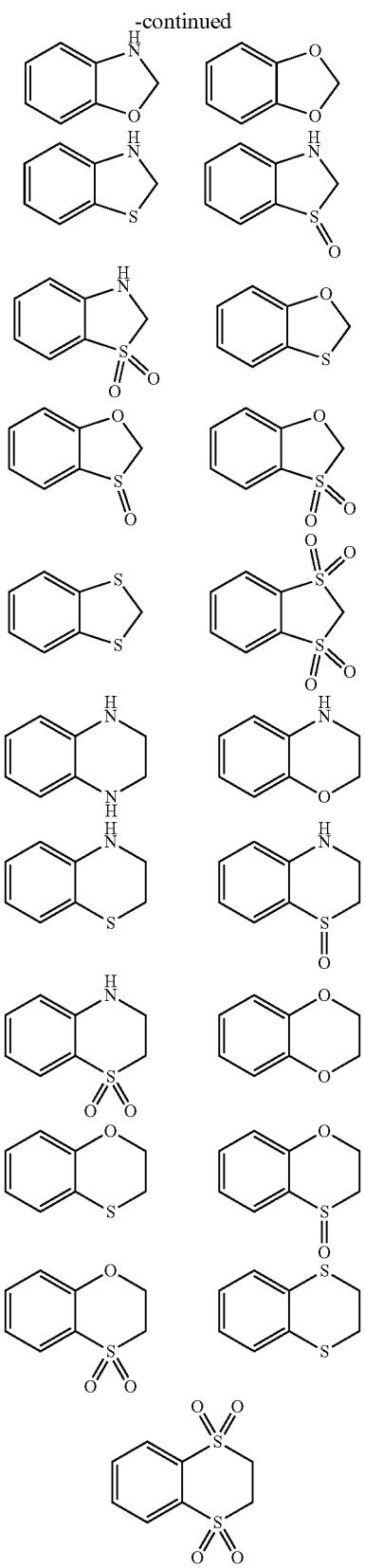

wherein at least one of the heteroatoms is part of an aromatic ring, and wherein said ring system may have a carbonyl group. More preferably the term "heteroaryl" as used herein, either alone or in combination with another radical, means a mono- or bicyclic-ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

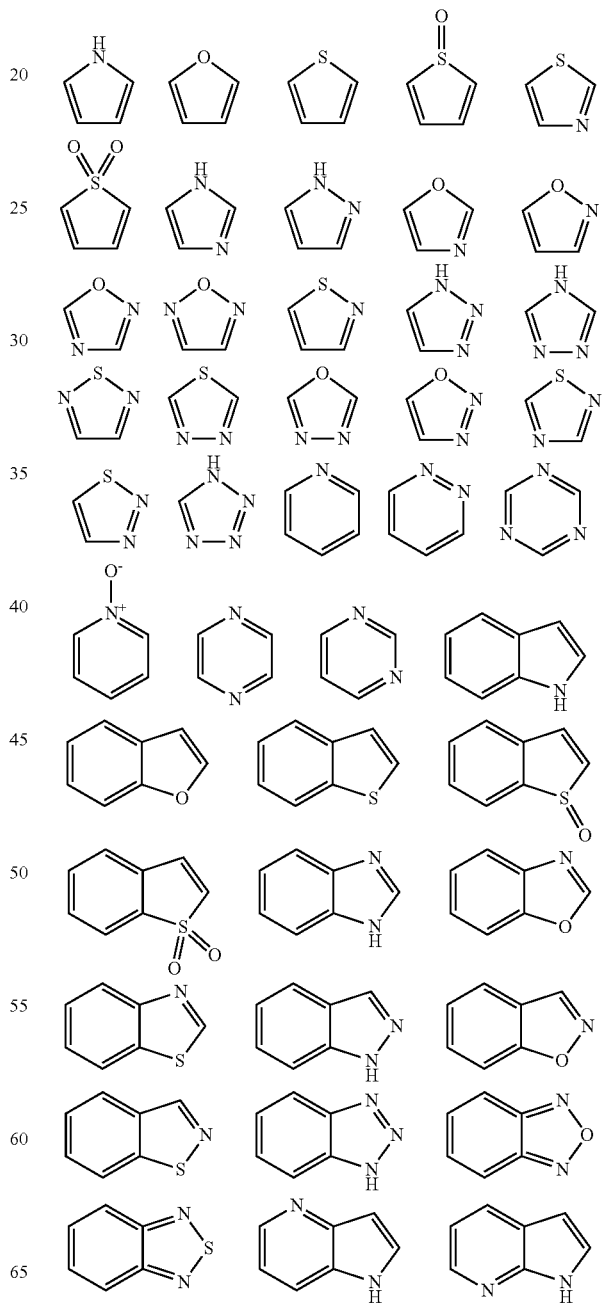

The term "heteroaryl" means a mono- or polycyclic, preferably mono- or bicyclic-ring system containing one or more heteroatoms selected from N, O or S(O)$_r$ with r=0, 1 or 2

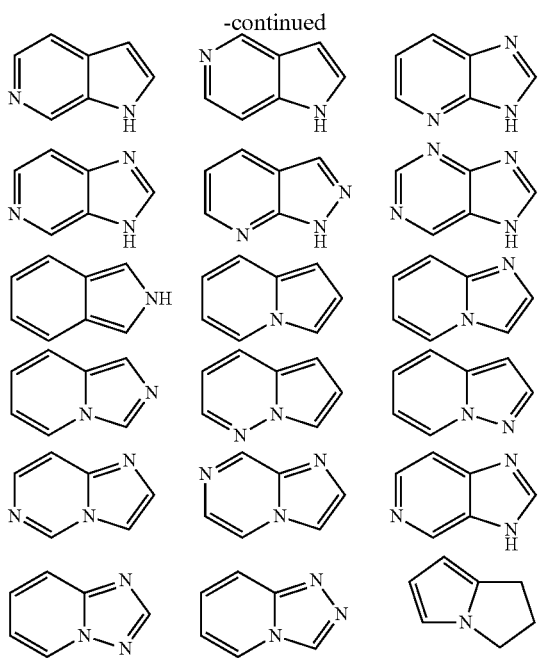

Many of the terms given above may be used repeatedly in the definition of a formula or group and in each case have one of the meanings given above, independently of one another.

Pharmacological Activity

The activity of the compounds of the invention may be demonstrated using the following ACC2 assay:

Spectrophotometric 384 Well Assay

Malonyl CoA formation by acetyl CoA carboxylases is stoichometrically linked to the consumption of ATP. ACC2 activity is measured in a NADH-linked kinetic method measuring ADP generated during the ACC reaction using a coupled lactate dehydrogenase/pyruvate kinase reaction.

For biological testing, a human ACC2 construct which lacks the 128 amino acids at the N-terminus for increased solubility (nt 385-6966 in Genbank entry AJ575592) is cloned. The protein is then expressed in insect cells using a baculoviral expression system. Protein purification is performed by anion exchange.

All compounds are dissolved in dimethyl sulfoxide (DMSO) to a concentration of 10 mM.

Assay reactions are then carried out in 384-well plates, with hACC2 in an appropriate dilution and at final assay concentrations (f.c.) of 100 mM Tris (pH 7.5), 10 mM trisodium citrate, 25 mM $KHCO_3$, 10 mM $MgCl_2$, 0.5 mg/ml BSA, 3.75 mM reduced L-glutathione, 15 U/ml lactate dehydrogenase, 0.5 mM phosphoenolpyruvate, 15 U/ml pyruvate kinase, compounds at different concentrations at final DMSO concentrations of 1%.

The enzymatic reaction is then started by addition of a mixture of NADH, acetyl Coenzyme A (both 200 µM f.c.) and ATP (500 uM f.c.). The decrease of the optical density (slope S) is then determined at 25° C. at a wavelength of 340 nm over 15 minutes in a spectrophotometric reader.

Each assay microtiter plate contains wells with vehicle instead of compound as controls for the non-inhibited enzyme (100% CTL; 'HIGH') and wells without acetyl-CoA as controls for non-specific NADH degradation (0% CTL; 'LOW').

The slope S is used for calculation of % CTL=(S(compound)−S('LOW'))/(S('HIGH')—S('LOW'))*100. Compounds will give values between 100% CTL (no inhibition) and 0% CTL (complete inhibition).

For IC50 value determination, the sample slope in the presence of the test compound after subtraction of the low controls (S(compound)−S('LOW')) are used.

An IC50 value is derived from the compound slopes at different dosages after subtraction of the low controls (S(compound)−S('LOW')) by non-linear regression curve fitting (equation $y=(A+((B-A)/(1+((C/x)^D))))$).

The compounds of general formula (I) according to the invention for example have $IC_{50}$ values below 15000 nM, particularly below 1000 nM, preferably below 300 nM.

In the following table the activity expressed as IC50 (µM) of compounds according to the invention is presented wherein the IC50 values are determined in the ACC2 assay as described hereinbefore. The term "Ex." refers to the example numbers according to the following experimental section.

| Ex. | IC50 [µM] |
| --- | --- |
| 1.1 | 0.18 |
| 1.2 | 0.24 |
| 1.3 | 0.53 |
| 1.4 | 0.13 |
| 1.5 | 0.20 |
| 1.6 | 0.08 |
| 1.7 | 1.25 |
| 1.8 | 0.55 |
| 1.9 | 0.56 |
| 1.10 | 0.67 |
| 1.11 | 2.21 |
| 1.12 | 5.34 |
| 1.13 | 0.07 |
| 1.14 | 0.07 |
| 1.15 | 0.18 |
| 1.16 | 0.45 |
| 1.17 | 1.89 |
| 1.18 | 0.14 |
| 1.19 | 0.09 |
| 1.20 | 0.49 |
| 1.21 | 0.19 |
| 1.22 | 1.18 |
| 1.23 | 2.81 |
| 1.24 | 0.12 |
| 1.25 | 0.58 |
| 1.26 | 0.74 |
| 1.27 | 1.75 |
| 1.28 | 1.62 |
| 1.29 | 0.19 |
| 1.30 | 0.67 |
| 1.31 | 0.19 |
| 1.32 | 0.19 |
| 1.33 | 0.20 |
| 1.34 | 0.34 |
| 1.35 | 0.06 |
| 1.36 | 2.83 |
| 1.37 | 2.27 |
| 1.38 | 2.31 |
| 1.39 | 0.35 |
| 1.40 | 1.03 |
| 1.41 | 1.23 |
| 1.42 | 1.05 |
| 1.43 | 1.29 |
| 1.44 | 0.25 |
| 1.45 | 0.13 |
| 1.46 | 0.17 |
| 1.47 | 0.40 |
| 1.48 | 1.02 |
| 1.49 | 1.13 |
| 1.50 | 0.89 |
| 1.51 | 0.27 |
| 1.52 | 0.09 |
| 1.53 | 0.76 |
| 1.54 | 0.04 |
| 1.55 | 0.11 |

| Ex. | IC50 [μM] |
|---|---|
| 1.56 | 0.15 |
| 1.57 | 0.74 |
| 1.58 | 1.39 |
| 1.59 | 0.30 |
| 1.60 | 0.65 |
| 1.61 | 2.54 |
| 1.62 | 2.91 |
| 2.1 | 0.88 |
| 2.2 | 0.06 |
| 2.3 | 0.24 |
| 2.4 | 6.14 |
| 2.5 | 0.17 |
| 2.6 | 0.09 |
| 2.7 | 2.06 |
| 2.8 | 4.10 |
| 2.9 | 10.63 |
| 2.10 | 0.14 |
| 2.11 | 2.55 |
| 2.12 | 4.50 |
| 3.1 | 0.21 |
| 3.2 | 1.12 |
| 3.3 | 0.32 |
| 3.4 | 1.47 |
| 3.5 | 0.20 |
| 3.6 | 3.88 |
| 3.7 | 0.47 |
| 3.8 | 0.24 |
| 3.9 | 3.82 |
| 4.1 | 0.46 |
| 4.2 | 2.04 |
| 4.3 | 0.48 |
| 4.4 | 3.99 |
| 4.5 | 2.45 |
| 4.6 | 6.23 |
| 4.7 | 3.47 |
| 4.8 | 0.24 |
| 4.9 | 0.72 |
| 4.10 | 0.37 |
| 4.11 | 3.62 |
| 4.12 | 1.06 |
| 4.13 | 0.25 |
| 4.14 | 6.11 |
| 4.15 | 0.69 |
| 4.16 | 0.47 |
| 4.17 | 0.29 |
| 4.18 | 1.80 |
| 4.19 | 0.20 |
| 4.20 | 0.77 |
| 4.21 | 0.41 |
| 4.22 | 0.45 |
| 4.23 | 1.18 |
| 4.24 | 0.39 |
| 4.25 | 0.75 |
| 4.26 | 13.34 |
| 4.27 | 0.57 |
| 4.28 | 0.36 |
| 4.29 | 1.17 |
| 4.30 | 1.38 |
| 4.31 | 0.19 |
| 4.32 | 0.10 |
| 4.33 | 1.73 |
| 4.34 | 0.94 |
| 4.35 | 1.11 |
| 4.36 | 1.14 |
| 4.37 | 0.29 |
| 4.38 | 3.05 |
| 4.39 | 0.57 |
| 4.39 | 0.60 |
| 4.40 | 1.05 |
| 4.41 | 3.48 |
| 4.42 | 0.53 |
| 4.43 | 0.53 |
| 5.1 | 0.17 |
| 5.2 | 2.18 |
| 6.1 | 0.09 |
| 6.2 | 1.74 |
| 6.3 | 0.15 |
| 7.1 | 1.44 |
| 7.2 | 1.25 |
| 7.3 | 0.78 |
| 8.1 | 7.70 |
| 8.2 | 2.37 |
| 8.3 | 1.09 |
| 8.4 | 0.43 |
| 8.5 | 0.16 |
| 8.6 | 1.77 |
| 8.7 | 0.05 |
| 8.8 | 0.43 |
| 8.9 | 1.15 |
| 8.10 | 0.37 |
| 8.11 | 2.84 |
| 8.12 | 1.00 |
| 8.13 | 0.45 |
| 8.14 | 2.25 |
| 8.15 | 1.74 |
| 8.16 | 0.70 |
| 8.17 | 2.79 |
| 8.18 | 0.74 |
| 8.19 | 0.69 |
| 8.20 | 0.48 |
| 8.21 | 0.30 |
| 8.22 | 1.87 |
| 8.23 | 5.79 |
| 8.24 | 3.94 |
| 8.25 | 0.53 |
| 8.26 | 2.78 |
| 8.27 | 0.76 |
| 8.28 | 0.17 |
| 8.29 | 0.41 |
| 8.30 | 0.67 |
| 8.31 | 1.09 |
| 8.32 | 0.55 |
| 8.33 | 0.19 |
| 8.34 | 0.81 |
| 8.35 | 3.16 |
| 8.36 | 3.04 |
| 8.37 | 2.06 |
| 8.38 | 1.26 |
| 8.39 | 5.20 |
| 8.40 | 0.35 |
| 8.41 | 0.51 |
| 8.42 | 1.69 |
| 8.43 | 2.34 |
| 8.44 | 0.93 |
| 8.45 | 2.31 |
| 8.46 | 1.19 |
| 8.47 | 1.91 |
| 9 | 1.10 |
| 10.1 | 0.34 |
| 10.2 | 1.17 |
| 10.3 | 0.67 |
| 10.4 | 0.44 |
| 10.5 | 0.48 |
| 10.6 | 0.42 |
| 10.7 | 0.23 |
| 11.1 | 6.01 |
| 11.2 | 10.60 |
| 11.3 | 11.75 |
| 11.4 | 2.39 |
| 11.5 | 3.20 |
| 11.6 | 8.28 |
| 12.1 | 4.12 |
| 12.2 | 0.70 |
| 13 | 0.10 |
| 14 | 2.04 |

In view of their ability to inhibit acetyl-CoA carboxylase(s), the compounds of general formula (I) according to the invention and the corresponding salts thereof are theoretically suitable for the treatment, including preventative treatment of all those diseases or conditions which may be affected or which are mediated by the inhibition of acetyl-CoA carboxylase(s), in particular ACC2, activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of acetyl-CoA carboxylase(s), in particular ACC2, in a patient, preferably in a human.

In yet another aspect the present invention relates a method for treating, including preventing a disease or condition mediated by the inhibition of acetyl-CoA carboxylase(s) in a mammal that includes the step of administering to a patient, preferably a human, in need of such treatment a therapeutically effective amount of a compound of the present invention, or a pharmaceutical composition thereof.

Diseases and conditions mediated by inhibitors of acetyl-CoA carboxylases embrace metabolic and/or cardiovascular and/or neurodegenerative diseases or conditions.

According to one aspect the compounds of the present invention are particularly suitable for treating diabetes mellitus, in particular Type 2 diabetes, Type 1 diabetes, and diabetes-related diseases, such as is hyperglycemia, metabolic syndrome, impaired glucose tolerance, diabetic neuropathy, diabetic nephropathy, diabetic retinopathy, dyslipidemia, hypertension, hyperinsulinemia, and insulin resistance syndrome, hepatic insulin resistance, including complications such as macro- and microvascular disorders, including thromboses, hypercoagulable and prothrombotic states (arterial and venous), high blood pressure, coronary artery disease and heart failure, increased abdominal girth, hypercoagulability, hyperuricemia, micro-albuminemia.

According to another aspect the compounds of the present invention are particularly suitable for treating overweight, obesity, including visceral (abdominal) obesity, nonalcoholic fatty liver disease (NAFLD) and obesity related disorders, such as for example weight gain or weight maintenance Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$ or greater.

According to another aspect the compounds of the present invention are particularly suitable for treating, inclduing preventing, or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia,pancreatic beta cell degeneration and diabetic complications (such as macro- and microvascular disorders, atherosclerosis, coronary heart disease, stroke, peripheral vascular disease, nephropathy, hypertension, neuropathy, and retinopathy).

In addition the compounds of the present invention are suitable for treating dyslipidemias in general and more specifically elevated lipid concentrations in the blood and in tissues, dysregulation of LDL, HDL and VLDL, in particular high plasma triglyceride concentrations, high postprandial plasma triglyceride concentrations, low HDL cholesterol concentration, low apoA lipoprotein concentrations, high LDL cholesterol concentrations, high apoB lipoprotein concentrations, including atherosclerosis, coronary heart disease, cerebrovascular disorders, diabetes mellitus, metabolic syndrome, obesity, insulin resistance and/or cardiovascular disorders.

ACC inhibition may lead to a centrally stimulating effect on food intake. Therefore compounds of the present invention may be suitable for treating eating disorders such as anorexia nervosa.

In addition the compounds of the present invention may provide neuroprotective effects in patients with Parkinson's disease, Alzheimer's disease, hypoxia, ischemia, amyotrophic lateral sclerosis or glioma and may improve cognitive scores in Alzheimer's diseases patients.

Further diseases and conditions mediated by inhibitors of acetyl-CoA carboxylases embrace but are not limited to:

A. disorders of fatty acid metabolism and glucose utilization disorders; disorders in which insulin resistance is involved;
B. hepatic disorders and conditions related thereto, including:
   fatty liver, hepatic steatosis, non-alcoholic hepatitis, non-alcoholic steatohepatitis (NASH), alcoholic hepatitis, acute fatty liver, fatty liver of pregnancy, drug-induced hepatitis, iron storage diseases, hepatic fibrosis, hepatic cirrhosis, hepatoma, viral hepatitis;
C. skin disorders and conditions and those associated with polyunsaturated fatty acids, such as
   eczema, acne, sebaceous gland diseases, psoriasis, keloid scar formation or prevention, other diseases releated to mucous membrane fatty acid composition;
D. primary hypertriglyceridemia or secondary hypertriglyceridemias following familial histiocytic reticulosis, lipoprotein lipase deficiency, hyperlipo-proteinemias, apolipoprotein deficiency (e.g. apoCII or apoE deficiency);
E. diseases or conditions related to neoplastic cellular proliferation, for example benign or malignant tumors, cancer, neoplasias, metastases, carcinogenesis;
F. diseases or conditions related to neurological, psychiatric or immune disorders or conditions;
G. other diseases or conditions in which inflammatory reactions, cell differentiation and/or other ACC-mediated aspects may for example be involved are:
   atherosclerosis such as, for example (but not restricted thereto), coronary sclerosis including angina pectoris or myocardial infarction, stroke, ischemic, stroke and transient ischemic attack (TIA),
   peripheral occlusive disease,
   vascular restenosis or reocclusion,
   chronic inflammatory bowel diseases such as, for example, Crohn's disease and ulcerative colitis,
   pancreatitis,
   sinusitis,
   retinopathy, ischemic retinopathy,
   adipose cell tumors,
   lipomatous carcinomas such as, for example, liposarcomas,
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas, breast cancer (in particular breast cancer with BRCA1 mutations), etc.,
   tumors in which ACC is up regulated,
   acute and chronic myeloproliferative disorders and lymphomas, angiogenesis
   neurodegenerative disorders including Alzheimer's disease, multiple sclerosis, Parkinson's disease, epilepsy,
   erythemato-squamous dermatoses such as, for example, psoriasis,
   acne vulgaris,
   other skin disorders and dermatological conditions which are modulated by PPAR, eczemas and neurodermatitis,
dermatitis such as, for example, seborrheic dermatitis or photodermatitis,
keratitis and keratoses such as, for example, seborrheic keratoses, senile keratoses, actinic keratoses, photo-induced keratoses or keratosis follicularis,
keloids and keloid prophylaxis,
bacterial infections,
fungal infections,
warts, including condylomata or condylomata acuminata
human papilloma viral (HPV) infections such as, for example, venereal papillomata, viral warts such as, for example, molluscum contagiosum, leukoplakia,
papular dermatoses such as, for example, lichen planus,
skin cancer such as, for example, basal-cell carcinomas, melanomas or cutaneous T-cell lymphomas,
localized benign epidermal tumors such as, for example, keratoderma, epidermal naevi,
chilblains;
high blood pressure,
polycystic ovary syndrome (PCOS),
asthma,
cystic fibrosis,
osteoarthritis,
lupus erythematosus (LE) or inflammatory rheumatic disorders such as, for example rheumatoid arthritis,
vasculitis,
wasting (cachexia),
gout,
ischemia/reperfusion syndrome,
acute respiratory distress syndrome (ARDS)
viral diseases and infections
lipodystrophy and lipodystrophic conditions, also for treating adverse drug effect;
myopathies and lipid myopathis (such as carnitine palmitoyltransferase I or II deficiency);
H. formation of muscles and a lean body or muscle mass formation.

The dose range of the compounds of general formula (I) applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent.

According to one embodiment the additional therapeutic agent is selected from the group of therapeutic agents useful in the treatment of diseases or conditions associated with metabolic diseases or conditions such as for example diabetes mellitus, obesity, diabetic complications, hypertension, hyperlipidemia.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, agents for the treatment of malignant tumors, antithrombotic agents, agents for the treatment of heart failure and agents for the treatment of complications caused by diabetes or associated with diabetes.

Suitable anti-obesity agents include 11beta-hydroxy steroid dehydrogenase-1 (11beta-HSD type 1) inhibitors, stearoyl-CoA desaturase-1 (SCD-1) inhibitor, MCR-4 agonists, cholecystokinin-A (CCK-A) agonists, monoamine reuptake inhibitors, sympathomimetic agents, beta3 adrenergic agonists, dopamine agonists, melanocyte-stimulating hormone analogs, 5HT2c agonists, melanin concentrating hormone antagonists, leptin (the OB protein), leptin analogs, leptin agonists, galanin antagonists, lipase inhibitors, anorectic agents, neuropeptide-γ antagonists (e.g., NPY Y5 antagonists), $PY_{y3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors, human agouti-related protein (AGRP) inhibitors, ghrelin antagonists, histamine 3 antagonists or inverse agonists, neuromedin U agonists, MTP/ApoB inhibitors (e.g., gut-selective MTP inhibitors), opioid antagonist, orexin antagonist, and the like.

Preferred anti-obesity agents for use in the combination aspects of the present invention include gut-selective MTP inhibitors CCKa agonists, 5HT2c agonists, MCR4 agonist, lipase inhibitor, opioid antagonists, oleoyl-estrone, obinepitide, pramlintide (Symlin®), tesofensine (NS2330), leptin, liraglutide, bromocriptine, orlistat, exenatide (Byetta®), AOD-9604 (CAS No. 221231-10-3) and sibutramine.

Suitable anti-diabetic agents include a sodium-glucose co-transporter (SGLT) inhibitor, a phosphodiesterase (PDE) 10 inhibitor, a diacylglycerol acyltransferase (DGAT) 1 or 2 inhibitor, a sulfonylurea (e.g., acetohexamide, chiorpropamide, diabinese, glibenclamide, glipizide, glyburide, glimepiride, gliclazide, glipentide, gliquidone, glisolamide, tolazamide, and tolbutamide), a meglitinide, an alpha-amylase inhibitor (e.g., tendamistat, trestatin and AL-3688), an alpha-glucoside hydrolase inhibitor (e.g., acarbose), an alpha-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR alpha/gamma agonist (e.g., CLX-0940, GW-1536, GW-20 1929, GW-2433, KRP-297, L-796449, LR-90, MK-0767 and SB-219994), a biguanide (e.g., metformin), a GLP-1 derivative, a glucagon-like peptide 1 (GLP-1) agonist (e.g., Byetta™, exendin-3 and exendin-4), a protein tyrosine phosphatase-1 B (PTP-1 B) inhibitor (e.g., trodusquemine, hyrtiosal extract), SIRT-1 inhibitor (e.g. resveratrol), a dipeptidyl peptidease IV (DPP-IV) inhibitor (e.g., sitagliptin, vildagliptin, alogliptin, linagliptin and saxagliptin), an insulin secreatagogue, a fatty acid oxidation inhibitor, an A2 antagonist, a c-jun amino-terminal kinase (JNK)

inhibitor, an insulin, an insulin derivative, fast acting insulins, inhalable insulins, oral insulins, an insulin mimetic, a glycogen phosphorylase inhibitor, a VPAC2 receptor agonist and a glucokinase activator. Preferred anti-diabetic agents are metformin, a glucagon-like peptide 1 (GLP-1) agonist (e.g., Byetta™) and DPP-IV inhibitors (e.g. sitagliptin, vildagliptin, alogliptin, linagliptin and saxagliptin).

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of acetyl-CoA carboxylase(s), in particular ACC2, in particular diseases or conditions as described hereinbefore and hereinafter.

In yet another aspect the present invention relates a method for treating, including preventing a disease or condition mediated by the inhibition of acetyl-CoA carboxylase(s) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Further aspects of the invention include the use of a compound according to the invention or a salt thereof as a crop protection agent to combat and/or prevent fungal infestations, or to control other pests such as weeds, insects, or acarids that are harmful to crops. Another aspect of the invention relates to the use of a compound according to the invention or a salt thereof for controlling and/or preventing plant pathogenic microorganisms, for example plant pathogenic fungi. Therefore one aspect of the invention is a compound according to the formula (I) or a salt thereof for use as a fungicide, insecticide, acaricide and/or herbicide. Another aspect of the invention relates to an agricultural composition comprising a compound of the present invention together with one or more suitable carriers. Another aspect of the invention relates to an agricultural composition comprising a compound of the present invention in combination with at least one additional fungicide and/or systemically acquired resistance inducer together with one or more suitable carriers.

EXAMPLES

The Examples that follow are intended to illustrate the present invention without restricting it. The terms "ambient temperature" and "room temperature" are used interchangeably and designate a temperature of about 20° C.

Preliminary Remarks:

As a rule, 1H-NMR and/or mass spectra have been obtained for the compounds prepared. The $R_f$ values are determined using Merck silica gel 60 $F_{254}$ plates and UV light at 254 nm.

| | Abreviations: |
|---|---|
| ACN | acetonitrile |
| AcOH | acetic acid |
| aq. | aqueous |
| BOC | tert-butoxy-carbonyl- |
| CDI | N,N-carbonyldiimidazole |
| CDT | N,N-carbonylditriazole |
| CyH | cyclohexane |
| DBAD | di-tert-butyl azodicarboxylate |
| DCM | dichloromethane |
| DIAD | diisopropyl azodicarboxylate |
| DIBAlH | diisobutyl aluminium hydride |
| DIPE | diisopropyl ether |
| DIPEA | N,N-diisopropylethylamine |
| DMAP | 4-dimethylaminopyridine |
| DMF | N,N-dimethylformamide |
| DMSO | dimethyl sulfoxide |
| EI-MS | electron induced mass spectrometry |
| ESI-MS | electrospray ionisation mass spectrometry |
| EtOAc | ethyl acetate |
| EtOH | ethanol |
| Ex | example |
| FA | formic acid |
| GC | gas chromatography |
| HATU | 2-(1H-7-azabenzotriazol-1-yl)-1,1,3,3-tetramethyluronium hexafluorophosphate |
| HOBt | N-hydroxybenzotriazole |
| HPLC | high performance liquid chromatography |
| LAH | lithium aluminium hydride |
| MeOH | methanol |
| m.p. | melting point |
| MS | mass spectrum |
| MsCl | methanesulfonyl chloride |
| n.d. | not determined |
| NMP | N-methyl-2-pyrrolidone |
| Pd/C | palladium on activated carbon |
| PE | petroleum ether |
| PG | protecting group |
| $R_f$ | retention factor |
| r.t. | room temperature (about 20° C.) |
| $R_t$ | retention time |
| sat. | saturated |
| TBME | tert-butyl methyl ether |
| TEA | triethylamine |
| TF/TFA | trifluoroacetic acid |
| THF | tetrahydrofuran |
| TBAF | tetrabutylammonium fluoride |
| TBTU | 2-(1H-benzotriazol-1-yl)-1,1,3,3-tetramethyluronium tetrafluoroborat |
| TLC | thin layer chromatography |
| TMS | trimethylsilyl |
| Ts | 4-toluenesulfonyl |
| X-Phos | 2-dicyclohexylphosphino-2',4',6'-triisopropylbiphenyl |

Preparation of Starting Compounds

Example I 1-(4-Hydroxyphenyl)propane-2-amine

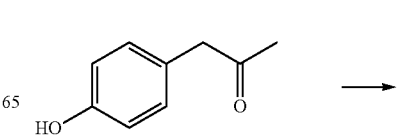

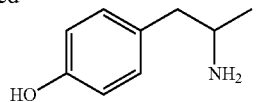

A mixture of 7.00 g (46.6 mmol) 4-hydroxyphenylacetone and 200 mL 7N ammonia in MeOH is charged with 0.70 g Raney nickel. The mixture is stirred in an hydrogen atmosphere (50 psi) at r.t. over night. After complete reaction, the mixture is filtrated, the solvent is removed in vacuo and the crude product is purified by HPLC (MeOH/H$_2$O/NH$_3$).

C$_9$H$_{13}$NO (M=151.2 g/mol)
ESI-MS: 152 [M+H]$^+$
R$_t$ (HPLC): 0.95 min (method A)

Example II (S)-4-(1-Amino-ethyl)-phenol hydrobromid

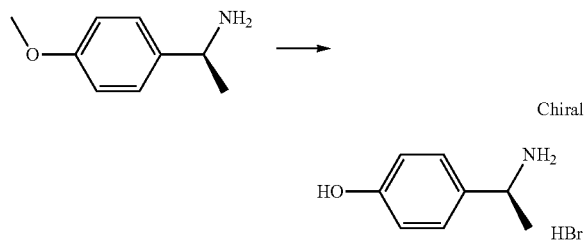

To 11.0 g (72.7 mmol) (S)-1-(4-methoxy-phenyl)-ethylamine is added carefully 30 mL HBr (30% in HOAc). The mixture is stirred at 100° C. for 4 h. After cooling down to r.t., the solvent is removed in vacuo and the residue is dried in vacuo. The resulting product is used without further purification.

C$_6$H$_{11}$NO*HBr (M=218.1 g/mol)
ESI-MS: 121 [M+H—NH$_3$]+
R$_t$ (HPLC): 0.50 min (method A)

Example III

Example III.1 (General Route)

(S)—N-(1-(4-Bromophenyl)ethyl)acetamide

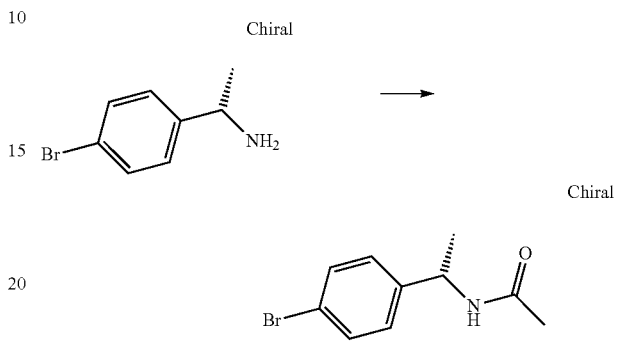

To 200 g (1.00 mol) (S)-1-(4-bromophenyl)ethylamine in 800 mL DCM are slowly added 94.5 mL (1.00 mol) acetic anhydride while cooling the mixture to 20-30° C. Then the cooling is removed and the reaction mixture is stirred at r.t. over night. Afterwards the mixture is consecutively washed with water, sat. aq. NaHCO$_3$ solution, water, diluted aq. citric acid solution and again water. The org. layer is dried with MgSO$_4$ and the solvent is removed in vacuo. The crude product is used without further purification.

C$_{10}$H$_{12}$BrNO (M=242.1 g/mol)
ESI-MS: 242/244 [m+H]$^+$
R$_t$ (HPLC): 1.67 min (method A)

The following compounds are prepared analogously to example III.1. For the examples III.2-3 acetic acid is used as solvent and after complete reaction the solvent is removed in vacuo and the residue is partioned between EtOAc and water.

| Ex. | Starting material | Product structure | Mass spec result | HPLC retention time (method) |
|---|---|---|---|---|
| III.1 | -NH2 Chiral) | -NHAc Chiral) | 242/244 [M + H]$^+$ | 1.67 (A) |
| III.2 | -NH2) | -NHAc) | 242 [M + H]$^+$ | 2.47 (B) |
| III.3 | -NH2) | -NHAc) | 194 [M + H]$^+$ | 1.80 (B) |

Example IV

N-(1-(4-iodophenyl)ethyl)acetamide

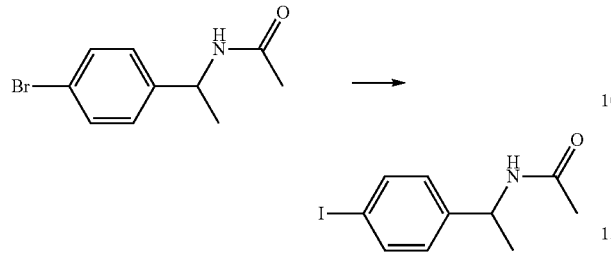

To 8.70 g (35.9 mmol) N-(1-(4-bromophenyl)ethyl)acetamide (III.2) in 100 mL 1,4-dioxane are added 0.69 g (3.62 mmol) CuI, 0.97 mL (9.11 mmol) N,N"-dimethyl-ethylendiamine and 10.8 g (71.9 mmol) NaI. The reaction mixture is stirred at 120° C. for 3 d. The mixture is allowed to cool to r.t. and half of the solvent is removed in vacuo. EtOAc and diluted aq. ammonia solution are added and the layers are separated. The aq. layer is once more extracted with EtOAc. The organic layers are combined, dried with $Na_2SO_4$ and the solvent is removed in vacuo. The crude product is triturated with diethylether and dried in vacuo.

$C_{10}H_{12}INO$ (M=289.1 g/mol)
ESI-MS: 290 [M+H]$^+$
$R_t$ (HPLC): 2.95 min (method B)

Example V (S)—N-(1-(4-Hydroxyphenyl)ethyl)acetamide

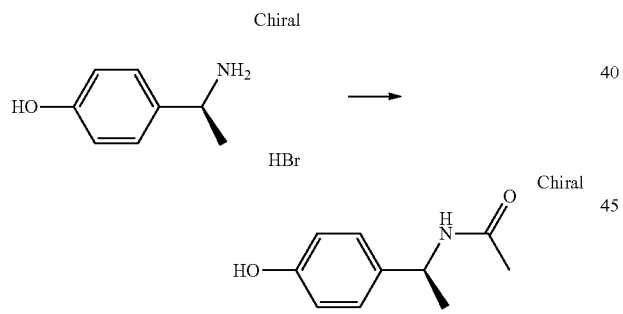

19.5 g (71.5 mmol) of example II are added to 50 mL THF and charged with 40 mL (287 mmol) TEA. 5.59 mL (78.7 mmol) acetyl chloride are added carefully and the mixture is stirred at r.t. for 2 h. 100 ml water are added and the reaction mixture is slightly acidified with citric acid. The aqueous phase is extracted four times with EtOAc. The org. phases are combined, dried with $MgSO_4$ and the solvent is removed in vacuo. The crude product is dissolved in 40 mL MeOH and charged with 30 mL aq. 4N NaOH-solution and stirred at r.t for 1.5 h. Then 34 mL aq. 4 N HCl solution are added and the aqueous phase is extracted three times with ethyl acetate. The org. phases are combined, dried with $MgSO_4$ and the solvent is removed in vacuo. The crude product is purified by HPLC ($MeOH/H_2O/NH_3$).

$C_{10}H_{13}NO_2$ (M=179.2 g/mol)
ESI-MS: 180 [M+H]$^+$
$R_t$ (HPLC): 0.52 min (method A)

Example VI

N-(1-(4-Hydroxyphenyl)ethyl)acetamide

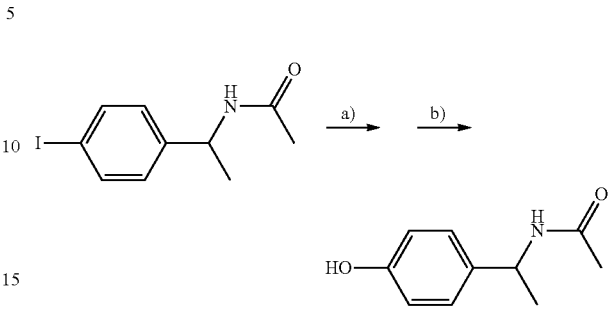

a) 1.00 g (3.46 mmol) of example IV.3 and 1.02 g (10.4 mmol) KOAc are added to 10 mL DMSO. After degassing the mixture 1.32 g (5.19 mmol) bis(pinakolato)diboron and 141 mg (0.17 mmol) $PdCl_2(dppf)*CH_2Cl_2$ are added and the mixture is stirred at 80° C. for 1.5 h. 80 mL EtOAc are added and the resulting mixture is washed with water (3×). The org. phase is dried with $MgSO_4$ and the solvent is removed in vacuo. The crude product is purified by column chromatography (silica gel, DCM/MeOH 9/1).

$C_{16}H_{24}BNO_3$ (M=289.2 g/mol)
ESI-MS: 290 [m+H]$^+$
$R_t$ (HPLC): 1.81 min (method A)

b) 0.90 g (3.11 mmol) of the above mentioned product is added to 20 mL THF and cooled down to 0° C. 0.78 mL (3.11 mmol) 4N aq. NaOH solution and 0.41 mL (4.67 mmol) $H_2O_2$ (35% in water) are added and the resulting mixture is stirred for 3 h at constant temperature. The mixture is separated between water and EtOAc and the aq. phase is extracted with EtOAc (3×). The org. phases are combined and the solvent is removed in vacuo. The crude product is purified by HPLC ($MeOH/H_2O/NH_3$). The resulting product is triturated with diethylether.

$C_{10}H_{13}NO_2$ (M=179.2 g/mol)
ESI-MS: 180 [M+H]$^+$
$R_t$ (HPLC): 1.16 min (method E)

Example VII (S)-3-(1-(4-hydroxyphenyl)ethyl)-1,1-dimethylurea

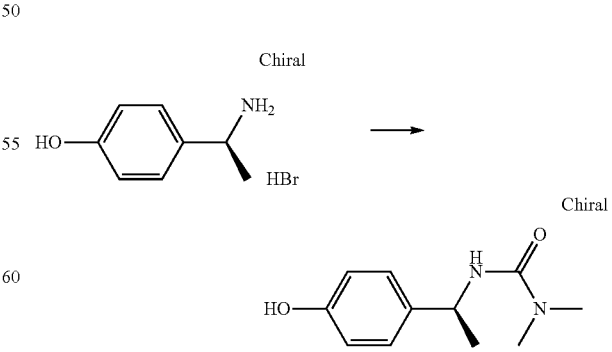

7.20 g (33.0 mmol) of example II are added to 80 mL DCM and charged with 18.5 mL (132 mmol) TEA. After cooling down to 0° C. 5.88 g (36.3 mmol) CDI are added, the cooling is removed and stirring is continued for 20 min. 4.46 g (99.0 mmol) dimethylamine are added an the mixture is stirred at r.t. over night. 1 N aq. citic acid is added, the phases are separated and the aq. phase is extracted one more time with DCM. The org. phases are combined, dried with MgSO$_4$ and the solvent is removed in vacuo. The crude product is purified by column chromatography (silica gel, DCM/MeOH 95/5→90/10).

$C_{11}H_{16}N_2O_2$ (M=208.3 g/mol)
ESI-MS: 209 [M+H]$^+$
R$_t$ (HPLC): 0.94 min (method A)

Example VIII (S)—N-(1-(4-hydroxyphenyl)ethyl)cyclopropanecarboxamide

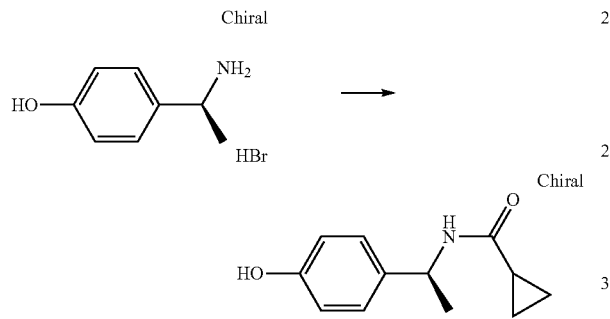

7.20 g (33.0 mmol) of example II are added to 80 mL DCM and charged with 18.5 mL (132 mmol) TEA. After cooling down to 0° C. 3.59 mL (39.6 mmol) cyclopropanecarbonyl chloride are carefully added. Afterwards the cooling is removed and the reaction mixture is stirred at r.t. over night. The reaction mixture is further diluted with DCM and washed with aq. citric acid. The aq. phase is extracted one more time with DCM. The org. phases are combined, dried with MgSO$_4$ and the solvent is removed in vacuo. The crude product is purified by column chromatography (silica gel, DCM/MeOH 95/5→90/10).

$C_{12}H_{15}NO_2$ (M=205.3 g/mol)
ESI-MS: 206 [M+H]$^+$
R$_t$ (HPLC): 0.81 min (method A)

Example IX (S)-tert-Butyl 1-(4-hydroxyphenyl)ethylcarbamate

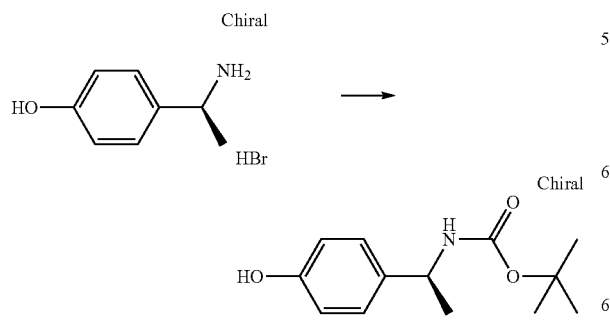

5.00 g (22.9 mmol) of example II are added to 80 mL DCM and charged with 34.4 mL (68.8 mmol) of a 2N aq. Na$_2$CO$_3$ solution. 5.25 g (24.1 mmol) Boc$_2$O in 20 mL DCM are added and the mixture is stirred at r.t. for 2 h. 100 mL water are added and the resulting mixture is extracted three times with DCM. The org. phases are combined, washed with water, dried with MgSO$_4$ and the solvent is removed in vacuo. The crude product is purified by column chromatography (silica gel, DCM/MeOH 95/5→80/20).

$C_{13}H_{19}NO_3$ (M=237.3 g/mol)
ESI-MS: 238 [M+H]$^+$
R$_t$ (HPLC): 1.58 min (method A)

Example X (S)-Benzyl 1-(4-hydroxyphenyl)ethylcarbamate

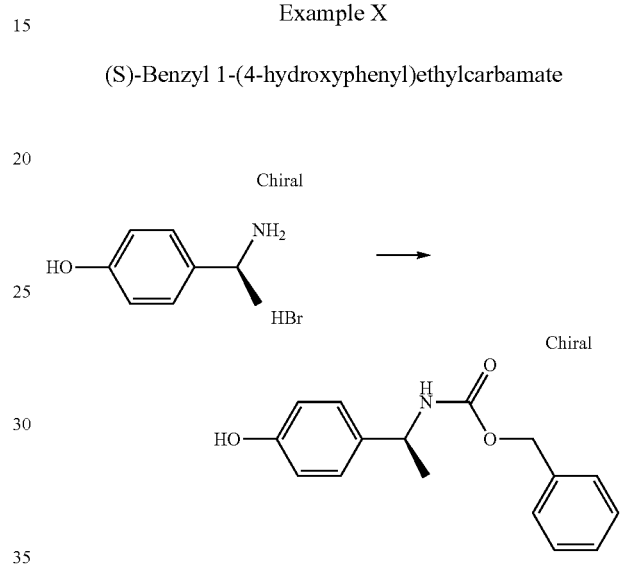

7.20 g (33.0 mmol) of example II are added to a mixture of 10 mL THF and 10 mL water. 19.4 g (231 mmol) NaHCO$_3$ are slowly added so that the pH>7. 5.18 mL (36.3 mmol) benzyl chloroformate is added slowly and the resulting mixture is stirred at r.t. for 3 h. 100 mL water are added and the mixture is slightly acidified with 10% aq. citric acid. The resulting mixture is extracted two times with EtOAc. The org. phases are combined, dried with MgSO$_4$ and the solvent is removed in vacuo. The crude product is purified by column chromatography (silica gel, DCM/MeOH 95/5→80/20).

$C_{13}H_{19}NO_3$ (M=271.3 g/mol)
ESI-MS: 272 [M+H]$^+$
R$_t$ (HPLC): 1.69 min (method A)

Example XI

Example XI.1 (General Route)

(S)-tert-Butyl 3-(4-(1-acetamidoethyl)phenoxy)azetidine-1-carboxylate

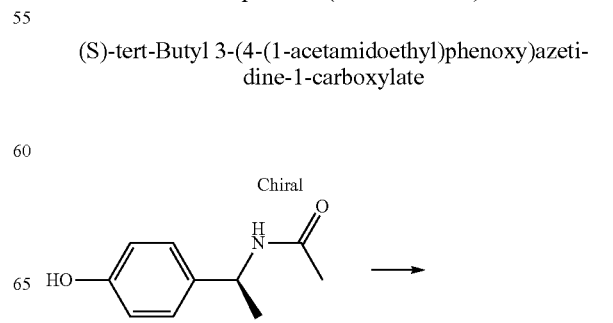

-continued

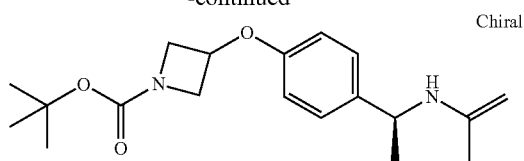

6.00 g (33.5 mmol) of exampleV are added to 120 mL DMF and charged with 8.41 g (33.5 mmol) 1-Boc-3-methanesulfonyloxyazetidine and 21.8 g (67.0 mmol) $Cs_2CO_3$. The reaction mixture is stirred at 80° C. over night. The reaction is quenched by the addition of water. The resulting mixture is extracted two times with EtOAc. The org. phases are combined, washed with diluted aq. $NaHCO_3$ solution (3×), dried with $MgSO_4$ and the solvent is removed in vacuo. The crude product is purified by HPLC ($MeOH/H_2O/NH_3$).

$C_{18}H_{26}N_2O_4$ (M=334.4 g/mol)
ESI-MS: 335 $[M+H]^+$
$R_f$ (HPLC): 1.88 min (method A)

The following compounds are prepared analogously to example XI.1.

For the example XI.6 1-Boc-3-iodoazetidine is used.

| Ex. | Starting material | Product structure | Mass spec result | HPLC retention time (method) |
|---|---|---|---|---|
| XI.1 | V | | 335 $[M + H]^+$ | 1.88 (A) |
| XI.2 | VI | | 335 $[M + H]^+$ | 1.87 (A) |
| XI.3 | III.4 | | 349 $[M + H]^+$ | 1.93 (A) |
| XI.4 | VIII | | 361 $[M + H]^+$ | 2.19 (A) |
| XI.5 | VII | | 364 $[M + H]^+$ | 2.12 (A) |
| XI.6 | X | | 444 $[M + NH_4]^+$ | 2.25 (A) |

Example XII (S)-tert-Butyl 1-(4-(1-benzhydrylazetidin-3-yloxy)phenyl)ethylcarbamate

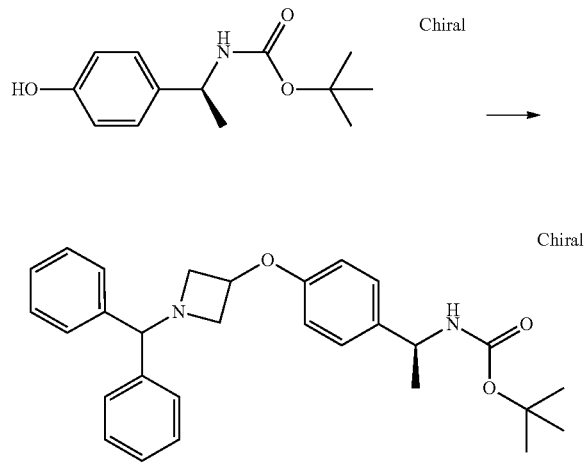 [SMILES: C[C@H](NC(=O)OC(C)(C)C)c1ccc(O)cc1 ; C[C@H](NC(=O)OC(C)(C)C)c1ccc(OC2CN(C(c3ccccc3)c3ccccc3)C2)cc1]

7.48 g (31.5 mmol) of example IX are added to 150 mL DMF and charged with 10.0 g (33.5 mmol) 1-diphenylmethyl-3-methanesulfonyloxyazetidine and 20.5 g (63.0 mmol) $Cs_2CO_3$. The reaction mixture is stirred at 80° C. for 3 h, filtered and the solvent is removed in vacuo. The crude product is purified by column chromatography (PE/EtOAc 80/20→50/50).

$C_{29}H_{34}N_2O_3$ (M=458.6 g/mol)
ESI-MS: 459 [M+H]$^+$
$R_t$ (HPLC): 2.32 min (method A)

Example XIII

Example XIII.1 (General Route)

(S)—N-(1-(4-(Azetidin-3-yloxy)phenyl)ethyl)acetamide

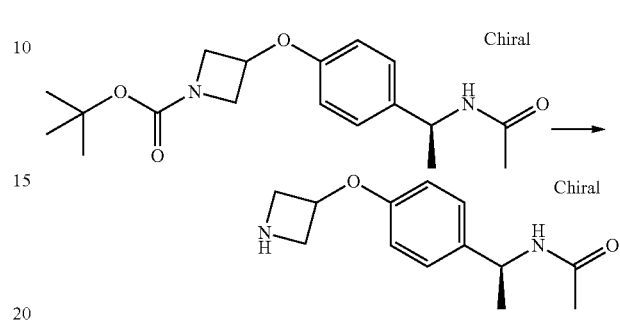

To 1.20 g (3.59 mmol) of example XI.1 in 10 mL MeOH are added 8.61 mL (10.8 mmol) HCl (c=1.3 mol/l in MeOH). The reaction mixture is stirred at r.t. over night. The solvent is removed in vacuo and the residue is purified by HPLC (MeOH/H$_2$O/NH$_3$).

$C_{13}H_{18}N_2O_2$ (M=234.3 g/mol)
ESI-MS: 235 [M+H]$^+$
$R_t$ (HPLC): 1.06 min (method A)

The following compounds are prepared analogously to example XIII.1.

For the examples XIII.3 and XIV.4a gentle warming (~35-40° C.) is applied.

For the example XIII.5 aq. NaOH (1N) is added to the residue and the resulting precipitate is filtered, washed and dried.

For the example XIII.6 the residue is not purified by HPLC.

| Ex. | Starting material | Product structure | Mass spec result | HPLC retention time (method) |
|---|---|---|---|---|
| XIII.1 | XI.1 | | 235 [M + H]$^+$ | 1.06 (A) |
| XIII.2 | XI.2 | | 235 [M + H]$^+$ | 1.06 (A) |
| XIII.3 | XI.4 | | 261 [M + H]$^+$ | 1.23 (A) |

-continued

| Ex. | Starting material | Product structure | Mass spec result | HPLC retention time (method) |
|---|---|---|---|---|
| XIII.4 | XI.5 | Chiral structure | 264 [M + H]+ | 1.17 (A) |
| XIII.5 | XI.6 | Chiral structure | 327 [M + H]+ | 1.72 (A) |
| XIII.6 | XI.1 | Chiral structure | 235 [M + H]+ | 1.06 (A) |

Example XIV

N-(1-(4-(Azetidin-3-yloxy)phenyl)propan-2-yl)acetamide

To 0.90 g (2.58 mmol) of example XI.3 in 15 mL DCM is added 1 mL TFA. The reaction mixture is stirred at r.t. for 3 h and afterwards neutralised with sat. aq. NaHCO₃ solution. The aq. Phase is saturated with K₂CO₃ and extracted with EtOAc and MeOH (3×). The org. phases are combined, dried with MgSO₄ and the solvent is removed in vacuo.

$C_{14}H_{20}N_2O_2$ (M=248.3 g/mol)
ESI-MS: 249 [M+H]+
$R_t$ (HPLC): 1.23 min (method A)

Example XV (S)-tert-Butyl 1-(4-(azetidin-3-yloxy)phenyl) ethylcarbamate

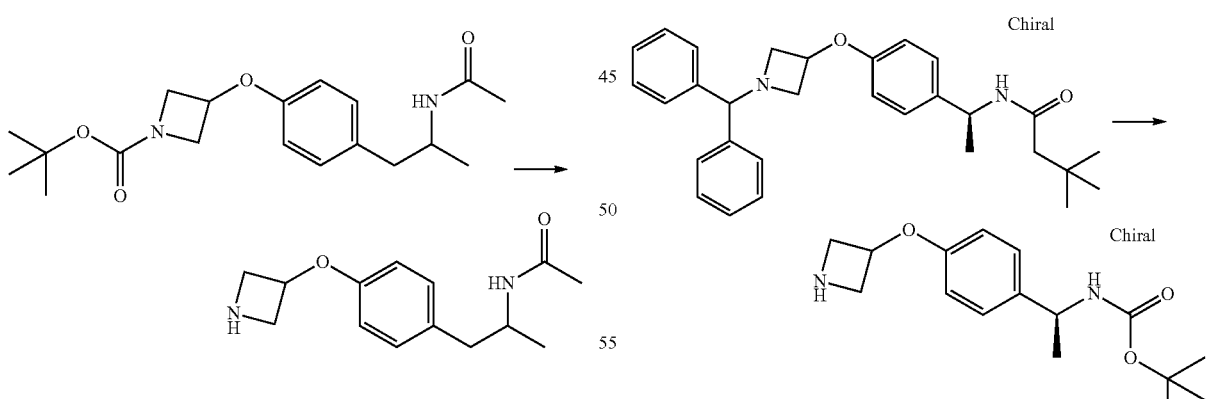

7.20 g (15.7 mmol) of example XII are added to 50 mL EtOH and charged with 1.00 g Pd/C (10%). The reaction mixture is hydrogenated at r.t. for 24 h at a hydrogen pressure of 3 bar. The reaction mixture is filtered and the solvent is removed in vacuo. The crude product is triturated with TBME.

$C_{16}H_{24}N_2O_3$ (M=292.4 g/mol)
ESI-MS: 293 [M+H]+
$R_t$ (HPLC): 1.72 min (method A)

Example XVI

Example XVI.1 (General Route)

1-Bromo-4-cyclopropylmethoxybenzene

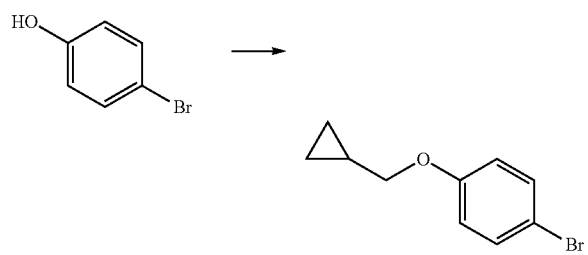

5.0 g (28.9 mmol) 4-bromophenol, 3.93 g (43.4 mmol) (chloromethyl)cyclopropane and 7.99 g (57.8 mmol) $K_2CO_3$ are added to 10 mL DMF and stirred at 80° C. over night. Afterwards the reaction mixture is diluted with water and extracted with DCM. The organic layer is dried with $MgSO_4$ and the solvent is removed in vacuo.

$C_{10}H_{11}BrO$ (M=227.1 g/mol)
EI-MS: 226/228 $[M]^+$
$R_t$ (HPLC): 8.16 min (method J)

The following compounds are prepared analogously to example XVI.1

For example XVI.2 the reaction temperature is 120° C.

For example XVI.17 the reaction temperature is 140° C. and the product is purified by column chromatography (silica gel, PE/EtOAc 8/2).

For example XVI.19 KOtBu is used as base and the reaction mixture is stirred at 100° C. for 6 h.

| Ex. | Starting material | Starting material | Product structure | Mass spec result | HPLC retention time (method) |
|---|---|---|---|---|---|
| XVI.1 | HO-C6H4-Br | cyclopropyl-CH2-Cl | cyclopropyl-CH2-O-C6H4-Br | 226/228 $[M]^+$ | 8.16 (J) |
| XVI.2 | HO-C6H4-Br | cyclobutyl-Br | cyclobutyl-O-C6H4-Br | 226/228 $[M]^+$ | 4.90 (Q) |
| XVI.3 | HO-C6H4-Br | cyclopentyl-CH3 | cyclopentyl-O-C6H4-Br | n.d. | 9.01 (J) |
| XVI.4 | Br-C6H4-OH (meta) | propyl-Br | propyl-O-C6H4-Br (meta) | n.d. | 8.53 (J) |
| XVI.5 | Br-C6H4-OH (meta) | isobutyl-Br | isobutyl-O-C6H4-Br (meta) | n.d. | 4.81 (R) |
| XVI.6 | HO-C6H3(F)-Br | cyclopropyl-CH2-Cl | cyclopropyl-CH2-O-C6H3(F)-Br | 244/246 $[M]^+$ | 2.08 (A) |
| XVI.7 | HO-C6H3(F)-Br | ethyl-Br | ethyl-O-C6H3(F)-Br | 219 $[M - C_4H_7]^-$ | 2.17 (A) |

-continued

| Ex. | Starting material | Starting material | Product structure | Mass spec result | HPLC retention time (method) |
|---|---|---|---|---|---|
| XVI.8 | HO-C6H3(OMe)-Br | Et-Br | EtO-C6H3(OMe)-Br | 231/233 [M + H]+ | 2.00 (A) |
| XVI.9 | HO-C6H3(OMe)-Br | cyclobutyl-Br | cyclobutyl-O-C6H3(OMe)-Br | 257/259 [M + H]+ | 2.18 (A) |
| XVI.10 | HO-C6H3(OMe)-Br | sec-butyl-Br | sec-BuO-C6H3(OMe)-Br | 259/261 [M + H]+ | 2.21 (A) |
| XVI.11 | HO-C6H3(OMe)-Br | cyclopropyl-CH2-Cl | cyclopropylmethyl-O-C6H3(OMe)-Br | 257/259 [M + H]+ | 2.11 (A) |
| XVI.12 | HO-C6H3(OMe)-Br | n-Pr-Br | n-PrO-C6H3(OMe)-Br | 244/246 [M]+ | 2.12 (A) |
| XVI.13 | HO-C6H3(OMe)-Br | i-Pr-Br | i-PrO-C6H3(OMe)-Br | 245/247 [M + H]+ | 1.30 (N) |
| XVI.14 | HO-C6H3(CN)-Br | n-Pr-Br | n-PrO-C6H3(CN)-Br | 257/259 [M + NH4]+ | 2.27 (A) |
| XVI.15 | HO-C6H3(CN)-Br | cyclopropyl-CH2-Cl | cyclopropylmethyl-O-C6H3(CN)-Br | 252/254 [M + H]+ | 2.00 (A) |
| XVI.16 | HO-C6H3(CN)-Br | cyclobutyl-Br | cyclobutyl-O-C6H3(CN)-Br | 251/253 [M]+ | 2.07 (A) |
| XVI.17 | HO-C6H3(OH)-Br | Et-Br | EtO-C6H3(OEt)-Br | n.d. | 2.06 (A) |
| XVI.18 | HO-C6H3(OH)-Br | TsOCH2-C(Me)2-CH2OTs | 3,3-dimethyl-benzo-dioxepine-Br | n.d. | TLC: Rf = 0.9 PE/EtOAc 8/2 |

| Ex. | Starting material | Starting material | Product structure | Mass spec result | HPLC retention time (method) |
|---|---|---|---|---|---|
| XVI.19 | 3-bromophenol | ethyl 4-bromobutanoate | ethyl 4-(3-bromophenoxy)butanoate | 287/289 [M + H]⁺ | 1.57 (P) |
| XVI.20 | 4-bromo-2-fluorophenol | (1-fluoro-2-(bromomethyl))-2-fluorocyclopropane | aryl ether product | n.d. | 1.31 (N) |
| XVI.21 | 4-bromo-3-methoxyphenol | (1-fluoro-2-(bromomethyl))-2-fluorocyclopropane | aryl ether product | n.d. | 1.27 (N) |

Example XVII

Example XVII.1 (General Route)

1-Bromo-4-(2-bromoethoxy)benzene

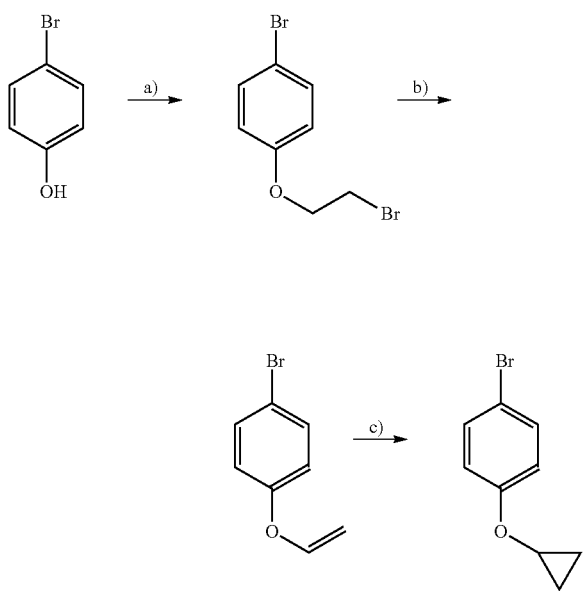

a) 55.0 g (318 mmol) 4-bromophenol and 14.1 g (352 mmol) NaOH are added to 110 mL water. 41.1 mL (477 mmol) dibromoethane are added slowly and the reaction mixture is stirred for 16 h under reflux. Afterwards the reaction mixture is extracted with DCM and the solvent is removed in vacuo. The crude product is purified by column chromatography (silica gel, CyH/EtOAc 4/1).

b) 52.0 g (186 mmol) of 1-bromo-4-(2-bromoethoxy)benzene is added to 300 mL THF and cooled down to 0° C. Within 30 min 25.0 g (223 mmol) KOtBu are added to this mixture in several portions. Cooling is removed and the reaction mixture is stirred at r.t. over night. The reaction is queched by the addition of water. The resulting mixture is extracted with EtOAc (2×). The org. phases are combined, washed with sat. aq. NaCl solution, dried with MgSO₄ and the solvent is removed in vacuo. The resulting product is used without further purification.

c) 39.0 g (176 mmol) of 1-bromo-4-vinyloxybenzene and 32.4 mL (441 mmol) chloroiodomethane are added to 500 mL dichloroethane and cooled down to 0° C. During 1 h 200 mL (200 mmol) diethylzinc solution (c=μmol/lin hexane) are added and stirring is continued for 2 h at 0° C. The reaction is quenched by the addition of 200 mL of a sat. aq. NH₄Cl solution and extracted with TBME (2×). The org. phases are combined, washed with sat. aq. NaCl solution, dried with MgSO₄ and the solvent is removed in vacuo. The crude product is purified by column chromatography (silica gel, PE).

$C_9H_9BrO$ (M=213.1 g/mol)
EI-MS: 212/214 [M]⁺
$R_f$(TLC): 0.4 (silica gel, PE)

The following compounds are prepared analogously to example XVII.1 For the examples XVII.2-XVII.4 the phenolate in step a) is preformed by reacting the appropriate phenol with NaOH in a MeOH/water (1/1) mixture at r.t. for 1 h. Then the solvent is removed in vacuo and the resulting sodium salt is reacted with dibromoethane (5 eq.) at 100° C. for 24 h. The reaction mixture is quenched by the addition of water and extracted with DCM.

For example XVII.5 step a: To the diphenol and dibromoethane (8 eq.) in acetone is added $Cs_2CO_3$ (5 eq.) and the reaction mixture is stirred at 90° C. for 45 h. The reaction mixture is quenched by the addition of water and extracted with EtOAc.

For example XVII.6 the phenol is added to THF, deprotonated with NaH at 0° C. and after the addition of dibromoethane the reaction mixture is refluxed for 16 h followed by an aq. work up.

| Ex. | Starting material | Product structure | Mass spec result | HPLC retention time (method) |
|---|---|---|---|---|
| XVII.1 | HO—⌬—Br | ▽—O—⌬—Br | 212/214 [M]+ | TLC: $R_f = 0.4$ (silica gel, PE) |
| XVII.2 | HO—⌬(Me)—Br | ▽—O—⌬(Me)—Br | n.d. | 5.89 (H) |
| XVII.3 | HO—⌬(OMe)—Br | ▽—O—⌬(OMe)—Br | n.d. | 5.30 (I) |
| XVII.4 | HO—⌬(F,F)—Br | ▽—O—⌬(F,F)—Br | n.d. | 7.34 (I) |
| XVII.5 | HO—⌬(OH)—Br | ▽—O—⌬(O—▽)—Br | n.d. | 8.50 (J) |
| XVII.6 | HO—⌬(F)—Br | ▽—O—⌬(F)—Br | 230/232 [M]+ | TLC: $R_f = 0.54$ (silica gel, hexane/ EtOAc 9/1) |

Example XVIII

5-Bromo-2-cyclobutoxy-pyrimidine

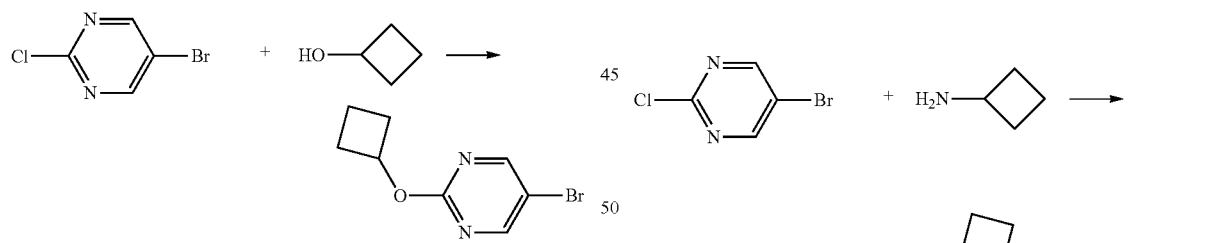

2.42 mL (31.0 mmol) cyclobutanol and 3.00 g (15.5 mmol) 5-bromo-2-chloropyrimidine are added to 40 mL 1,4-dioxane and cooled down to 0° C. Then the reaction mixture is charged with 1.86 g (46.5 mmol) NaH. After removing of the cooling bath the reaction mixture is stirred at r.t. for 1 h. The reaction is quenched by the addition of water and sat. aq. NaHCO$_3$ solution. The 1,4-dioxane is removed in vacuo and the aq. residue is extracted with DCM. The org. phases are combined, washed with water and dried with MgSO$_4$. The solvent is removed under reduced pressure. The crude product is used without further purification.

$C_9H_{11}BrN_2O$ (M=229.1 g/mol)
ESI-MS: 229/231 [m+H]+
$R_t$ (HPLC): 1.93 (method A)

Example XIX

5-Bromo-N-cyclobutylpyrimidin-2-amine

In a sealed tube 2.00 g (10.3 mmol) 5-bromo-2-chloropyrimidine, 1.15 mL (13.4 mmol) cyclobutylamin and 2.70 mL (15.5 mmol) DIPEA are added to 12 mL ACN. The reaction mixture is stirred at 50° C. over night, then diluted with EtOAc and washed with water (2×). The org. phase is dried with MgSO$_4$ and the solvent is removed in vacuo.

$C_8H_{10}BrN_3$ (M=228.1 g/mol)
ESI-MS: 228/230 [m+H]+
$R_t$ (HPLC): 1.87 (method A)

Example XX

5-Bromo-N-sec-butylpyrimidin-2-amine

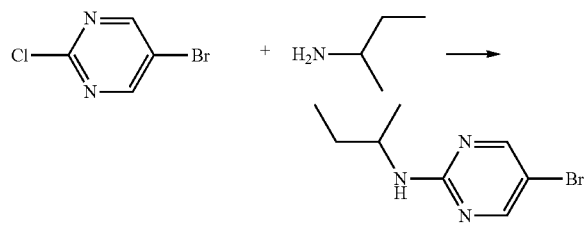

In a sealed tube 2.00 g (10.3 mmol) 5-bromo-2-chloropyrimidine and 3.13 mL (31.0 mmol) sec-butylamin are added to 12 mL ACN. The reaction mixture is stirred at 120° C. for 2 h, then diluted with EtOAc and washed with water (2×). The org. phase is dried with MgSO$_4$ and the solvent is removed in vacuo. $C_8H_{12}BrN_3$ (M=230.1 g/mol)

ESI-MS: 230/232 [m+H]$^+$
R$_t$ (HPLC): 1.93 (method A)

Example XXI

Example XXI.1 (General Route)

2-Chloro-5-cyclopropylpyrimidine

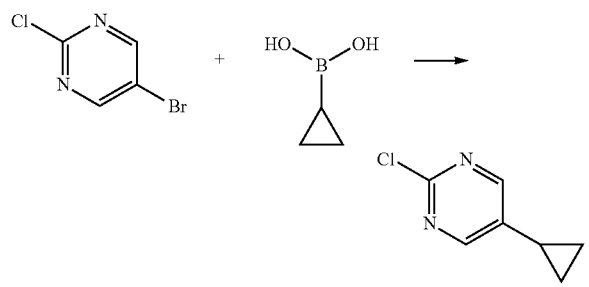

3.60 g (18.6 mmol) 5-bromo-2-chloropyrimidine, 4.80 g (55.8 mmol) cyclopropyl boronic acid, 13.8 g (65.1 mmol) K$_3$PO$_4$, 568 mg (2.03 mmol) tricyclohexylphosphine and 4 mL water are added to 80 mL toluene. The mixture is degassed thoroughly and charged with 627 mg (2.79 mmol) Pd(OAc)$_2$. After degassing again the mixture is stirred at 100° C. over night, filtered and the solvent is removed in vacuo. The crude product is purified by column chromatography (silica gel, PE/EtOAc 90/10→70/30).

$C_7H_7ClN_2$ (M=154.6 g/mol)
EI-MS: 155 [M+H]$^+$
R$_t$ (HPLC): 1.34 (method A)

Example XXII

Example XXII.1 (General Route)

5-Chloro-2-phenyloxazolo[5,4-d]pyrimidine

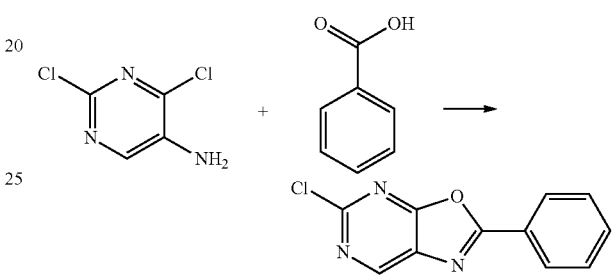

7.82 g (64.0 mmol) benzoic acid and 20 mL POCl$_3$ are stirred together at 100° C. for 30 min. Within 45 min 7.00 g (42.7 mmol) 2,6-dichloro-5-aminopyrimidine are added by several portions. The reaction mixture is stirred for additional 2 h at the same temperatur. After that the mixture is carefully added to an ice cold aq. NaOH solution. The resulting precipitate is filtered, washed with water and dried.

$C_{11}H_6ClN_3O$ (M=231.6 g/mol)
EI-MS: 232 [M+H]$^+$
R$_t$ (HPLC): 2.22 (method S)

The following compounds are prepared analogously to example XXII.1.

For the example XXII.2 the solvent of reaction mixture is removed in vacuo and the residue is triturated first with diethylether, then dissolved in DCM, filtered and the solvent is removed in vacuo again. The residue is one more time triturated with diethylether.

| Ex. | Starting material | Product structure | Mass spec result | HPLC retention time (method) |
|---|---|---|---|---|
| XXV.1 | ![benzoic acid] | ![Cl-pyrimidine-oxazole-phenyl] | 232 [M + H]$^+$ | 2.22 (S) |
| XXV.2 | ![thiophene carboxylic acid] | ![Cl-pyrimidine-oxazole-thiophene] | 238 [M + H]$^+$ | 1.43 (S) |

Example XXIII 5-(3-Bromophenoxy)-2-methylbentan-2-ol

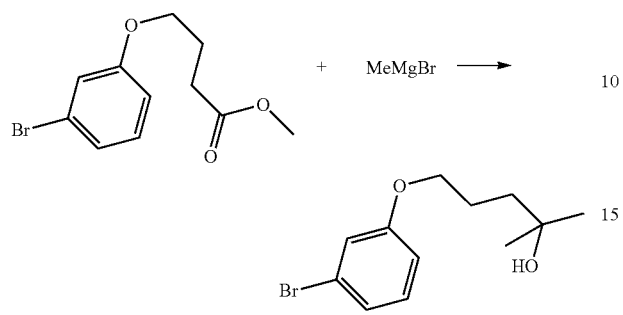

50.2 mL (150 mmol) MeMgBr (3 M in diethylether) are cooled down to 0° C. 24.0 g (75 mmol) of the intermediate XIX.20 are added slowly and after 1 h additional 50 mL THF are added and stirring is continued over night. The reaction mixture is poured onto a ice/aq. HCl mixture and extracted with EtOAc. The org. phases are combined, washed with a sat. aq. NaHCO$_3$ solution and dried with Na$_2$SO$_4$. The solvent is removed in vacuo and the residue is purified by column chromatography (silica gel, CyH/EtOAc 80/20).

C$_{12}$H$_{17}$BrO$_2$ (M=273.2 g/mol)

ESI-MS: 273/275 [m+H]$^+$

R$_t$ (HPLC): 1.51 (method P)

Example XXIV

8-Bromo-5,5-dimethyl-2,3,4,5-tetrahydrobenzo[b]oxepine

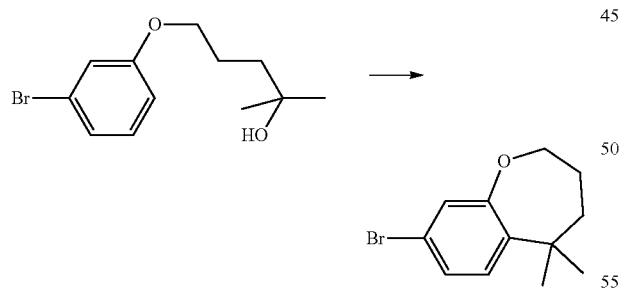

1.09 g (4.00 mmol) of intermediate XXIII are added to 1 l DCM and cooled down to 0° C. 4.26 mL conc. H$_2$SO$_4$ are dropped into the mixture and stirring is continued for 1 h. 300 mL water are added and the phases are separated. The org. phase is washed with sat. aq. NaCl solution, dried with Na$_2$SO$_4$ and the solvent is removed in vacuo.

C$_{12}$H$_{15}$BrO (M=255.2 g/mol)

EI-MS: 254 [M]$^+$

R$_t$ (HPLC): 1.75 (method P)

Example XXV 1-(6-Chloropyridin-3-Acyclopropanecarbonitrile

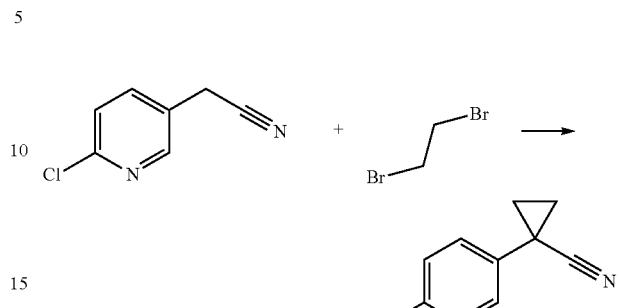

To 32 mL of an aq. NaOH solution (50%) and 32 mL ACN 50.2 mL (150 mmol) are added 6.60 g (21.2 mmol) BnBu$_3$NBr and 3.20 g (21.0 mmol) of 6-chloropyridin-3-yl-acetonitrile. Then 2.17 mL (25.2 mmol) 1,2-dibromoethane are added and the mixture is stirred at r.t. for 20 h. Afterwards the mixture is extracted with EtOAc (2×), the org. phases are combined, washed with water and sat. aq. NaCl solution, dried with MgSO$_4$ and the solvent is removed in vacuo. The residue is purified by column chromatography (silica gel, CyH/EtOAc 95/5→50/50).

C$_9$H$_7$ClN$_2$ (M=178.6 g/mol)

ESI-MS: 179 [M+H]$^+$

Example XXVI 3-(4-Chlorophenyl)-6-iodopyridazine

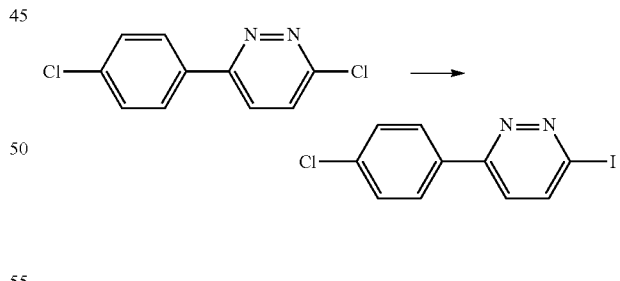

20 mL ACN are added to 0.50 g (1.11 mmol) 3-(4-chlorophenyl)-6-chloropyridazine and 3.33 g (22.2 mmol) NaI before 189 µl fuming conc. HCl are added and the mixture is stirred at 80° C. for 4 h. The mixture is alkalised with aq. ammonia solution (32%) diluted with water and extracted with EtOAc. The org. phases are combined, dried with Na$_2$SO$_4$ and the solvent is removed in vacuo. The resulting crude product is triturated with TBME.

C$_{10}$H$_6$ClIN$_2$ (M=316.5 g/mol)

ESI-MS: 317 [M+H]$^+$

R$_t$ (HPLC): 3.15 (method B)

Example XXVII

Example XXVII.1 (General Route)

2-Bromo-5-ethoxy-pyridine

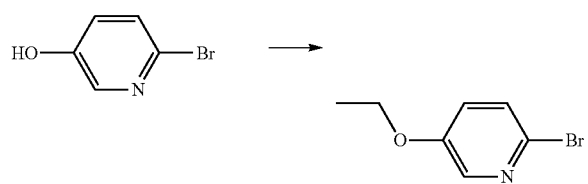

2.51 g (22.99 mmol) 1-bromoethane and 1.99 g (14.37 mmol) $K_2CO_3$ are added to a mixture of 1.0 g (5.75 mmol) 2-bromo-5-hydroxypyridine in 100 mL ACN. The mixture is stirred at reflux over night. Then the reaction mixture is poured onto water and extracted with TBME. The organic layer is dried with $Na_2SO_4$ and the solvent is removed under vacuo. The residue is purified by column chromatography (silica gel, PE/EtOAC 1/1).

$C_7H_8BrNO$ (M=202.1 g/mol)

ESI-MS: 202 $[M+H]^+$ $R_t$ (HPLC): 1.70 min (method F)

The followina compounds are prepared analogously to example XXVII.1

| Ex. | Starting material | Product structure | Mass spec result | HPLC retention time (method) |
|---|---|---|---|---|
| XXVII.1 | HO—[pyridine]—Br | [ethoxy]O—[pyridine]—Br | 202 $[M+H]^+$ | 1.70 (F) |
| XXVII.2 | HO—[pyridine]—Br | [propoxy]O—[pyridine]—Br | 216 $[M+H]^+$ | 1.70 (F) |

Example XXVIII

Example XXVIII.1 (General Route)

5-(4-Iodo-pyridin-2-yloxy)-Pyrimidine

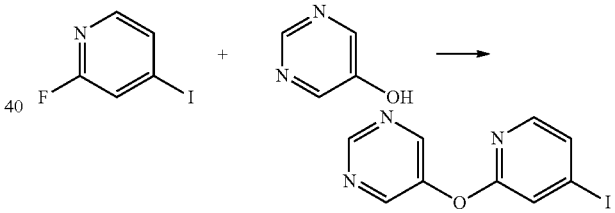

To 259 mg (26.9 mmol) pyrimidin-5-ol (J. Chem. Soc. 1956, 2033) in 200 mL DMF are added 108 mg (26.9 mmol) sodium hydride (60% dispersion in mineral oil). The mixture is stirred for 20 min at r.t. After that time, 500 mg (22.4 mmol) 2-fluoro-4-iodopyridine are added and the mixture is stirred for 12 h at 80° C. Subsequently the mixture is poured into water and extracted with ethyl acetate (3×). The combined organic layers are washed with brine. After drying over sodium sulphate, the solvent is removed in vacuo and the residue is purified by column chromatography (silica gel; heptane/EtOAc, 100/0→40/60).

$C_9H_{61}N_3O$ (M=299.1 g/mol)

ESI-MS: 300 $[M+H]^+$ $R_t$ (HPLC): 2.87 min (method C)

The following compounds are prepared analogously to Example XXVIII.1

For the example XXVIII.2 the reaction mixture is stirred at 50° C. for 4 h.

For the example XXVIII.3 THF is used as solvent and the reaction mixture is stirred at r.t. over night. For the example XXVIII.4 6 eq. of the alcohol and 4 eq. of KOtBu as base are used and the reaction mixture is stirred at r.t. for 3 h.

| Ex. | Starting material | Starting material | Product structure | Mass spec result | HPLC retention time (method) |
|---|---|---|---|---|---|
| XXVIII.1 | 2-fluoro-4-iodopyridine | 5-hydroxypyrimidine | 5-(4-iodopyridin-2-yloxy)pyrimidine | 300 [M + H]+ | 2.87 (C) |
| XXVIII.2 | 4-bromo-2-fluoropyridine | phenol | 4-bromo-2-phenoxypyridine | 249/251 [M + H]+ | 1.12 (K) |
| XXVIII.3 | 5-bromo-2-fluoropyridine | cyclopropylmethanol | 5-bromo-2-(cyclopropylmethoxy)pyridine | 228/230 [M + H]+ | 1.14 (K) |
| XXVIII.4 | 2-chloro-4-fluoro-1-iodobenzene | propanol | 2-chloro-1-iodo-4-propoxybenzene | 296 [M]+ | GC: 4.56 (AA) |
| XXVIII.5 | 4-fluoro-1-iodo-2-methylbenzene | propanol | 1-iodo-2-methyl-4-propoxybenzene | 276 [M]+ | GC: 4.31 (AA) |

Example XXIX and XXX

4-Iodo-2-propoxy-pyridine (XXIX) and 2-chloro-4-propoxypyridine (XXX)

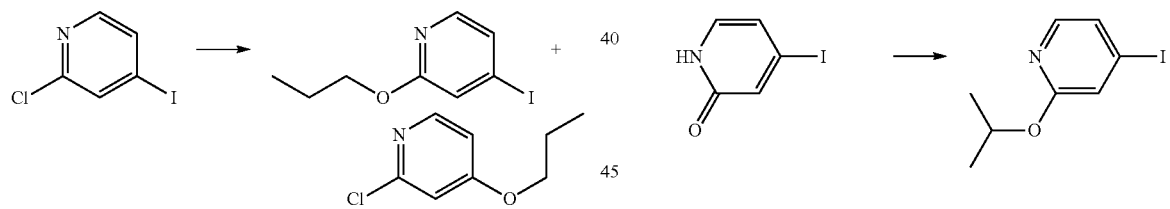

0.58 g (25.06 mmol) sodium are carefully added to 40 mL n-propanol by several portions. The mixture is stirred until the metal is dissolved completely (ca. 45 min). Then 6.00 g (25.1 mmol) 2-chloro-4-iodo-pyridine are slowly added to the mixture. The mixture is stirred at reflux for 3 h. The reaction is quenched by the addition of water. The solvent is removed in vacuo and to the residue are added 20 mL DMF/MeOH. The mixture is filtrated and the filtrate is purified by HPLC (MeOH/H$_2$O/NH$_3$).

4-Iodo-2-propoxy-pyridine (XXIX)

C$_8$H$_{10}$INO (M=263.1 g/mol)
ESI-MS: 264 [M+H]+
R$_t$ (HPLC): 2.22 min (method F)

2-Chloro-4-propoxypyridine (XXX)

C$_8$H$_{10}$ClNO (M=171.6 g/mol)
ESI-MS: 172 [M+H]+
R$_t$ (HPLC): 1.85 min (method F)

Example XXXI

4-Iodo-2-isopropoxy-pyridine

To 2.30 g (10.4 mmol) 4-iodo-1H-pyridin-2-one in 130 mL DCM are added 0.88 mL (11.4 mmol) 2-propanol and 3.00 (11.4 mmol) triphenylphosphine. After cooling down to 0° C. 2.23 mL (11.4 mmol) DIAD are added dropwise. After 5 min the cooling is removed and the mixture is stirred at r.t. for 2 h. The reaction mixture is washed with water and brine, dried with Na$_2$SO$_4$ and the solvent is removed in vacuo. The crude product is purified by column chromatography (silica gel, heptane/EtOAc 90/10).

C$_8$H$_{10}$INO (M=263.1 g/mol)
ESI-MS: 264 [m+H]+
R$_t$(HPLC): 3.72 (method C)

Example XXXII

Example XXXII.1 (General Route)

7-Bromo-8-fluoro-3,4-dihydro-2H-benzo-[1,4]-diox-epine

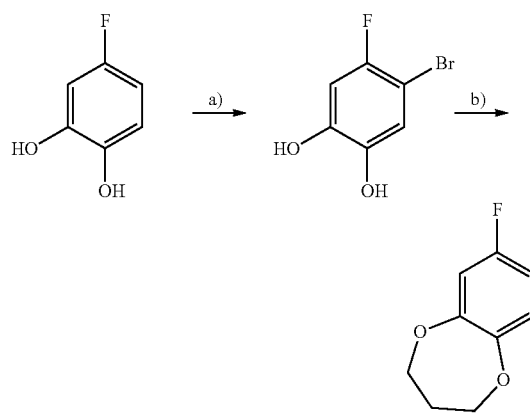

a) To 1.00 g (7.57 mmol) 4-fluorocatechol in 50 mL DCM are added 0.58 mL (11.4 mmol) bromine in 10 mL DCM. The reaction mixture is stirred at r.t. for 3 h. Then the solvent is removed in vacuo and the crude product is purified by column chromatography (silica gel, DCM/MeOH 9/1).

b) To 1.50 g (7.25 mmol) of 4-bromo-5-fluorobenzene-1,2-diol in 25 mL DMF are added 5.90 g (18.1 mmol) $Cs_2CO_3$ and 0.89 mL (8.70 mmol) 1,3-dibromopropane.

The reaction mixture is stirred at 120° C. over night. The solvent is removed in vacuo and to the residue is added water. After extracting several times with EtOAc the org. phases are combined, washed with sat. aq. NaCl solution and dried with $MgSO_4$. The solvent is removed in vacuo and the resulting residue is purified by column chromatography (silica gel, PE/EtOAc 9/1→7/3).

$C_9H_8BrFO_2$ (M=247.1 g/mol)

EI-MS: 246/248 $[M]^+$ $R_f$(TLC): 0.50 (silica gel, PE/EtOAc 4/1)

The following compounds are prepared analogously to example XXXII.1

| Ex. | Starting material | Structure | Mass spec result | TLC Rf-value (silica gel) |
|---|---|---|---|---|
| XXXII.1 | 4-fluoro-catechol | 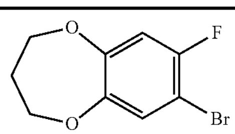 | 246/248 $[M]^+$ | 0.50 (PE/EtOAc 4/1) |
| XXXII.2 | 4-fluoro-catechol | 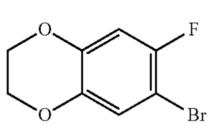 [SMILES: Fc1cc2c(cc1Br)OCCO2] | 232/234 $[M^*]^+$ | 0.59 (PE/EtOAc 4/1) |

Example XXXIII (S)—N-(1-(4-(1-(3-Hydroxyphenyl)azetidin-3-yloxy)phenyl)ethyl)acetamide

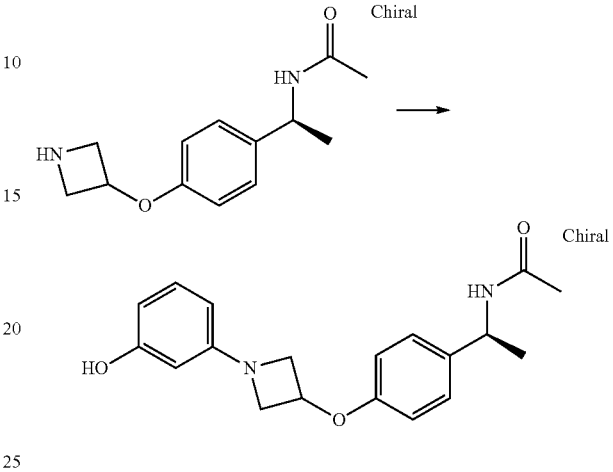

To 0.80 g (2.96 mmol) of the amine XIII.1 in 10 mL dioxane are added 0.31 mL (2.96 mmol) 3-bromophenol, 1.42 g (14.8 mmol) NaOtBu 135 mg (0.15 mmol) $Pd_2$ $dba_3$ and 176 mg (0.59 mmol) 2-(di-tert-butylphosphino)biphenyl. The mixture is degassed thoroughly and stirred at 80° C. for 2 h. Some water is added and the mixture is purified by HPLC (MeOH/$H_2O$/$NH_3$).

$C_{19}H_{22}N_2O_3$ (M=326.4 g/mol)

ESI-MS: 327 $[M+H]^+$ $R_f$(HPLC): 0.86 (method K)

Example XXXIV (S)-1-(4-(1-(5-Bromopyrimidin-2-yl)azetidin-3-yloxy)phenyl)ethylamine

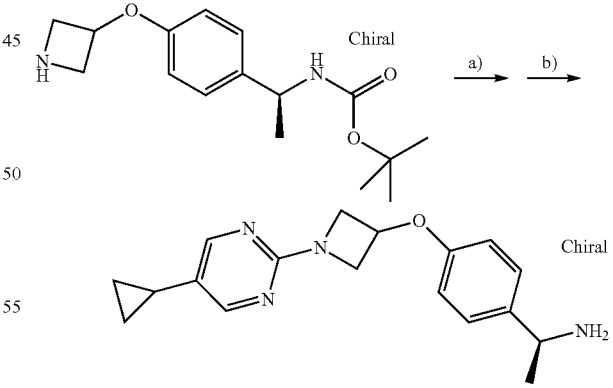

a) 600 mg (2.05 mmol) of the azetidine XV and 317 mg (2.05 mmol) of the pyrimidine XXI.1 are added to 15 mL DMSO and 0.53 mL (3.08 mmol) DIPEA. The mixture is stirred at 35° C. over night and afterwards purified by HPLC (MeOH/$H_2O$/$NH_3$).

b) 550 mg (1.34 mmol) of (S)-tert-butyl 1-(4-(1-(5-bromopyrimidin-2-yl)azetidin-3-yloxy)phenyl)ethylcarbamate are added to 3 mL MeOH and 3.22 mL (4.02 mmol) of a methanolic HCl solution (c=1.3 mol/l). The reaction mixture is stirred at r.t. over night. The solvent is removed in vacuo and the residue is purified by HPLC (MeOH/H$_2$O/NH$_3$).

$C_{18}H_{22}N_4O$ (M=310.4 g/mol)
ESI-MS: 311 [M+H]$^+$
R$_t$ (HPLC): 2.01 min (method A)

Example XXXV (S)-tert-Butyl 1-(4-(1-(4-ethoxyphenyl)azetidin-3-yloxy)phenyl)ethylcarbamate

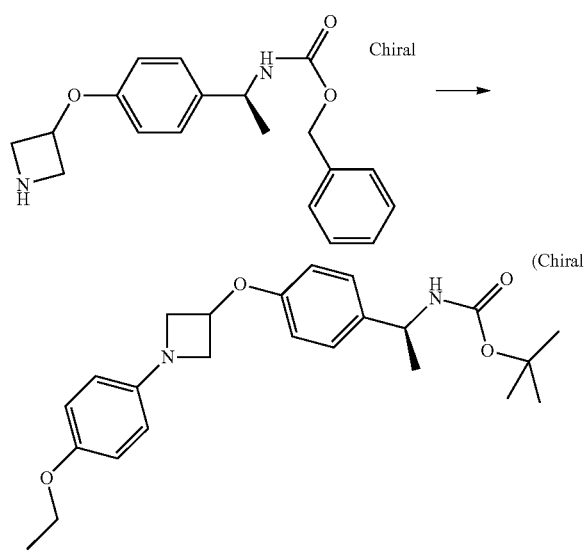

To 360 mg (1.10 mmol) of amine XIII.6 in 10 mL dioxane are added 222 mg (1.10 mmol) 4-bromophenetole, 437 mg (4.41 mmol) NaOtBu, 101 mg (0.11 mmol) Pd$_2$dba$_3$ and 132 mg (0.44 mmol) 2-(di-tert-butylphosphino)biphenyl. The mixture is degassed thoroughly and stirred at 80° C. for 45 min in a microwave oven. A small amount of water and MeOH are added, the mixture is filtered and afterwards purified by HPLC (MeOH/H$_2$O/NH$_3$).

$C_{24}H_{32}N_2O_4$ (M=412.5 g/mol)
ESI-MS: 413 [M+H]$^+$
R$_t$ (HPLC): 2.36 min (method A)

Example XXXVI (S)-1-(4-(1-(4-Ethoxyphenyl)azetidin-3-yloxy)phenyl)ethylamine

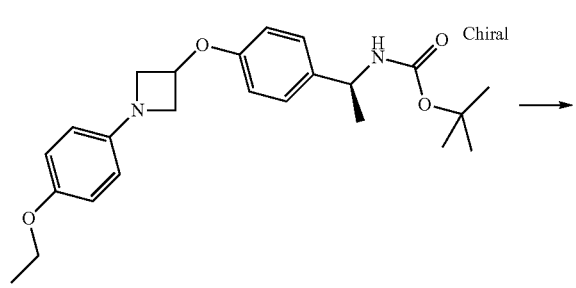

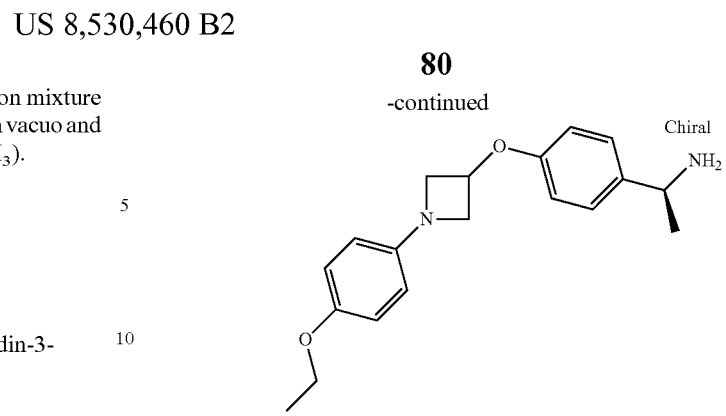

270 mg (0.66 mmol) of the example XXXV are added to 2 mL MeOH and 1.05 mL (1.31 mmol) of a methanolic HCl solution (c=1.3 mol/l). The reaction mixture is stirred at r.t. for 2 h. The solvent is removed in vacuo and to the residue is added diluted aq. NaOH solution. The aq. mixture is extracted with DCM. The org. phase is washed with water, dried with MgSO$_4$ and the solvent is removed in vacuo.

$C_{19}H_{24}N_2O_2$ (M=312.4 g/mol)
ESI-MS: 313 [M+H]$^+$
R$_t$ (HPLC): 0.89 min (method M)

Example XXXVII (S)-Benzyl 1-(4-(1-(2-methoxy-4-propoxyphenyl)azetidin-3-yloxy)phenyl)-ethylcarbamate

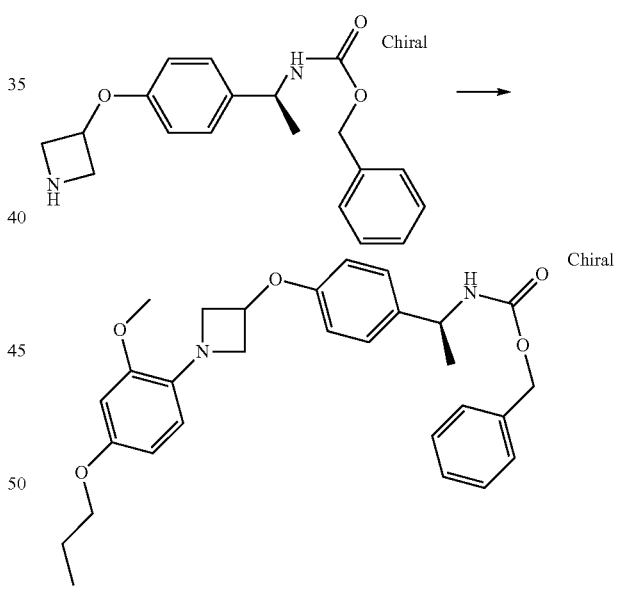

To 3.70 g (8.16 mmol) of amine XIII.5 (used as its HCl salt) in 16 mL toluene and 3 mL tert-butanol are added 2.00 g (8.16 mmol) of the aryl bromide XVI.12, 6.64 g (20.4 mmol) Cs$_2$CO$_3$, 91.6 mg (0.41 mmol) PdOAc$_2$ and 194 mg (0.41 mmol) X-Phos. The mixture is degassed thoroughly and stirred at 120° C. over night. EtOAc and a small amount of water are added and the resulting mixture is filtered, the solvent is removed in vacuo and the residue is purified by HPLC (acetone/H$_2$O/NH$_3$).

$C_{29}H_{34}N_2O_5$ (M=490.6 g/mol)
ESI-MS: 491 [m+H]$^+$
R$_t$ (HPLC): 2.38 min (method G)

Example XXXVIII (S)-1-(4-(1-(2-Methoxy-4-propoxyphenyl)azetidin-3-yloxy)phenyl)ethylamine

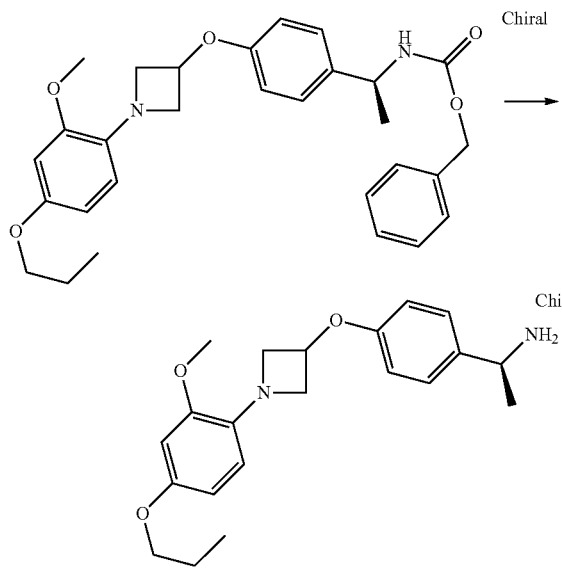

1.70 g (3.47 mmol) of example XXXVII is added to 50 mL MeOH and charged with 100 mg Pd/C (10%). The reaction mixture is hydrogenated at r.t. at a hydrogen pressure of 2 bar. Then the reaction mixture is filtered, the solvent is removed in vacuo and the residue is purified by HPLC (acetone/H$_2$O/NH$_3$).

$C_{21}H_{28}N_2O_3$ (M=356.5 g/mol)

ESI-MS: 357 [M+H]$^+$
R$_t$ (HPLC): 2.20 min (method A)

Example XXXIX

Example XXXIX.1 (General Route)

(S)—N-(1-(4-(1-(2-Chloropyrimidin-4-yl)azetidin-3-yloxy)phenyl)ethyl)acetamide

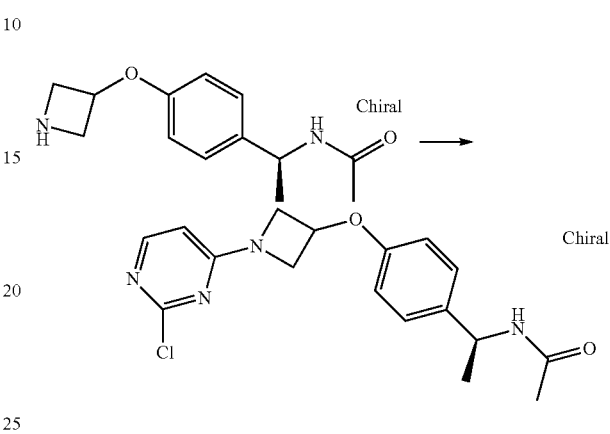

1.00 g (3.69 mmol) of the azetidine XIII.6 and 605 mg (4.06 mmol) of 2,4-dichloropyrimidine are added to 30 mL DMSO and 0.57 mL (4.06 mmol) TEA. The mixture is stirred at r.t. over night, the solvent is removed in vacuo and the residue is purified by HPLC (MeOH/H$_2$O/NH$_3$).

$C_{17}H_{19}ClN_4O_2$ (M=346.8 g/mol)
ESI-MS: 347 [M+H]$^+$
R$_t$ (HPLC): 0.84 min (method K)

The following compounds are prepared analogously to example XXXIX.1.1

For the example XXXIX.2 the reaction mixture is stirred at r.t. for 3 h.

| Ex. | Starting material(s) | Structure | Mass spec result | HPLC retention time (method) |
|---|---|---|---|---|
| XXXIX.1 | XIII.6 | 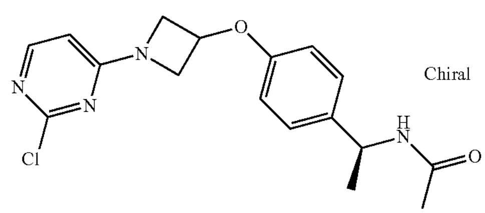 [SMILES: CC(=O)N[C@@H](C)c1ccc(OC2CN(c3ccnc(Cl)n3)C2)cc1] | 347 [M + H]$^+$ | 0.84 (K) |
| XXXIX.2 | XIII.6 | 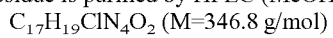 | 347 [M + H]$^+$ | 0.87 (K) |

Example XL

Example XL.1 (General Route)

3-Bromo-6-ethoxy-pyridine-2-carbonitrile

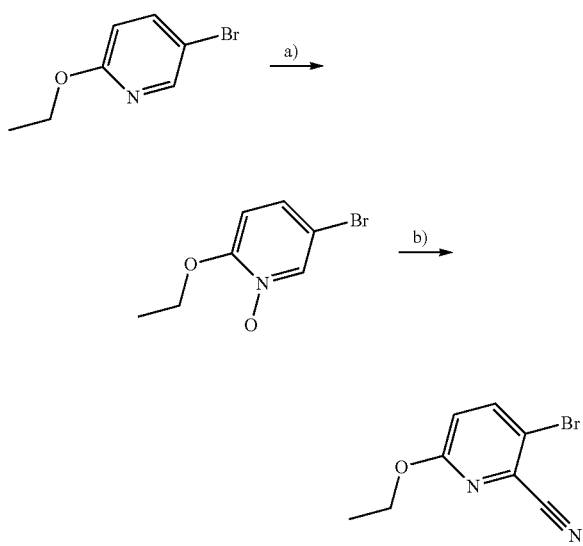

a) To 4.50 g (22.3 mmol) of 3-bromo-6-ethoxy-pyridine in 100 mL DCM are added 20.5 g (89.1 mmol) mCPBA by several portions. The reaction mixture is stirred at r.t. over night, charged with MgSO$_4$ and filtered over 100 g of basic aluminium oxide. The solvent is removed in vacuo before DCM and an aq. NaHCO$_3$ solution are added and the layers are separated. The aq. layer is saturated with NaCl and extracted several times with DCM. The org. layers are combined and the solvent is removed in vacuo. The residue is filtered through a plug of silica gel.

b) 1.00 g (4.59 mmol) 5-bromo-2-ethoxy-pyridine 1-oxide, 2.46 mL (18.3 mmol) trimethylsilyl cyanide and 1.92 mL (13.8 mmol) TEA in 10 mL ACN are stirred together at 100° C. for 24 h. Then the volatile components are removed in vacuo and the residue is dissolved in DCM, washed with aq. NaHCO$_3$ solution, dried with MgSO$_4$ and filtered through a plug of silica gel. Then the solvent is removed in vacuo.

$C_8H_7BrN_2O$ (M=227.1 g/mol),

ESI-MS: 227/229 [M+H]$^+$ $R_f$(TLC): 0.85 (silica gel, PE/EtOAc 7/3)

The following compounds are prepared analogously to example XL.1.

For the examples XL.2 and XL.3 the intermediates from step a are purified by HPLC after the filtration over basic aluminium oxide.

| Example | Starting material | Product structure | Mass spec result | $R_t$ (HPLC) [min] (method) |
|---|---|---|---|---|
| XL.1 | | | 227/229 [M + H]$^+$ | TLC: Rf = 0.85 (silica gel, PE/EtOAc 7/3) |
| XL.2 | | | 241/243 [M + H]$^+$ | 1.09 (K) |
| XL.3 | | | 275/277 [M + Na]$^+$ | 1.08 (K) |

Example XLI

Example XLI.1 (General Route)

2-Chloro-5-((2,2-difluorocyclopropyl)methoxy)pyrimidine

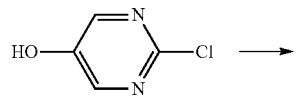

295 mg (1.72 mmol) 1-bromomethyl-2,2-difluorocyclopropane and 318 mg (2.30 mmol) K₂CO₃ are added to a mixture of 150 mg (1.15 mmol) 2-chloro-5-hydroxypyrimidine in 2 mL DMF. The mixture is stirred at 80° C. over night. Then the reaction mixture is quenched by the addition of water and extracted with DCM. The organic layer is dried with Na₂SO₄ and the solvent is removed in vacuo. The residue is purified by HPLC (MeOH/H₂O/NH₃).

$C_8H_7ClF_2N_2O$ (M=220.6 g/mol)
ESI-MS: 221 [M+H]⁺
$R_t$ (HPLC): 1.21 min (method V)

The following compounds are prepared analogously to example XLI.1.

| Example | Starting material | Product structure | Mass spec result | $R_t$ (HPLC) [min] (method) |
|---|---|---|---|---|
| XLI.1 | | | 221 [M + H]⁺ | 1.21 (V) |
| XLI.2 | | | 173 [M + H]⁺ | 1.47 (A) |

Example XLII

4-Bromo-2-ethoxy-5-fluoropyridine 2.08 mL (26.0 mmol) Ethyliodide and 1.08 g (3.91 mmol) Ag₂CO₃ are added to a mixture of 500 mg (2.160 mmol) 4-bromo-5-fluoro-pyridin-2-ol in 10 mL DCM. The mixture is stirred at r.t. over night. Then the reaction mixture is quenched by the addition of water and DCM. After filtration the org. layer is separated, dried with Na₂SO₄ and the solvent is removed in vacuo.

$C_7H_7BrFNO$ (M=220.0 g/mol)
ESI-MS: 220 [M+H]⁺
$R_t$ (HPLC): 1.27 min (method X)

Example XLIII

5-tert-Butyl-2-chloropyrimidine

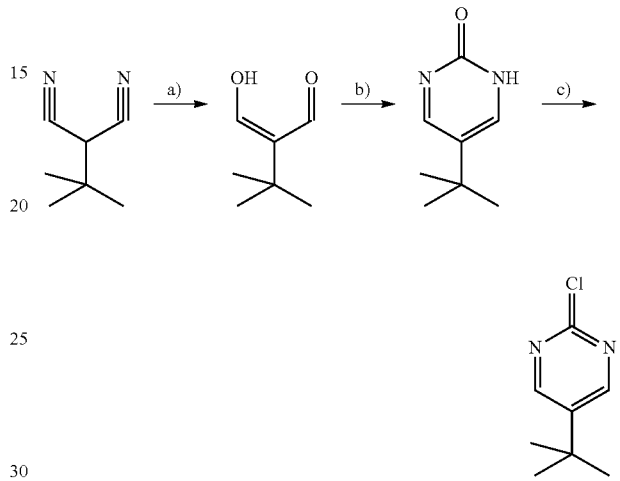

a) 25.0 g (0.21 mol) tert-Butylmalononitrile and 150 mL toluene are cooled down to −60° C. and 400 mL DIBALH (c=1.5 mol/l in toluene) are carefully added. The reaction mixture is warmed to r.t. and stirred for 4 h. The reaction is quenched by the addition of aq. HCl solution (c=1 mol/l). The resulting mixture is extracted with EtOAc, the org. layers are combined, dried with Na₂SO₄ and the solvent is removed in vacuo. The crude product is used without further purification.

b) 25 mL Hydrochloric acid (c=10 mol/l) are added to a mixture of 5.62 g (0.09 mol) urea and 200 mL ethanol. The mixture is stirred for 10 min and then treated with 10.0 g of the above mentioned crude product. The resulting mixture is heated at reflux for 40 h, then concentrated and dried with toluene. The crude product is used without further purification.

c) 200 mL POCl₃ and 14 g (0.09 mol) 5-tert-butylpyrimidin-2(1H)-one are heated in a sealed glass ampoule for 3 h at 160° C. The mixture is cooled and the excess POCl₃ is removed in vacuo and the residue is treated with water and basified to pH 10 with aq. NaOH solution (c=3 mol/l). The mixture is extract with DCM, dried with Na$_2$SO$_4$ and the solvent is removed in vacuo. The crude product is purified by flash column chromatography (silica gel, DCM/MeOH 98/2).

C$_8$H$_{11}$ClN$_2$ (M=170.6 g/mol)
EI-MS: 171 [M]$^+$
R$_t$ (HPLC): 6.34 (method W)

Example XLIV

Example XLIV.1 (General Route)

N-[1-(4-Bromo-3-fluoro-phenyl)-ethyl]-acetamide

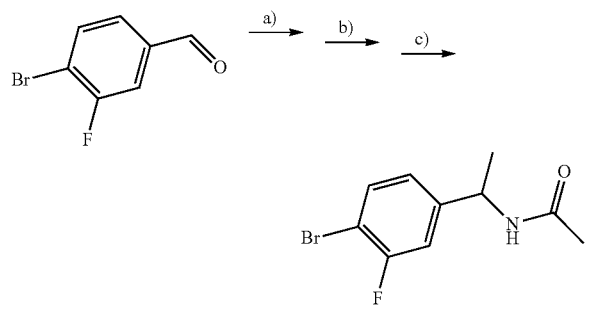

a) 11.1 g (91.0 mmol) 2-Methyl-2-propanesulfinamide are added to 16.5 g (76.0 mmol) 4-bromo-3-fluoro-benzaldehyde and 34.6 g (152 mmol) titanium(IV) ethoxide in 100 mL THF. Stirring is continued for 1.5 h at 50° C. After that time, the mixture is poured into brine. The mixture is filtered over celite and the filtrate is transferred to a separation funnel. The organic layer is separated, dried over magnesium sulphate and the solvent is removed by evaporation. The residue is purified by column chromatography (silica gel; gradient hexane/EtOAc 1:0→3:2) to yield the desired product.

C$_{11}$H$_{13}$BrFNOS (M=306.2 g/mol),
ESI-MS: 306/308 [M+H]$^+$
R$_f$ (TLC): 0.30 (silica gel, hexane/EtOAc 4:1)

b) Under inert gas atmosphere 37.2 mL (112 mmol) of a 3N solution of methyl magnesium bromide in THF are added dropwise to 17.1 g (55.8 mmol) 2-methyl-propane-2-sulfonic acid 4-bromo-3-fluoro-benzylideneamide (IX.1) in 170 mL THF at −78° C. The cooling bath is removed and stirring is continued for 2 h. After that time, the mixture is poured into sat. NH$_4$Cl-solution (300 mL) and extracted with EtOAc.

The organic layer is separated, washed with brine and dried over sodium sulphate. The solvent is removed by evaporation to yield the desired product.

C$_{12}$H$_{17}$BrFNOS (M=322.2 g/mol)
ESI-MS: 322/324 [M+H]$^+$ c) 20.0 mL 4N HCl in dioxane are added to 17.2 g (53.4 mmol) 2-methyl-propane-2-sulfonic acid [1-(4-bromo-3-fluoro-phenyl)-ethyl]-amide (X.1) in 150 mL MeOH. Stirring is continued for 1 h. After that time, the mixture is concentrated and the residue is triturated from diethylether (150 mL). The precipitate is filtered off, washed with diethylether and suspended in 250 mL DCM. 8.64 mL (107 mmol) pyridine and 5.29 mL (56.1 mmol) acetic anhydride are added and the mixture is stirred for 12 h at rt. After that time, the mixture is transferred to a separation funnel, washed with 1N HCl (200 mL) and sat. aq. NaHCO$_3$-solution (200 mL) and dried over sodium sulphate. The solvent is removed by evaporation to yield the desired product.

C$_{10}$H$_{ii}$BrFNO (M=260.1 g/mol)
ESI-MS: 260/262 [M+H]$^+$
R$_t$ (HPLC): 2.60 min (method Y)

Example XLV

N-[1-(4-Hydroxy-3-fluoro-phenyl)-ethyl]-acetamide

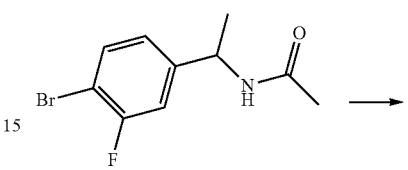

Under inert gas atmosphere 200 mg (0.77 mmol) of example III are added to a 1/1 mixture of dioxane and water. Then 240 mg (4.20 mmol) powdered KOH and 58.7 mg (0.12 mmol) 2-di-tert-butylphosphino-3,4,5,6-tetramethyl-2',4',6'-triisopropyl-1,1'-biphenyl are added and the mixture is degassed before 36.6 mg (0.04 mmol)

Pd$_2$(dba)$_3$ are added and the mixture is stirred at 140° C. for 10 min in a microwave oven. After cooling down, the reaction mixture is diluted with EtOAc, washed with an aq. HCl solution (c=4 mol/L) and a sat. aq. NaCl solution, dried over MgSO$_4$, filtered and the solvent is removed in vacuo. The resulting crude product is purified by HPLC (ACN/H$_2$O/TFA).

C$_{10}$H$_{12}$FNO$_2$ (M=197.2 g/mol)
ESI-MS: 198 [m+H]$^+$
R$_t$ (HPLC): 0.55 min (method AA)

Example XLVI (S)—N-(1-(5-Hydroxypyridin-2-yl)ethyl)acetamide

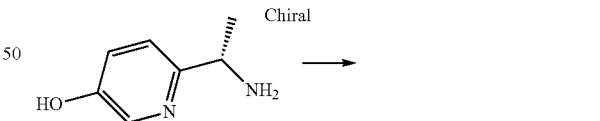

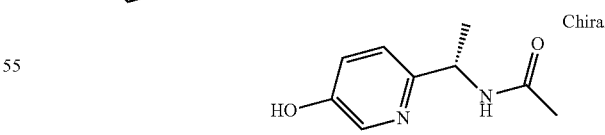

To 1.00 g (5.73 mmol) (S)-6-(1-aminoethyl)pyridin-3-ol in 10 ml THF and 3.99 mL TEA (28.6 mmol) are slowly added 494 mg (6.30 mmol) acetyl chloride and stirring is continued for 2 h. The reaction is quenched by the addition of water and extracted several times with DCM. The org. layers are combined, dried over MgSO$_4$, filtered and the solvent is removed in vacuo. The crude product is purified by column chromatography (silica gel, DCM/MeOH/NH$_3$ 90/9/1).

C₉H₁₂N₂O₂ (M=180.2 g/mol)
ESI-MS: 181 [m+H]⁺
R_t (HPLC): 0.15 min (method Z)

Example XLVII 1-(4-(Cyclopropylmethoxy)phenyl)azetidin-3-ol

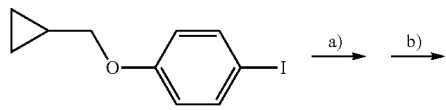

a) 6.50 g (26.0 mmol) 3-(tert-butyldimethylsilyloxy)azetidine, 7.13 g (26.0 mmol) of 1-(cyclopropylmethoxy)-4-iodobenzene (WO2012/028676), 10.0 g (104 mmol) NaOtBu and 1.54 g (2.08 mmol) chloro(2-dicyclohexylphosphino-2',4',6'-triisopropyl-1,1'-biphenyl)(2-(2-aminoethyl)-phenyl)-palladium (II) are added to 65 mL dioxane and stirred at 75° C. for 2.5 h under inert gas atmosphere. Water is added and the resulting mixture is extracted with EtOAc. The org. layers are combined, dried over MgSO₄, filtered and the solvent is removed in vacuo. The resulting crude product is purified by HPLC (ACN/H₂O/NH₃).

C₁₉H₃₁N₂O₂Si (M=333.5 g/mol)
ESI-MS: 334 [M+H]⁺
R_t (HPLC): 1.46 min (method K)

b) To 3.65 g (10.9 mmol) of the above mentioned product in 60 mL THF are added 3.36 g (12.0 mmol) tetrabutylammoniumfluoride monohydrate and the mixture is stirred at r.t. over night. 150 mL of a half saturated aq. NaHCO₃ solution is added and the resulting mixture is extracted with TBME (3×). The org. layers are combined, washed with diluted aq. NaHCO₃ solution, dried over MgSO₄, filtered and the solvent is removed in vacuo. The resulting crude product is purified by HPLC (MeOH/H₂O/NH₃).

C₁₃H₁₇NO₂ (M=219.3 g/mol)
ESI-MS: 220 [M+H]⁺
R_t (HPLC): 0.76 min (method AB)

Example XLVIII 1-(4-(Cyclopropylmethoxy)phenyl)azetidin-3-yl methanesulfonate

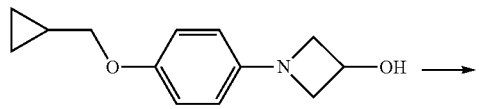

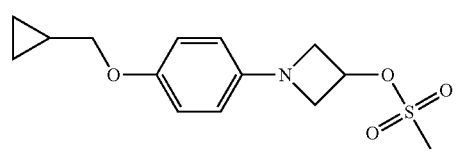

To 1.50 g (6.84 mmol) of the above mentioned product in 10 mL DCM are added 2.38 mL (17.1 mmol) TEA and 635 µL (8.21 mmol) methanesulfonyl chloride and the mixture is stirred at r.t. for 1 h. Water is added and the mixture is extracted with DCM. The org. layers are combined, washed with brine, dried over MgSO₄, filtered and the solvent is removed in vacuo. The resulting crude product is triturated with diethylether.

C₁₄H₁₉NO₄S (M=297.4 g/mol)
ESI-MS: 298 [M+H]⁺
R_t (HPLC): 0.86 min (method AB)

Preparation of Final Compounds

Example 1

Example 1.1 (General Route)

N-(1-(4-(1-(4-tert-Butylphenyl)azetidin-3-yloxy)phenyl)ethyl)acetamide

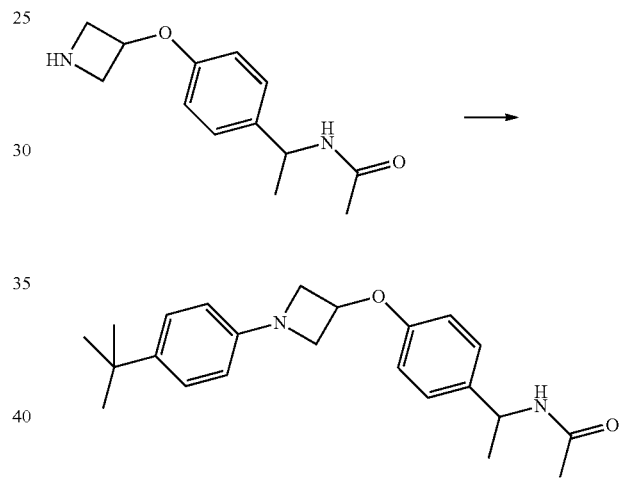

To 120 mg (0.51 mmol) of amine XIII.2 in 2.5 mL 1,4-dioxane are added 100 µl (0.56 mmol) 1-bromo-4-tert-butylbenzene, 203 mg (2.05 mmol) NaOtBu, 46.9 mg (0.05 mmol) Pd₂dba₃ and 61.1 mg (0.21 mmol) 2-(di-tert-butylphosphino)biphenyl. The mixture is degassed thoroughly and stirred at 45° C. over night. A small amount of water and MeOH is added, the mixture is filtered and afterwards purified by HPLC (MeOH/H₂O/NH₃).

C₂₃H₃₀N₂O₂ (M=366.5 g/mol)
ESI-MS: 367 [M+H]⁺
R_t (HPLC): 1.32 min (method L)

The following compounds are prepared analogously to example 1.1:

For the examples 1.26-1.31 and 1.53-1.54 the amount of amine in dioxane/DMF is added to the appropriate arylbromide and the reaction mixture is stirred at 45° C. for 3d For the examples 1.32-1.35 the reaction temperature is 50° C.

For the examples 1.36-1.43 and 1.55 the reactions are done in a microwave oven at 80° C. for 45 min.

For the examples 1.44-1.52 the reaction mixtures are stirred at 80-90° C. for 1-2 h.

| Ex. | Starting material(s) | Structure | Mass spec result | HPLC retention time (method) |
|---|---|---|---|---|
| 1.1 | XIII.2 | 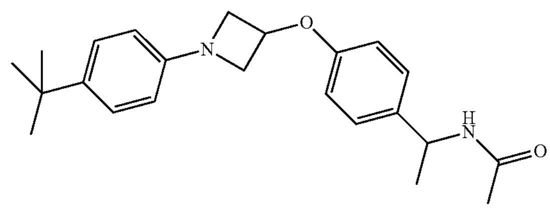 [SMILES: CC(=O)NC(C)c1ccc(OC2CN(c3ccc(C(C)(C)C)cc3)C2)cc1] | 367 [M + H]⁺ | 1.32 (L) |
| 1.2 | XIII.2 | 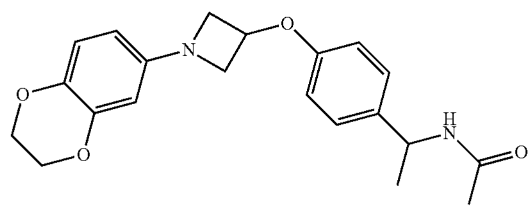 [SMILES: CC(=O)NC(C)c1ccc(OC2CN(c3ccc4c(c3)OCCO4)C2)cc1] | 369 [M + H]⁺ | 1.83 (A) |
| 1.3 | XIII.2 + XVII.1 | 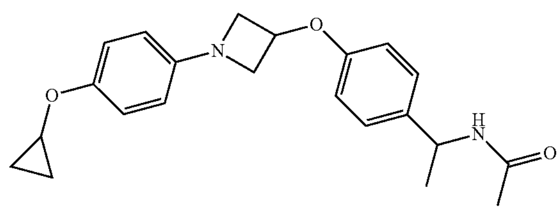 [SMILES: CC(=O)NC(C)c1ccc(OC2CN(c3ccc(OC4CC4)cc3)C2)cc1] | 367 [M + H]⁺ | 2.00 (A) |
| 1.4 | XIII.2 + XVI.2 | 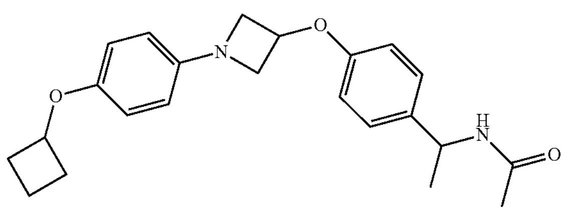 [SMILES: CC(=O)NC(C)c1ccc(OC2CN(c3ccc(OC4CCC4)cc3)C2)cc1] | 381 [M + H]⁺ | 2.09 (A) |
| 1.5 | XIII.2 | 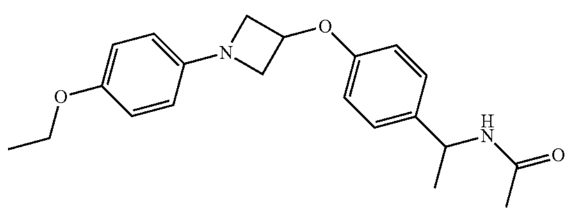 [SMILES: CCOc1ccc(N2CC(Oc3ccc(C(C)NC(C)=O)cc3)C2)cc1] | 355 [M + H]⁺ | 1.95 (A) |
| 1.6 | XIII.2 + XVI.3 | 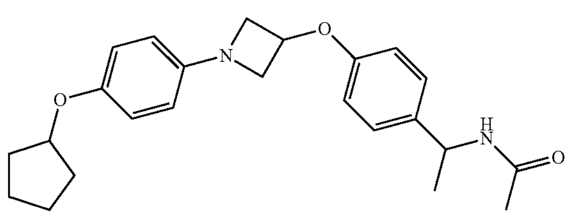 [SMILES: CC(=O)NC(C)c1ccc(OC2CN(c3ccc(OC4CCCC4)cc3)C2)cc1] | 395 [M + H]⁺ | 2.16 (A) |
| 1.7 | XIII.2 | 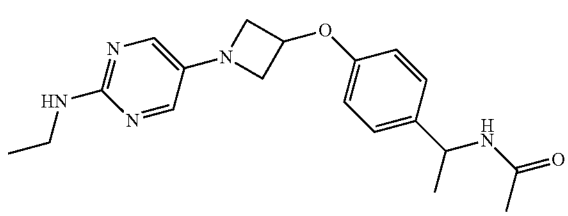 [SMILES: CCNc1ncc(N2CC(Oc3ccc(C(C)NC(C)=O)cc3)C2)cn1] | 356 [M + H]⁺ | 1.62 (A) |

-continued

| Ex. | Starting material(s) | Structure | Mass spec result | HPLC retention time (method) |
|---|---|---|---|---|
| 1.8 | XIII.2 | 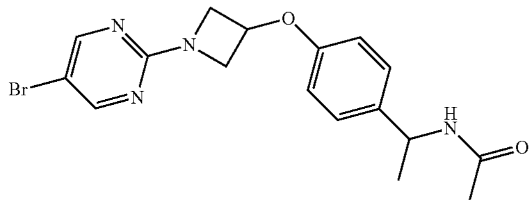 [SMILES: CC(=O)NC(C)c1ccc(OC2CN(c3ncc(Br)cn3)C2)cc1] | 391/393 [M + H]⁺ | 1.87 (A) |
| 1.9 | XIII.2 | 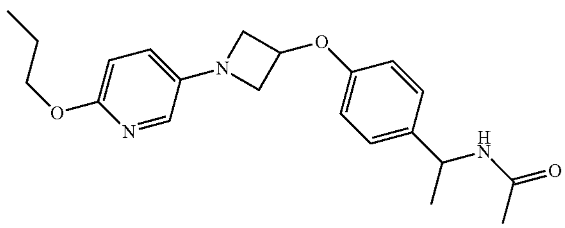 [SMILES: CCCOc1ccc(N2CC(Oc3ccc(C(C)NC(C)=O)cc3)C2)cn1] | 370 [M + H]⁺ | 2.00 (A) |
| 1.10 | XIII.2 + XVIII | 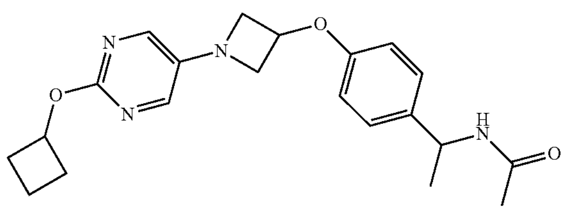 [SMILES: CC(=O)NC(C)c1ccc(OC2CN(c3cnc(OC4CCC4)nc3)C2)cc1] | 383 [M + H]⁺ | 1.91 (A) |
| 1.11 | XIV | 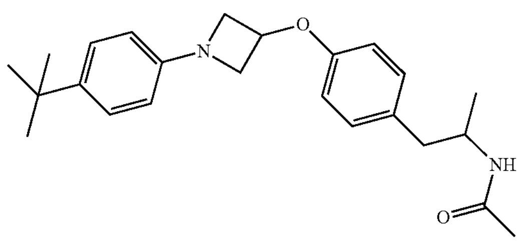 [SMILES: CC(=O)NC(C)Cc1ccc(OC2CN(c3ccc(C(C)(C)C)cc3)C2)cc1] | 381 [M + H]⁺ | 2.36 (F) |
| 1.12 | XIV | 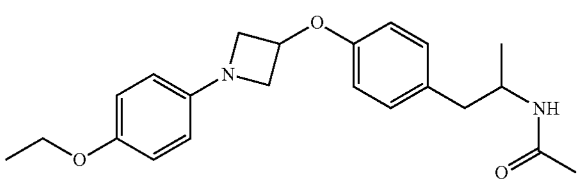 [SMILES: CCOc1ccc(N2CC(Oc3ccc(CC(C)NC(C)=O)cc3)C2)cc1] | 369 [M + H]⁺ | 2.10 (F) |
| 1.13 | XIII.1 | Chiral | 369 [M + H]⁺ | 2.09 (A) |
| 1.14 | XIII.1 + XVI.1 | Chiral | 381 [M + H]⁺ | 2.06 (A) |

-continued

| Ex. | Starting material(s) | Structure | | Mass spec result | HPLC retention time (method) |
|---|---|---|---|---|---|
| 1.15 | XIII.1 + XIX | 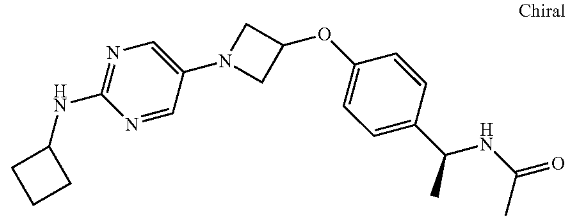 [SMILES: CC(=O)N[C@@H](C)c1ccc(OC2CN(c3cnc(NC4CCC4)nc3)C2)cc1] | Chiral | 382 [M + H]⁺ | 1.81 (A) |
| 1.16 | XIII.1 | 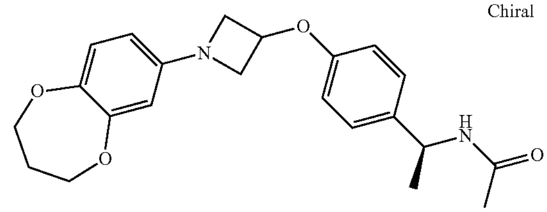 [SMILES: CC(=O)N[C@@H](C)c1ccc(OC2CN(c3ccc4c(c3)OCCCO4)C2)cc1] | Chiral | 383 [M + H]⁺ | 1.86 (A) |
| 1.17 | XIII.1 + XVI.8 | 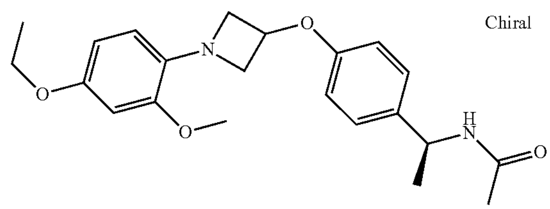 [SMILES: CCOc1ccc(N2CC(Oc3ccc([C@H](C)NC(C)=O)cc3)C2)c(OC)c1] | Chiral | 385 [M + H]⁺ | 1.98 (A) |
| 1.18 | XIII.1 + XVI.18 | 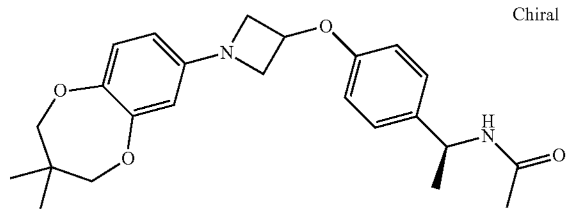 [SMILES: CC(=O)N[C@@H](C)c1ccc(OC2CN(c3ccc4c(c3)OCC(C)(C)CO4)C2)cc1] | Chiral | 411 [M + H]⁺ | 2.11 (A) |
| 1.19 | XIII.1 | 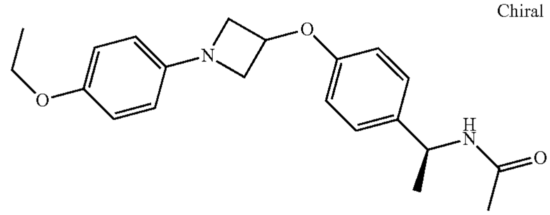 [SMILES: CCOc1ccc(N2CC(Oc3ccc([C@H](C)NC(C)=O)cc3)C2)cc1] | Chiral | 355 [M + H]⁺ | 1.96 (A) |
| 1.20 | XIII.1 + XVI.9 | 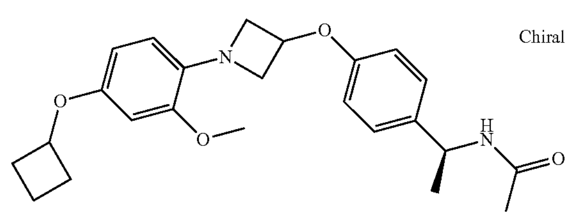 [SMILES: COc1cc(OC2CCC2)ccc1N1CC(Oc2ccc([C@H](C)NC(C)=O)cc2)C1] | Chiral | 411 [M + H]⁺ | 2.13 (A) |

US 8,530,460 B2

97                                                                                    98

-continued

| Ex. | Starting material(s) | Structure | Mass spec result | HPLC retention time (method) |
|---|---|---|---|---|
| 1.21 | XIII.1 + XVI.12 | Chiral | 399 [M + H]⁺ | 2.10 (A) |
| 1.22 | XIII.1 | Chiral | 366 [M + H]⁺ | 1.89 (A) |
| 1.23 | XIII.1 | Chiral | 404 [M + H]⁺ | 2.07 (A) |
| 1.24 | XIII.1 | Chiral | 369 [M + H]⁺ | 1.84 (A) |
| 1.25 | XIII.1 + XVI.14 | Chiral | 394 [M + H]⁺ | 2.12 (A) |
| 1.26 | XIII.1 | Chiral | 391 [M + H]⁺ | 2.12 (A) |

-continued

| Ex. | Starting material(s) | Structure | Mass spec result | HPLC retention time (method) |
|---|---|---|---|---|
| 1.27 | XIII.1 | Chiral | 366 [M + H]⁺ | 1.87 (A) |
| 1.28 | XIII.1 | Chiral | 428 [M + H]⁺ | 2.20 (A) |
| 1.29 | XIII.1 + XXIV | Chiral | 409 [M + H]⁺ | 2.25 (A) |
| 1.30 | XIII.1 | Chiral | 355 [M + H]⁺ | 2.03 (A) |
| 1.31 | XIII.5 | Chiral | 398 [M + H]⁺ | 2.21 (G) |
| 1.32 | XIII.5 + XVII.1 | Chiral | 396 [M + H]⁺ | 2.14 (G) |

-continued

| Ex. | Starting material(s) | Structure | Mass spec result | HPLC retention time (method) |
|---|---|---|---|---|
| 1.33 | XIII.5 + XVI.1 | 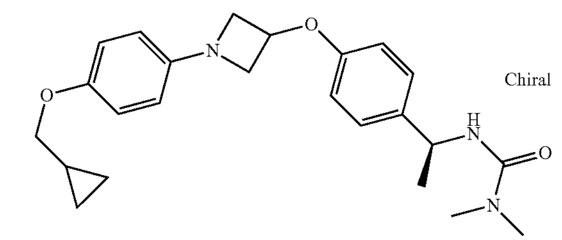 [SMILES: C[C@H](NC(=O)N(C)C)c1ccc(OC2CN(c3ccc(OCC4CC4)cc3)C2)cc1] | 410 [M + H]+ | 2.18 (G) |
| 1.34 | XIII.5 | 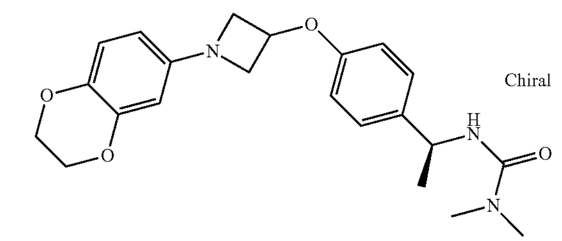 [SMILES: C[C@H](NC(=O)N(C)C)c1ccc(OC2CN(c3ccc4c(c3)OCCO4)C2)cc1] | 398 [M + H]+ | 1.98 (G) |
| 1.35 | XIII.4 | 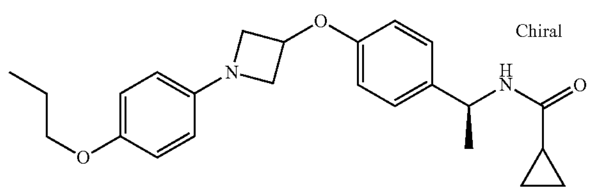 [SMILES: CCCOc1ccc(N2CC(Oc3ccc([C@H](C)NC(=O)C4CC4)cc3)C2)cc1] | 395 [M + H]+ | 1.11 (M) |
| 1.36 | XIII.1 + XVI.11 | 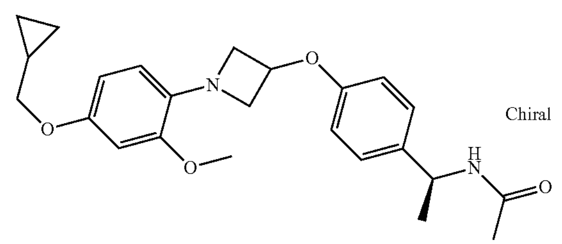 [SMILES: COc1cc(OCC2CC2)ccc1N1CC(Oc2ccc([C@H](C)NC(C)=O)cc2)C1] | 411 [M + H]+ | 1.17 (K) |
| 1.37 | XIII.1 + XVI.13 | 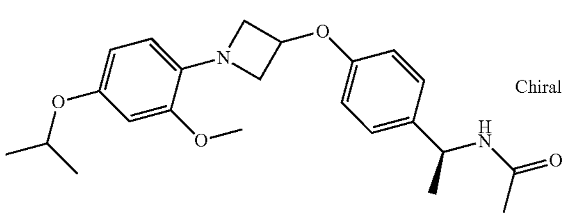 [SMILES: COc1cc(OC(C)C)ccc1N1CC(Oc2ccc([C@H](C)NC(C)=O)cc2)C1] | 399 [M + H]+ | 1.05 (K) |
| 1.38 | XIII.1 + XVI.10 | 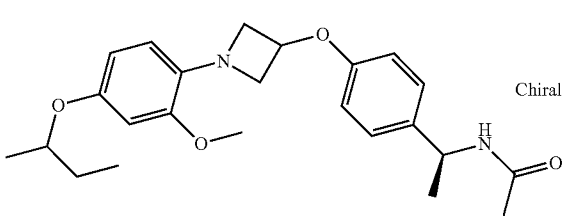 [SMILES: CCC(C)Oc1ccc(N2CC(Oc3ccc([C@H](C)NC(C)=O)cc3)C2)c(OC)c1] | 413 [M + H]+ | 1.13 (K) |

-continued
| Ex. | Starting material(s) | Structure | Mass spec result | HPLC retention time (method) |
|---|---|---|---|---|
| 1.39 | XIII.4 + XVII.1 | 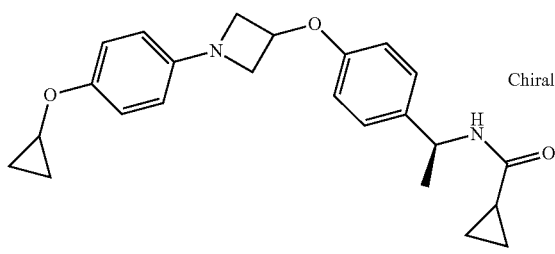 [SMILES: C[C@H](NC(=O)C1CC1)c1ccc(OC2CN(c3ccc(OC4CC4)cc3)C2)cc1] | 393 [M + H]⁺ | 1.15 (K) |
| 1.40 | XIII.4 + XVI.1 | 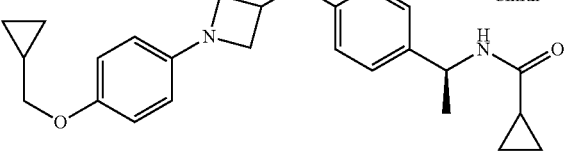 | 407 [M + H]⁺ | 1.20 (K) |
| 1.41 | XIII.4 | 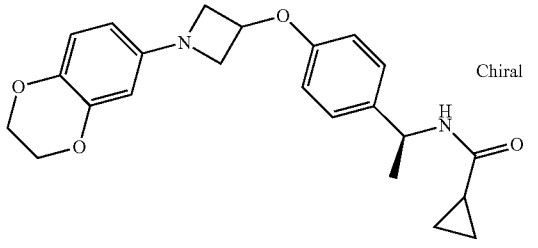 [SMILES: C[C@H](NC(=O)C1CC1)c1ccc(OC2CN(c3ccc4c(c3)OCCO4)C2)cc1] | 395 [M + H]⁺ | 1.07 (K) |
| 1.42 | XIII.5 | 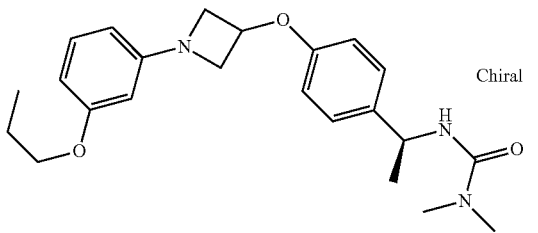 [SMILES: CCCOc1cccc(N2CC(Oc3ccc([C@H](C)NC(=O)N(C)C)cc3)C2)c1] | 398 [M + H]⁺ | 1.23 (K) |
| 1.43 | XIII.6 + XVII.3 | 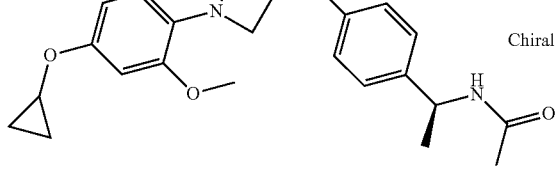 | 397 [M + H]⁺ | 1.13 (K) |
| 1.44 | XIII.6 + XVII.2 | 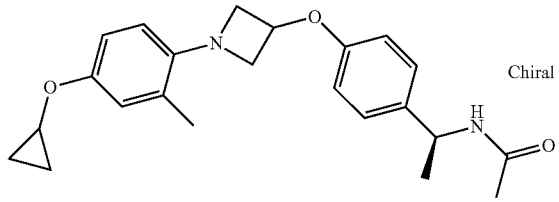 [SMILES: CC(=O)N[C@@H](C)c1ccc(OC2CN(c3ccc(OC4CC4)cc3C)C2)cc1] | 381 [M + H]⁺ | 1.16 (K) |

-continued

| Ex. | Starting material(s) | Structure | Mass spec result | HPLC retention time (method) |
|---|---|---|---|---|
| 1.45 | XIII.6 + XVII.4 | Chiral | 403 [M + H]⁺ | 1.23 (K) |
| 1.46 | XIII.6 + XVI.16 | Chiral | 406 [M + H]⁺ | 1.19 (K) |
| 1.47 | XIII.6 + XVI.15 | Chiral | 406 [M + H]⁺ | 1.16 (K) |
| 1.48 | XIII.6 + XVI.4 | Chiral | 369 [M + H]⁺ | 1.20 (K) |
| 1.49 | XIII.6 + XVI.5 | Chiral | 383 [M + H]⁺ | 1.30 (K) |
| 1.50 | XIII.6 | Chiral | 383 [M + H]⁺ | 1.17 (K) |
| 1.51 | XIII.1 + XXVII.1 | Chiral | 356 [M + H]⁺ | 1.82 (A) |

-continued

| Ex. | Starting material(s) | Structure | Mass spec result | HPLC retention time (method) |
|---|---|---|---|---|
| 1.52 | XIII.1 + XXVII.2 | 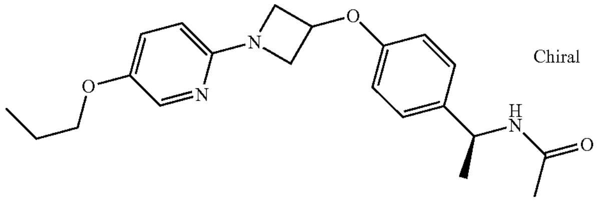 [SMILES: CCCOc1ccc(N2CC(Oc3ccc([C@H](C)NC(C)=O)cc3)C2)nc1] | 370 [M + H]⁺ | 1.94 (A) |
| 1.53 | XIII.6 + XXXII | 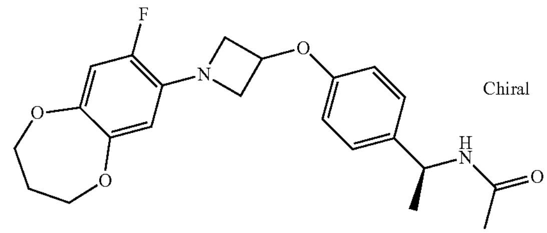 [SMILES: CC(=O)N[C@@H](C)c1ccc(OC2CN(c3cc4c(cc3F)OCCCO4)C2)cc1] | 401 [M + H]⁺ | 1.07 (K) |
| 1.54 | XIII.6 + XVI.20 | 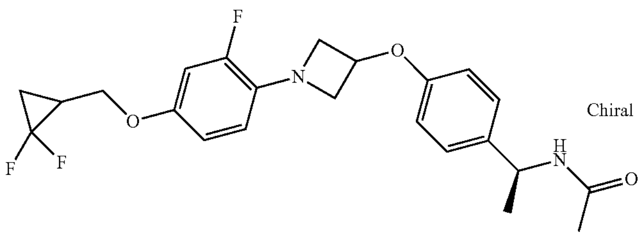 [SMILES: CC(=O)N[C@@H](C)c1ccc(OC2CN(c3ccc(OCC4CC4(F)F)cc3F)C2)cc1] | 435 [M + H]⁺ | 1.29 (N) |
| 1.55 | XIII.6 + XVII.6 | 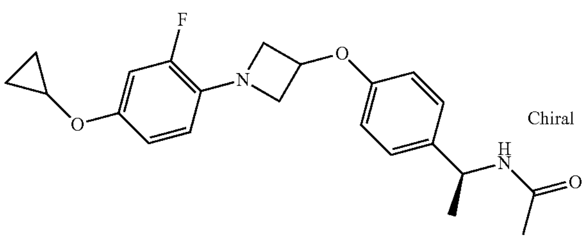 [SMILES: CC(=O)N[C@@H](C)c1ccc(OC2CN(c3ccc(OC4CC4)cc3F)C2)cc1] | 385 [M + H]⁺ | 1.30 (N) |
| 1.56 | XIII.6 | 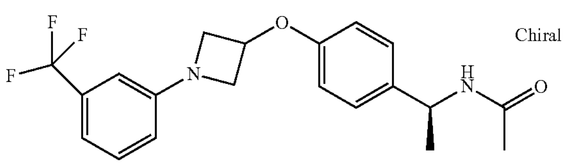 [SMILES: CC(=O)N[C@@H](C)c1ccc(OC2CN(c3cccc(C(F)(F)F)c3)C2)cc1] | 379 [M + H]⁺ | 1.33 (N) |
| 1.57 | XIII.6 + XXXII.2 | 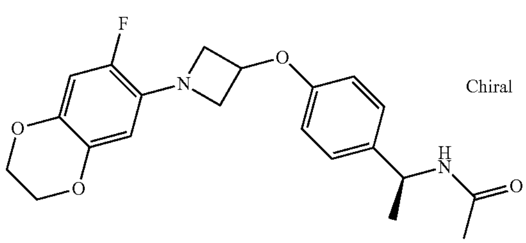 [SMILES: CC(=O)N[C@@H](C)c1ccc(OC2CN(c3cc4c(cc3F)OCCO4)C2)cc1] | 387 [M + H]⁺ | 1.10 (U) |
| 1.58 | XIII.6 + XL.1 | 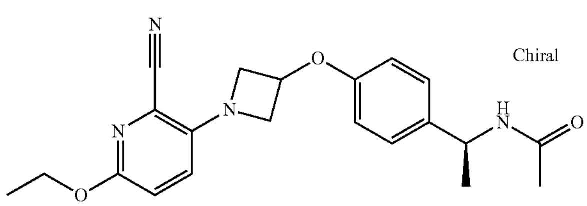 [SMILES: CCOc1ccc(N2CC(Oc3ccc([C@H](C)NC(C)=O)cc3)C2)c(C#N)n1] | 381 [M + H]⁺ | 1.23 (N) |

| Ex. | Starting material(s) | Structure | Mass spec result | HPLC retention time (method) |
|---|---|---|---|---|
| 1.59 | XIII.6 + XL.2 | 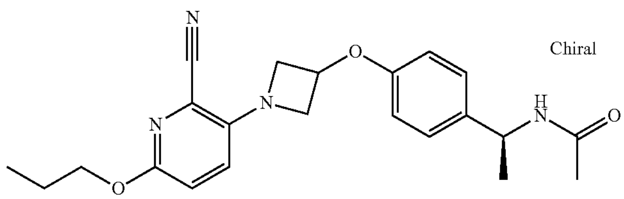 [SMILES: CCCOc1ccc(N2CC(Oc3ccc([C@H](C)NC(C)=O)cc3)C2)c(C#N)n1] | 395 [M + H]⁺ | 1.29 (N) |
| 1.60 | XIII.6 + XL.3 | 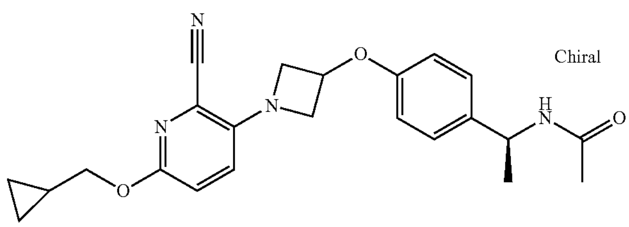 [SMILES: CC(=O)N[C@@H](C)c1ccc(OC2CN(c3ccc(OCC4CC4)nc3C#N)C2)cc1] | 407 [M + H]⁺ | 1.29 (N) |
| 1.61 | XIII.6 + XVI.21 | 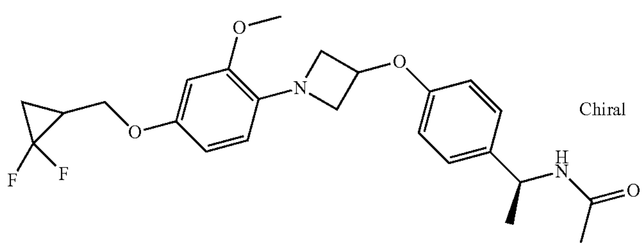 [SMILES: COc1cc(OCC2CC2(F)F)ccc1N1CC(Oc2ccc([C@H](C)NC(C)=O)cc2)C1] | 447 [M + H]⁺ | 1.27 (N) |
| 1.62 | XIII.6 + XLII | 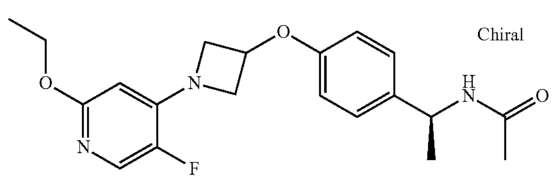 [SMILES: CCOc1cc(N2CC(Oc3ccc([C@H](C)NC(C)=O)cc3)C2)c(F)cn1] | 374 [M + H]⁺ | 1.24 (N) |

Example 2

Example 2.1 (General Route)

(S)—N-(1-(4-(1-(6-(Cyclopropylmethoxy)Pyridin-3-yl)azetidin-3-yloxy)phenyl)ethyl)-acetamide

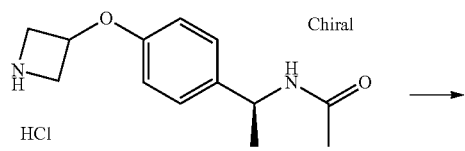

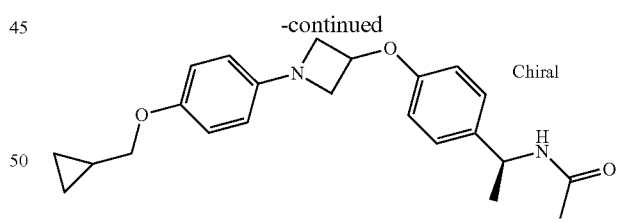

To 80 mg (0.30 mmol) of amine XIII.6 in 0.5 mL toluene and 0.2 mL tert-butanol are added 67.4 mg (0.30 mmol) 5-bromo-2-(cyclopropylmethoxy)pyridine (XXVI1.3), 0.29 g (0.89 mmol) $Cs_2CO_3$, 3.35 mg (0.02 mmol) $PdOAc_2$ and 7.12 mg (0.02 mmol) X-Phos. The mixture is degassed thoroughly and stirred at 120° C. over night. A small amount of water and MeOH are added and the mixture is purified by HPLC (MeOH/$H_2O$/$NH_3$).

$C_{22}H_{27}N_3O_3$ (M=381.5 g/mol)
ESI-MS: 382 [m+H]⁺
$R_f$ (HPLC): 2.05 min (method A)

The following compounds are prepared analogously to example 2.1:

| Ex. | Starting material(s) | Structure | Mass spec result | HPLC retention time (method) |
|---|---|---|---|---|
| 2.1 | XIII.6 + XXVIII.3 | 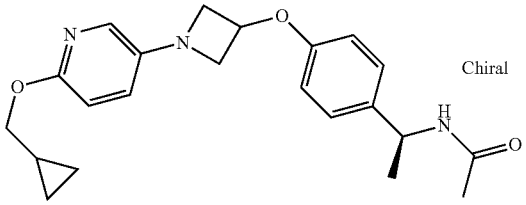 [SMILES: CC(=O)N[C@@H](C)c1ccc(OC2CN(c3ccc(OCC4CC4)nc3)C2)cc1] | 382 [M + H]⁺ | 2.05 (A) |
| 2.2 | XIII.1 + XVI.6 | 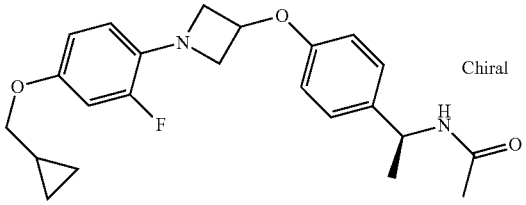 [SMILES: CC(=O)N[C@@H](C)c1ccc(OC2CN(c3ccc(OCC4CC4)cc3F)C2)cc1] | 399 [M + H]⁺ | 2.20 (A) |
| 2.3 | XIII.6 + XVI.7 | 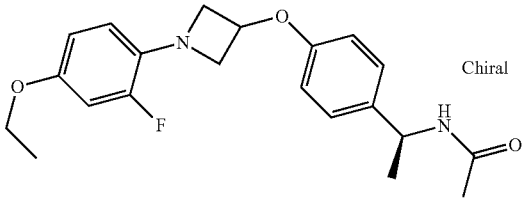 [SMILES: CCOc1ccc(N2CC(Oc3ccc([C@H](C)NC(C)=O)cc3)C2)c(F)c1] | 373 [M + H]⁺ | 2.11 (A) |
| 2.4 | XIII.1 + XVII.5 | 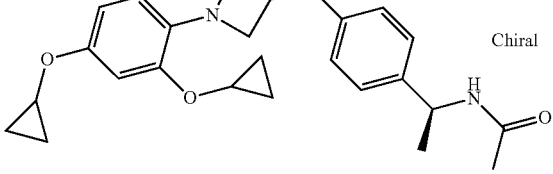 | 423 [M + H]⁺ | 1.33 (N) |
| 2.5 | XIII.1 + XXVIII.5 | 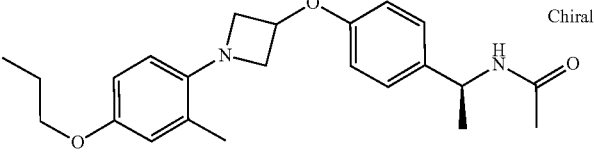 | 383 [M + H]⁺ | 2.22.(A) |
| 2.6 | XIII.1 + XXVIII.4 | 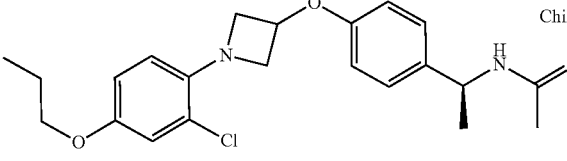 | 403 [M + H]⁺ | 2.29.(A) |
| 2.7 | XIII.1 | 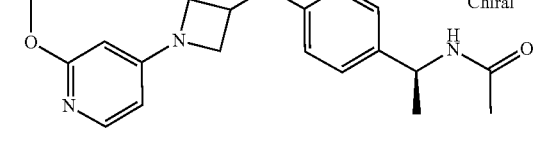 | 370 [M + H]⁺ | 2.02 (A) |
| 2.8 | XIII.1 + XXVIII.2 | 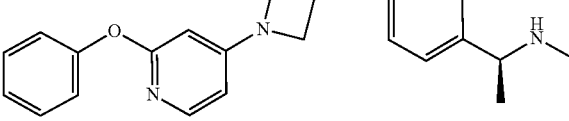 | 404 [M + H]⁺ | 2.04 (A) |

-continued

| Ex. | Starting material(s) | Structure | Mass spec result | HPLC retention time (method) |
|---|---|---|---|---|
| 2.9 | XIII.1 + XXVIII.1 | 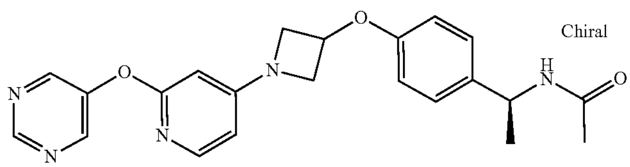 [SMILES: CC(=O)N[C@@H](C)c1ccc(OC2CN(c3ccnc(Oc4cncnc4)c3)C2)cc1] | 406 [M + H]⁺ | 1.79 (A) |
| 2.10 | XIII.3 | 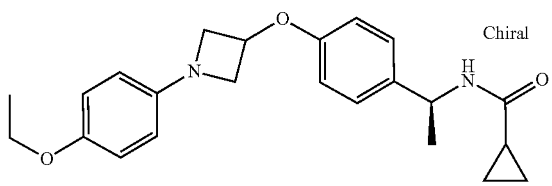 [SMILES: CCOc1ccc(N2CC(Oc3ccc([C@H](C)NC(=O)C4CC4)cc3)C2)cc1] | 381 [M + H]⁺ | 2.11 (A) |
| 2.11 | XIII.6 + XVI.17 | 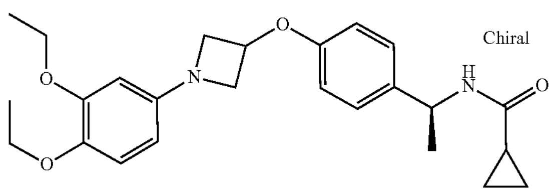 | 399 [M + H]⁺ | 1.28 (L) |
| 2.12 | XIII.6 + XXX | 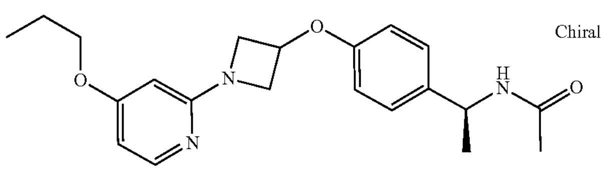 [SMILES: CCCOc1ccnc(N2CC(Oc3ccc([C@H](C)NC(C)=O)cc3)C2)c1] | 370 [M + H]⁺ | 1.07 (A) |

Example 3

Example 3.1 (General Route)

(S)—N-(1-(4-(1-(5-bromopyrimidin-2-yl)azetidin-3-yloxy)phenyl)ethyl)acetamide

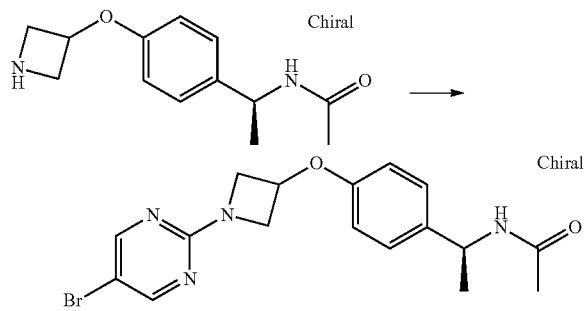

0.69 g (3.59 mmol) 5-bromo-2-chloro-pyrimidine and 0.70 g (2.99 mmol) of the amine XIII.1 are added to 10 mL DMSO and 0.78 mL (4.49 mmol) DIPEA. The mixture is stirred at 35° C. over night and afterwards purified by HPLC (MeOH/H₂O/NH₃).

$C_{17}H_{19}BrN_4O_2$ (M=391.3 g/mol)

ESI-MS: 391/393 [m+H]⁺

R$_t$ (HPLC): 1.80 min (method A)

The following compounds are prepared analogously to example 3.1:

For the example 3.2 the reaction mixture is stirred for 4 d at 45° C.

For the examples 3.3-3.4 and 3.8 the reaction mixture is stirred for 3 d at 35° C.

For the example 3.6 the reaction mixture is stirred at 50° C. over night. Then some water and MeOH is added and the resulting precipitate is filtered, washed with water and dried in vacuo.

For the example 3.7 the reaction is done in ACN instead of DMSO and the reaction mixture is stirred at 70° C. for 3 h.

For the examples 3.9-3.11 the reaction is done in ACN instead of DMSO and the reaction mixture is stirred at 60° C. over night.

| Ex. | Starting material(s) | Structure | Mass spec result | HPLC retention time (method) |
|---|---|---|---|---|
| 3.1 | XIII.1 | (Chiral structure: 5-bromopyrimidine-azetidine-O-phenyl-CH(CH₃)-NHAc) | 390/392 [M + H]⁺ | 1.80 (A) |
| 3.2 | XIII.1 | (Chiral structure: 5-methoxypyrimidine-azetidine-O-phenyl-CH(CH₃)-NHAc) | 343 [M + H]⁺ | 1.63 (A) |
| 3.3 | XIII.2 | (5-propylpyrimidine-azetidine-O-phenyl-CH(CH₃)-NHAc) | 355 [M + H]⁺ | 1.89 (A) |
| 3.4 | XIII.2 | (5-(4-methoxyphenyl)pyrimidine-azetidine-O-phenyl-CH(CH₃)-NHAc) | 419 [M + H]⁺ | 1.97 (A) |
| 3.5 | XIII.3 + XXI.1 | (Chiral: 5-cyclopropylpyrimidine-azetidine-O-phenyl-CH(CH₃)-NHC(O)cyclopropyl) | 379 [M + H]⁺ | 2.15 (A) |
| 3.6 | XIII.3 | (Chiral: 5-bromopyrimidine-azetidine-O-phenyl-CH(CH₃)-NHC(O)cyclopropyl) | 416/418 [M + H]⁺ | 2.05 (A) |
| 3.7 | XIII.3 | (Chiral: 5-bromopyrimidine-azetidine-O-phenyl-CH(CH₃)-NHC(O)N(CH₃)₂) | 419/421 [M + H]⁺ | 2.01 (A) |
| 3.8 | XIII.3 | (Chiral: 4-trifluoromethylpyrimidine-azetidine-O-phenyl-CH(CH₃)-NHC(O)N(CH₃)₂) | 409 [M + H]⁺ | 1.12 (K) |

-continued

| Ex. | Starting material(s) | Structure | Mass spec result | HPLC retention time (method) |
|---|---|---|---|---|
| 3.9 | XIII.6 | 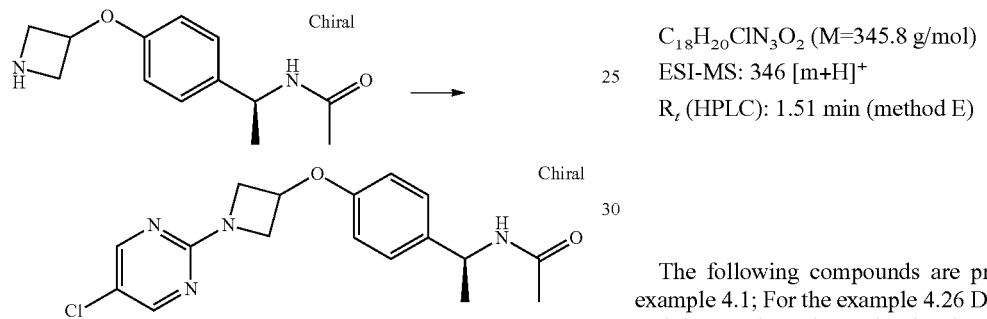 | 395 [M + H]⁺ | 2.00 (A) |

Example 4

Example 4.1 (General Route)

(S)—N-(1-(4-(1-(5-Chloropyridin-2-yl)azetidin-3-yloxy)phenyl)ethyl)acetamide

To 14.8 mg (0.10 mmol) 2,5-dichloro-pyridine is added 23.4 mg (0.1 mmol) of the amine XIII.1 in 1.45 mL NMP and 0.05 mL (0.30 mmol) DIPEA. The mixture is stirred at 130° C. over night. Afterwards the solvent is removed in vacuo and the residue is purified by HPLC (MeOH/H$_2$O/TFA).

C$_{18}$H$_{20}$ClN$_3$O$_2$ (M=345.8 g/mol)
ESI-MS: 346 [m+H]⁺
R$_t$ (HPLC): 1.51 min (method E)

The following compounds are prepared analogously to example 4.1; For the example 4.26 DMSO is used as solvent and the reaction mixture is stirred at 150° C. over night.

| Ex. | Starting material(s) | Structure | Mass spec result | HPLC retention time (method) |
|---|---|---|---|---|
| 4.1 | XIII.1 | 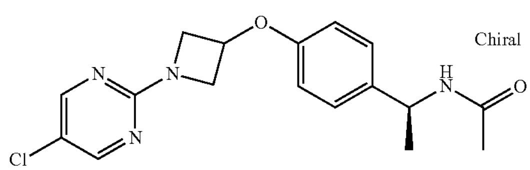 [SMILES: CC(=O)N[C@@H](C)c1ccc(OC2CN(c3ncc(Cl)cn3)C2)cc1] | 346 [M + H]⁺ | 1.51 (E) |
| 4.2 | XIII.1 | 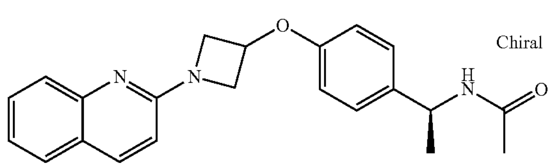 [SMILES: CC(=O)N[C@@H](C)c1ccc(OC2CN(c3ccc4ccccc4n3)C2)cc1] | 362 [M + H]⁺ | 1.18 (E) |
| 4.3 | XIII.1 | 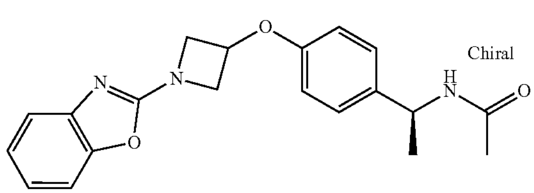 [SMILES: CC(=O)N[C@@H](C)c1ccc(OC2CN(c3nc4ccccc4o3)C2)cc1] | 352 [M + H]⁺ | 1.78 (E) |

-continued
| Ex. | Starting material(s) | Structure | Mass spec result | HPLC retention time (method) |
|---|---|---|---|---|
| 4.4 | XIII.1 | 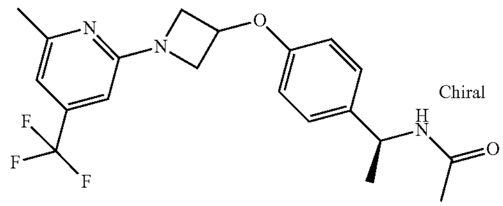 [SMILES: CC(=O)N[C@@H](C)c1ccc(OC2CN(c3cc(C(F)(F)F)cc(C)n3)C2)cc1] | 394 [M + H]⁺ | 1.67 (E) |
| 4.5 | XIII.1 + * | 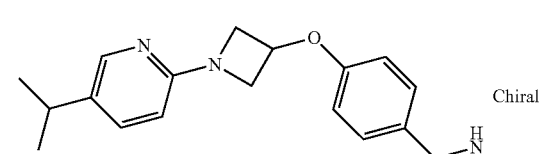 | 354 [M + H]⁺ | 1.16 (E) |
| 4.6 | XIII.1 | 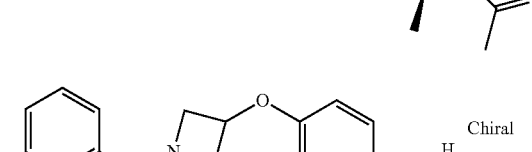 | 362 [M + H]⁺ | 1.19 (E) |
| 4.7 | XIII.1 | 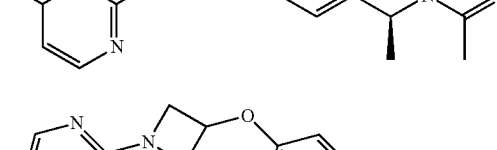 | 346 [M + H]⁺ | 1.12 (E) |
| 4.8 | XIII.1 | 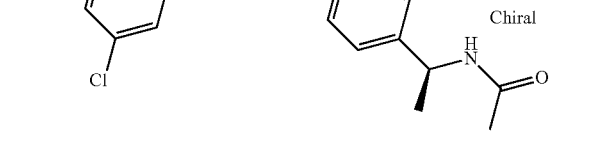 | 388 [M + H]⁺ | 1.33 (E) |
| 4.9 | XIII.1 | 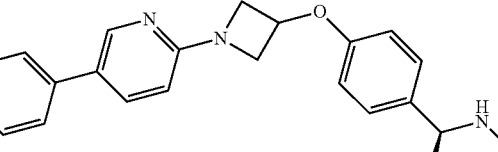 | 403 [M + Na]⁺ | 1.73 (E) |
| 4.10 | XIII.1 | 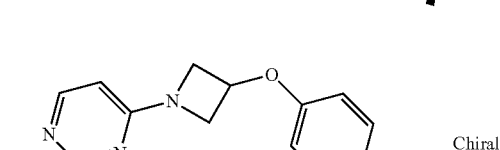 | 398 [M + H]⁺ | 2.01 (E) |

-continued

| Ex. | Starting material(s) | Structure | Mass spec result | HPLC retention time (method) |
|---|---|---|---|---|
| 4.11 | XIII.1 | Chiral | 356 [M + H]+ | 1.93 (E) |
| 4.12 | XIII.1 | Chiral | 377 [M + H]+ | 1.10 (E) |
| 4.13 | XIII.1 | Chiral | 368 [M + H]+ | 1.68 (E) |
| 4.14 | XIII.1 | Chiral | 381 [M + H]+ | 1.69 (E) |
| 4.15 | XIII.1 | Chiral | 396 [M + H]+ | 1.30 (E) |
| 4.16 | XIII.1 | Chiral | 381 [M + H]+ | 1.87 (E) |
| 4.17 | XIII.1 | Chiral | 389/391 [M + H]+ | 1.56 (E) |

-continued

| Ex. | Starting material(s) | Structure | Mass spec result | HPLC retention time (method) |
|---|---|---|---|---|
| 4.18 | XIII.1 | Chiral | 389/391 [M + H]⁺ | 1.12 (E) |
| 4.19 | XIII.1 | Chiral | 380 [M + H]⁺ | 1.76 (E) |
| 4.20 | XIII.1 | Chiral | 380 [M + H]⁺ | 1.72 (E) |
| 4.21 | XIII.1 | Chiral | 380 [M + H]⁺ | 1.90 (E) |
| 4.22 | XIII.1 | Chiral | 392 [M + H]⁺ | 1.25 (E) |
| 4.23 | XIII.1 + XXV.1 | Chiral | 430 [M + H]⁺ | 2.03 (E) |
| 4.24 | XIII.1 | Chiral | 347 [M + H]⁺ | 1.81 (E) |

-continued

| Ex. | Starting material(s) | Structure | Mass spec result | HPLC retention time (method) |
|---|---|---|---|---|
| 4.25 | XIII.1 | Chiral | 352 [M + H]+ | 1.84 (E) |
| 4.26 | XIII.6 + XXV.2 | Chiral | 436 [M + H]+ | 1.26 (N) |
| 4.27 | XIII.6 + XLIII | Chiral | 369 [M + H]+ | 0.48 (T) |
| 4.28 | XIII.6 | Chiral | 363 [M + H]+ | 0.47 (T) |
| 4.29 | XIII.6 | Chiral | 380 [M + H]+ | 0.45 (T) |
| 4.30 | XIII.6 | Chiral | 384 [M + H]+ | 0.48 (T) |

-continued

| Ex. | Starting material(s) | Structure | Mass spec result | HPLC retention time (method) |
|---|---|---|---|---|
| 4.31 | XIII.6 | Chiral | 398 [M + H]⁺ | 0.51 (T) |
| 4.32 | XIII.6 | Chiral | 414 [M + H]⁺ | 0.53 (T) |
| 4.33 | XIII.6 | Chiral | 453 [M + H]⁺ | 0.53 (T) |
| 4.34 | XIII.6 + XLI.2 | Chiral | 371 [M + H]⁺ | 0.47 (T) |
| 4.35 | XIII.6 | Chiral | 415 [M + H]⁺ | 0.50 (T) |
| 4.36 | XIII.6 | Chiral | 477 [M + H]⁺ | 0.56 (T) |

| Ex. | Starting material(s) | Structure | Mass spec result | HPLC retention time (method) |
|---|---|---|---|---|
| 4.37 | XIII.6 | Chiral | 398 [M + H]+ | 0.51 (T) |
| 4.38 | XIII.6 | Chiral | 377 [M + H]+ | 0.47 (T) |
| 4.39 | XIII.6 | Chiral | 408 | 0.53 (T) |
| 4.39 | XIII.6 | Chiral | 355 [M + H]+ | 0.49 (T) |
| 4.40 | XIII.6 | Chiral | 380 [M + H]+ | 0.51 (T) |
| 4.41 | XIII.6 | Chiral | 379 [M + H]+ | 0.51 (T) |
| 4.42 | XIII.6 + XLI | Chiral | 419 [M + H]+ | 1.42 (V) |

-continued

| Ex. | Starting material(s) | Structure | Mass spec result | HPLC retention time (method) |
|---|---|---|---|---|
| 4.43 | XIII.6 | 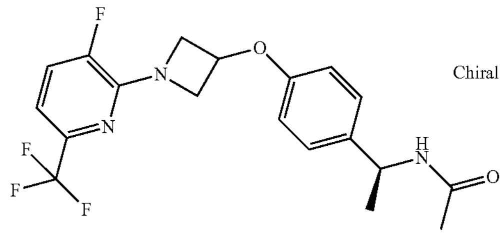 [SMILES: CC(=O)N[C@@H](C)c1ccc(OC2CN(c3nc(C(F)(F)F)ccc3F)C2)cc1] | 398 [M + H]⁺ | 1.14 (K) |

*The appropriate 2-chloropyridyl can be prepared according to J. Med.Chem 1980, 23, 92-95.

Example 5

Example 5.1 (General Route)

(S)—N-(1-(4-(1-(5-Cyclopropylpyrimidin-2-yl)azetidin-3-yloxy)phenyl)ethyl)acetamide

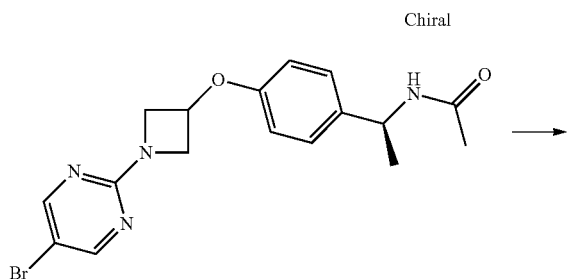

To 0.1 g (0.26 mmol) of the arylbromide 3.1, 65.9 mg (0.77 mmol) cyclopropyl boronic acid, 0.19 g (0.90 mmol) K₃PO₄, 11.5 mg (0.05 mmol) PdOAc₂ and 7.17 mg (0.03 mmol) tricyclohexylphosphine are added 3 mL toluene and 150 µl water. The resulting mixture is degassed and stirred at 100° C. over night. Then the reaction mixture is filtered and the sovent is removed in vacuo. The residue is purified by HPLC (acetone/H₂O/NH₃).

$C_{20}H_{24}N_4O_2$ (M=352.4 g/mol)
ESI-MS: 353 [M+H]⁺
R$_t$ (HPLC): 1.81 min (method A)

The following compounds are prepared analogously to example 5.1:

For the example 5.2 3 eq of trimethylboroxine are used for the cross coupling.

| Ex. | Starting material | Structure | Mass spec result | HPLC retention time (method) |
|---|---|---|---|---|
| 5.1 | 3.1 | Chiral | 353 [M + H]⁺ | 1.81 (A) |

-continued

For the example 5.2 3 eq of trimethylboroxine are used for the cross coupling.

| Ex. | Starting material | Structure | | Mass spec result | HPLC retention time (method) |
|---|---|---|---|---|---|
| 5.2 | 3.1 | 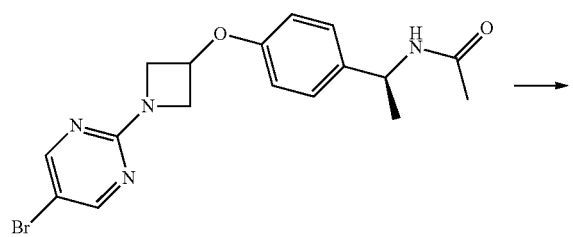 | Chiral | 327 [M + H]⁺ | 1.64 (A) |

Example 6

Example 6.1 (General Route)

(S)—N-(1-(4-(1-(5-Cyclopropylpyrimidin-2-yl)azetidin-3-yloxy)phenyl)ethyl)acetamide

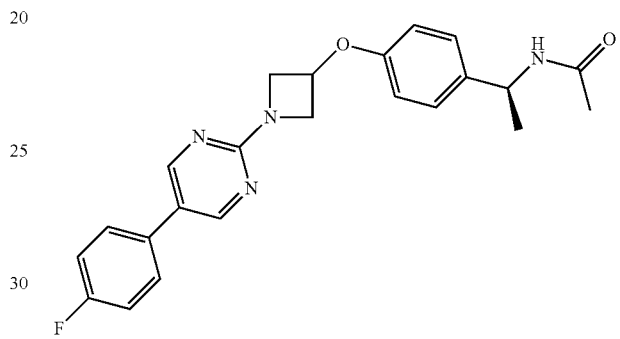

To 50.0 g (0.13 mmol) of the arylbromide 3.1 and 19.7 mg (0.14 mmol) 4-fluorophenyl boronic acid in 1.5 mL dioxane and 1.5 mL methanol are added 0.13 mL (0.26 mmol) of an aq. $Na_2CO_3$ solution (c=2 mol/l) and 3.58 mg (0.005 mmol) $Pd(PPh_3)_2Cl_2$. The resulting mixture is stirred at 95° C. for 3 h. Then water and EtOAc are added and the layers are separated. The org. layer is filtered and the sovent is removed in vacuo. The residue is purified by HPLC (acetone/$H_2O$/$NH_3$).
$C_{23}H_{23}FN_4O_2$ (M=406.5.4 g/mol)
ESI-MS: 407 [M+H]⁺
$R_t$ (HPLC): 1.99 min (method A)

The following compounds are prepared analogously to example 6.1:

| Ex. | Starting material | Structure | | Mass spec result | HPLC retention time (method) |
|---|---|---|---|---|---|
| 6.1 | 3.1 | 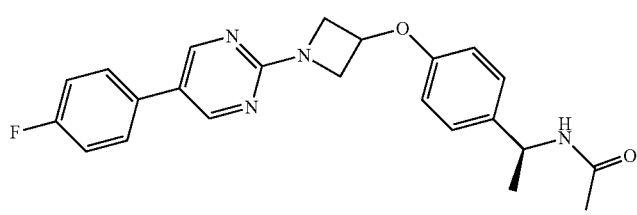 | Chiral | 407 [M + H]⁺ | 1.99 (A) |

-continued

The following compounds are prepared analogously to example 6.1:

| Ex. | Starting material | Structure | | Mass spec result | HPLC retention time (method) |
|---|---|---|---|---|---|
| 6.2 | 3.1 | 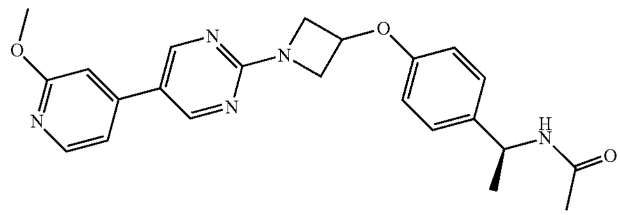 | Chiral | 420 [M + H]+ | 1.87 (A) |
| 6.3 | 1.8 | 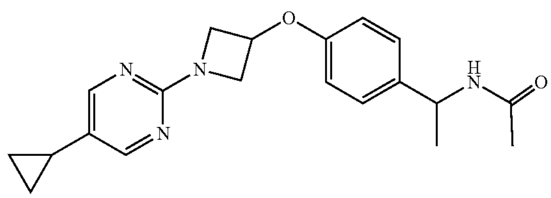 | Chiral | 353 [M + H]+ | 1.81 (A) |

Example 7

Example 7.1 (General Route)

(S)—N-(1-(4-(1-(3-(Cyclopropylmethoxy)phenyhazetidin-3-yloxy)phenylethyl)-acetamide

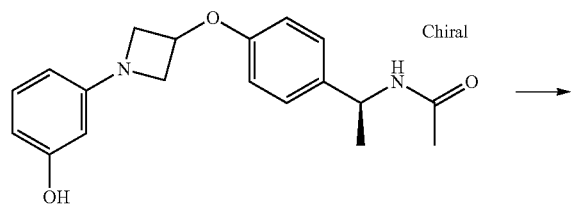

→

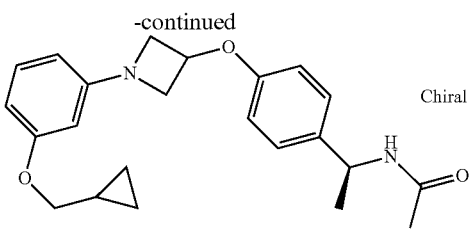

To 50.0 mg (0.15 mmol) of the phenol XXXIII and 22.0 µl (0.23 mmol) (bromomethyl)-cyclopropane in 1 mL DMF are added 52.9 mg (0.38 mmol) $K_2CO_3$. The resulting mixture is stirred at 80° C. for 4 h. Then a small amount of water and methanol are added and the mixture is directly purified by HPLC (ACN/H$_2$O/FA).

$C_{23}H_{28}N_2O_3$ (M=380.5 g/mol)
ESI-MS: 381 [M+H]+
R$_t$ (HPLC): 1.18 min (method K)

The following compounds are prepared analogously to example 7.1:

| Ex. | Starting material | Structure | | Mass spec result | HPLC retention time (method) |
|---|---|---|---|---|---|
| 7.1 | XXXIII | 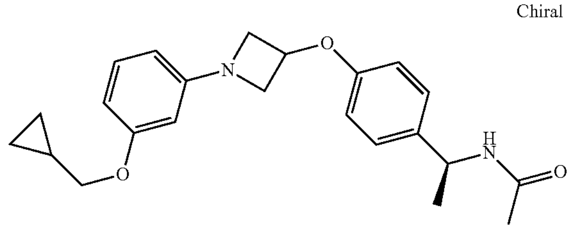 [SMILES: CC(=O)N[C@@H](C)c1ccc(OC2CN(c3cccc(OCC4CC4)c3)C2)cc1] | Chiral | 381 [M + H]+ | 1.18 (K) |

-continued

The following compounds are prepared analogously to example 7.1:

| Ex. | Starting material | Structure | Mass spec result | HPLC retention time (method) |
|---|---|---|---|---|
| 7.2 | XXXIII | Chiral | 417 [M + H]⁺ | 1.14 (K) |
| 7.3 | XXXIII | Chiral | 395 [M + H]⁺ | 1.26 (K) |

Example 8

Example 8.1 (General Route)

(S)—N-(1-(4-(1-(2-Methoxy-4-propoxyphenyl)azetidin-3-yloxy)phenyl)ethyl)cyclopropanecarboxamide

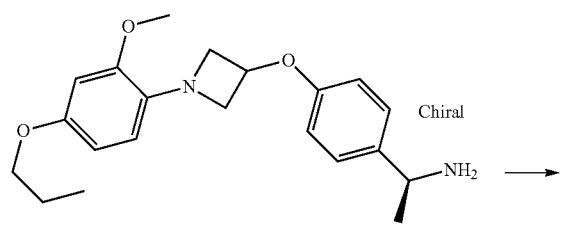

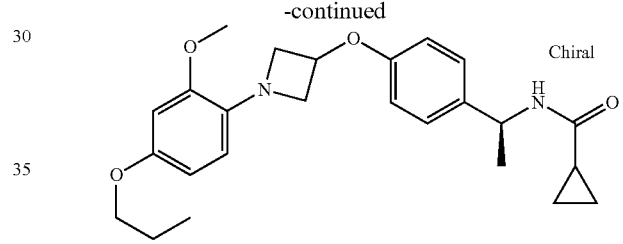

15.5 mg (0.18 mmol) cyclopropanecarboxylic acid, 46.9 µl (0.18 mmol) DIPEA and 75.1 mg (0.27 mmol) HATU are added to 5 mL THF and stirred for 5 min. Then 80.0 mg (0.18 mmol) of the amine XXXVIII in 2 mL THF are added and the resulting mixture is stirred at r.t. for 5 h. Afterwards the mixture is directly purified by HPLC (acetone/H₂O/NH₃).

$C_{25}H_{32}N_2O_4$ (M=424.5 g/mol)
ESI-MS: 425 [M+H]⁺
$R_f$ (HPLC): 2.23 min (method A)

The following compounds are prepared analogously to example 8.1:

For the examples 8.6-8.48 TBTU and DMF are used instead of HATU and THF.

| Ex. | Starting material | Structure | Mass spec result | HPLC retention time (method) |
|---|---|---|---|---|
| 8.1 | XXXVIII | Chiral | 425 [M + H]⁺ | 2.23 (A) |

-continued

| Ex. | Starting material | Structure | Mass spec result | HPLC retention time (method) |
|---|---|---|---|---|
| 8.2 | XXXVIII | Chiral | 417 [M + H]+ | 2.20 (A) |
| 8.3 | XXXVIII | Chiral | 451 [M + H]+ | 2.16 (A) |
| 8.4 | XXXVIII | Chiral | 468 [M + H]+ | 2.22 (A) |
| 8.5 | XXXIV | Chiral | 405 [M + H]+ | 1.94 (A) |
| 8.6 | XXXIV | Chiral | 378 [M + H]+ | 1.92 (A) |
| 8.7 | XXXVI | Chiral | 407 [M + H]+ | 1.05 (M) |

-continued

| Ex. | Starting material | Structure | Mass spec result | HPLC retention time (method) |
|---|---|---|---|---|
| 8.8 | XXXVI | Chiral | 380 [M + H]+ | 1.04 (M) |
| 8.9 | XXXVI | Chiral | 395 [M + H]+ | 0.63 (T) |
| 8.10 | XXXVI | Chiral | 497 [M + H]+ | 0.61 (T) |
| 8.11 | XXXVI | Chiral | 474 [M + H]+ | 0.62 (T) |
| 8.12 | XXXVI | Chiral | 406 [M + H]+ | 0.62 (T) |
| 8.13 | XXXVI | Chiral | 381 [M + H]+ | 0.62 (T) |
| 8.14 | XXXVI | Chiral | 419 [M + H]+ | 0.61 (T) |

-continued

| Ex. | Starting material | Structure | | Mass spec result | HPLC retention time (method) |
|---|---|---|---|---|---|
| 8.15 | XXXVI | 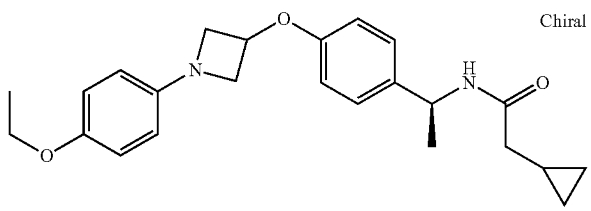 [SMILES: CCOc1ccc(N2CC(Oc3ccc([C@H](C)NC(=O)CC4CC4)cc3)C2)cc1] | Chiral | 395 [M + H]⁺ | 0.62 (T) |
| 8.16 | XXXVI | 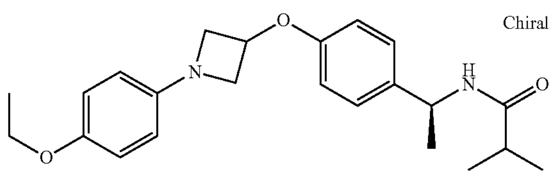 [SMILES: CCOc1ccc(N2CC(Oc3ccc([C@H](C)NC(=O)C(C)C)cc3)C2)cc1] | Chiral | 383 [M + H]⁺ | 0.62 (T) |
| 8.17 | XXXVI | 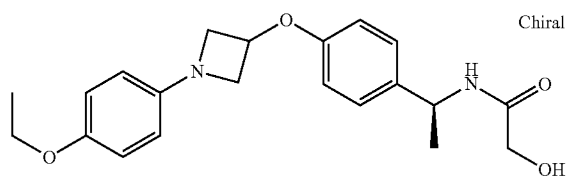 [SMILES: CCOc1ccc(N2CC(Oc3ccc([C@H](C)NC(=O)CO)cc3)C2)cc1] | Chiral | 371 [M + H]⁺ | 0.61 (T) |
| 8.18 | XXXVI | 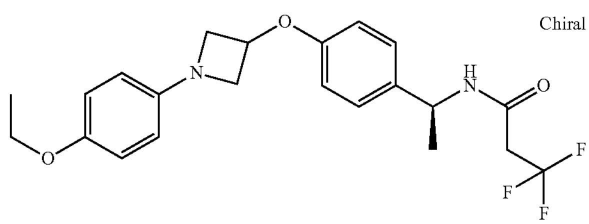 [SMILES: CCOc1ccc(N2CC(Oc3ccc([C@H](C)NC(=O)CC(F)(F)F)cc3)C2)cc1] | Chiral | 423 [M + H]⁺ | 0.62 (T) |
| 8.19 | XXXVI | 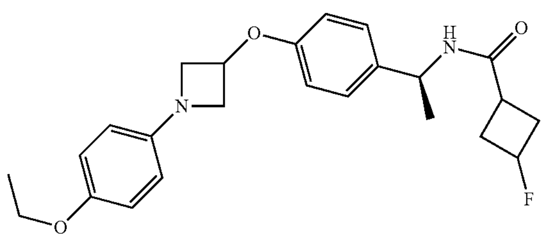 | Chiral | 413 [M + H]⁺ | 0.62 (T) |
| 8.20 | XXXVI | 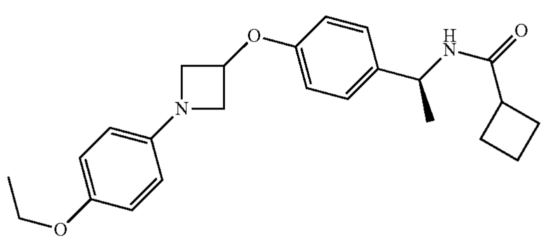 | Chiral | 395 [M + H]⁺ | 0.62 (T) |

-continued

| Ex. | Starting material | Structure | Mass spec result | HPLC retention time (method) |
|---|---|---|---|---|
| 8.21 | XXXVI | (Chiral structure: 1-(4-ethoxyphenyl)azetidin-3-yloxy-phenyl ethyl amide of 1-(trifluoromethyl)cyclopropanecarboxylic acid) | 449 [M + H]⁺ | 0.64 (T) |
| 8.22 | XXXVI | (Chiral structure with 2,5-dimethylthiazole-4-carboxamide) | 452 [M + H]⁺ | 0.62 (T) |
| 8.23 | XXXVI | (Chiral structure with N,N-dimethylglycinamide) | 398 [M + H]⁺ | 0.61 (T) |
| 8.24 | XXXVI | (Chiral structure with 2-(pyridin-3-yl)acetamide) | 432 [M + H]⁺ | 0.60 (T) |
| 8.25 | XXXVI | (Chiral structure with 2-acetamidopyridine-4-carboxamide) | 475 [M + H]⁺ | 0.61 (T) |
| 8.26 | XXXVI | (Chiral structure with 3-methoxypropanamide) | 399 [M + H]⁺ | 0.61 (T) |

| Ex. | Starting material | Structure | Mass spec result | HPLC retention time (method) |
|---|---|---|---|---|
| 8.27 | XXXVI | (Chiral structure) | 409 [M + H]⁺ | 0.63 (T) |
| 8.28 | XXXVI | (Chiral structure) | 495 [M + H]⁺ | 0.62 (T) |
| 8.29 | XXXVI | (Chiral structure) | 369 [M + H]⁺ | 0.61 (T) |
| 8.30 | XXXVI | (Chiral structure) | 373 [M + H]⁺ | 0.61 (T) |
| 8.31 | XXXVI | (Chiral structure) | 408 [M + H]⁺ | 0.62 (T) |
| 8.32 | XXXVI | (Chiral structure) | 481 [M + H]⁺ | 0.62 (T) |

| Ex. | Starting material | Structure | Mass spec result | HPLC retention time (method) |
|---|---|---|---|---|
| 8.33 | XXXVI | Chiral | 408 [M + H]+ | 0.61 (T) |
| 8.34 | XXXVI | Chiral | 424 [M + H]+ | 0.62 (T) |
| 8.35 | XXXVI | 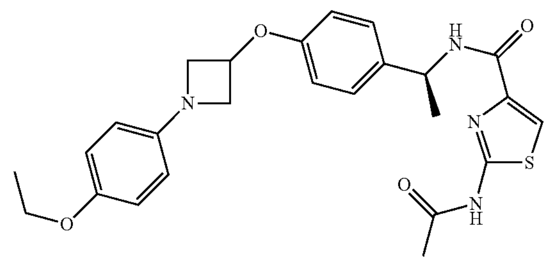 [SMILES: CCOc1ccc(N2CC(Oc3ccc([C@H](C)NC(=O)c4csc(NC(C)=O)n4)cc3)C2)cc1] | 481 [M + H]+ | 0.62 (T) |
| 8.36 | XXXVI | 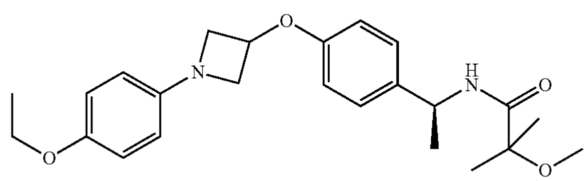 [SMILES: CCOc1ccc(N2CC(Oc3ccc([C@H](C)NC(=O)C(C)(C)OC)cc3)C2)cc1] | 413 [M + H]+ | 0.63 (T) |
| 8.37 | XXXVI | 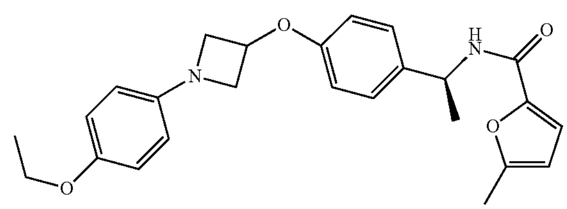 [SMILES: CCOc1ccc(N2CC(Oc3ccc([C@H](C)NC(=O)c4ccc(C)o4)cc3)C2)cc1] | 421 [M + H]+ | 0.63 (T) |
| 8.38 | XXXVI | 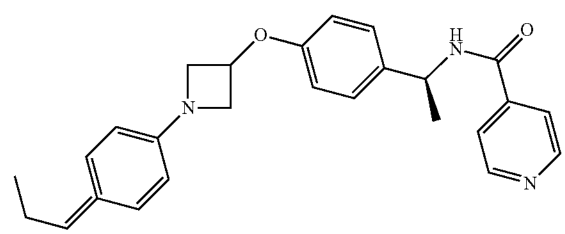 | 418 [M + H]+ | 0.60 (T) |

| Ex. | Starting material | Structure | Mass spec result | HPLC retention time (method) |
|---|---|---|---|---|
| 8.39 | XXXVI | 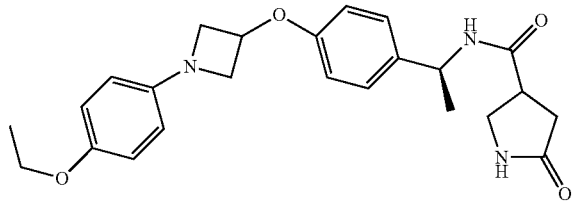 [SMILES: CCOc1ccc(N2CC(Oc3ccc([C@H](C)NC(=O)C4CNC(=O)C4)cc3)C2)cc1] | 424 [M + H]+ | 0.61 (T) |
| 8.40 | XXXVI | 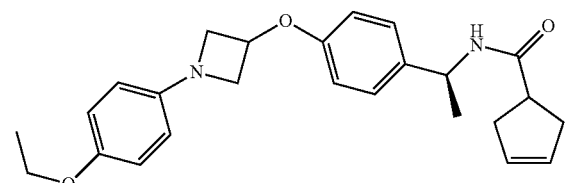 | 407 [M + H]+ | 0.63 (T) |
| 8.14 | XXXVI | 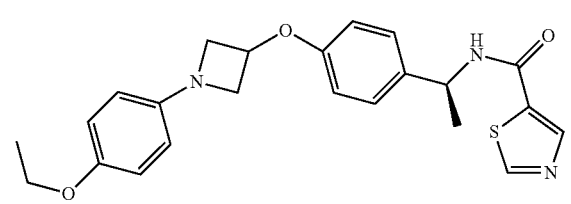 [SMILES: CCOc1ccc(N2CC(Oc3ccc([C@H](C)NC(=O)c4cncs4)cc3)C2)cc1] | 424 [M + H]+ | 0.62 (T) |
| 8.42 | XXXVI | 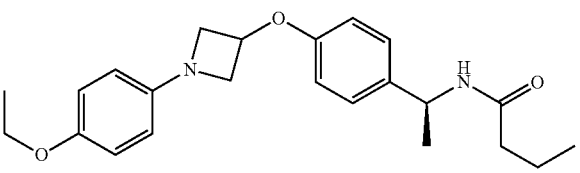 [SMILES: CCCC(=O)N[C@@H](C)c1ccc(OC2CN(c3ccc(OCC)cc3)C2)cc1] | 383 [M + H]+ | 0.62 (T) |
| 8.43 | XXXVI | 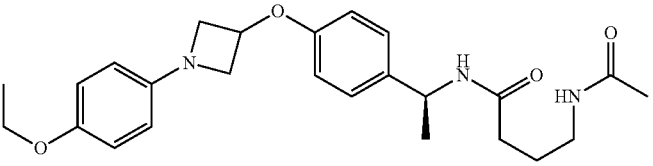 [SMILES: CCOc1ccc(N2CC(Oc3ccc([C@H](C)NC(=O)CCCNC(C)=O)cc3)C2)cc1] | 440 [M + H]+ | 0.61 (T) |
| 8.44 | XXXVI | 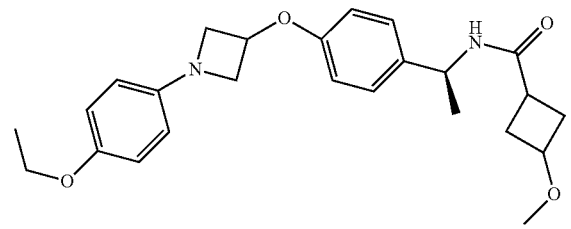 [SMILES: CCOc1ccc(N2CC(Oc3ccc([C@H](C)NC(=O)C4CC(OC)C4)cc3)C2)cc1] | 425 [M + H]+ | 0.62 (T) |
| 8.45 | XXXVI | 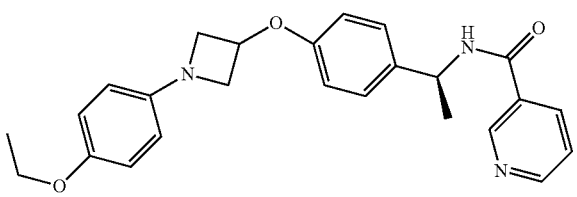 [SMILES: CCOc1ccc(N2CC(Oc3ccc([C@H](C)NC(=O)c4cccnc4)cc3)C2)cc1] | 418 [M + H]+ | 0.60 (T) |

-continued

| Ex. | Starting material | Structure | Mass spec result | HPLC retention time (method) |
|---|---|---|---|---|
| 8.46 | XXXVI | 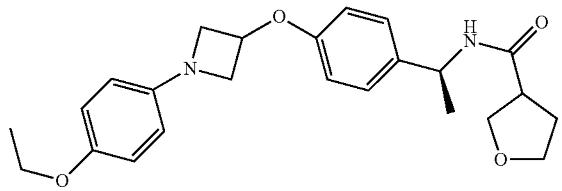 [SMILES: CCOc1ccc(N2CC(Oc3ccc([C@H](C)NC(=O)C4CCOC4)cc3)C2)cc1] | 411 [M + H]⁺ | 0.61 (T) |
| 8.47 | XXXVI | 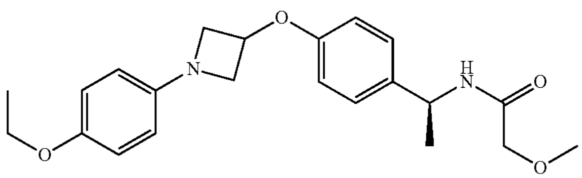 [SMILES: CCOc1ccc(N2CC(Oc3ccc([C@H](C)NC(=O)COC)cc3)C2)cc1] | 385 [M + H]⁺ | 0.61 (T) |

Example 9

(S)—N-(1-(4-(1-(5-Cyclopropylpyrimidin-2-yl)azetidin-3-yloxy)phenyl)ethyl)-propionamide

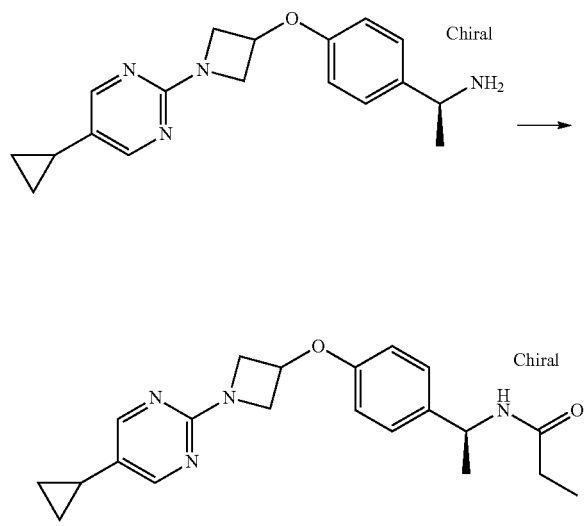

60.0 mg (0.19 mmol) of the amine XXXIV are added to 1 mL DCM and charged with 0.11 mL (0.77 mmol) TEA and 0.02 mL (0.23 mmol) propionyl chloride. The resulting mixture is stirred at r.t. for 3 h. Afterwards a small amount of MeOH is added and the mixture is directly purified by HPLC (MeOH/H₂O/NH₃).

$C_{21}H_{26}N_4O_2$ (M=366.5 g/mol)

ESI-MS: 367 [M+H]⁺

R$_t$ (HPLC): 2.00 min (method A)

Example 10

Example 10.1 (General Route)

(S)—N-(1-(4-(1-(2-Methoxy-4-propoxyphenyl)azetidin-3-yloxy)phenyl)ethyl)cyclopropanecarboxamide 65 mg (0.21 mmol) amine XXXIV and 0.06 mL (0.42 mmol) TEA are added to 1 mL DCM and charged with 36.1 mg (0.22 mmol) CDT. The reaction mixture is stirred at r.t. for 15 min. Then 28.3 mg (0.63 mmol) dimethylamine are added and stirring is continued for 3 h. Some MeOH is added and the mixture is directly purified by HPLC (MeOH/H₂O/NH₃).

$C_{21}H_{27}N_6O_2$ (M=381.5 g/mol)

ESI-MS: 382 [m+H]⁺

R$_t$ (HPLC): 2.01 min (method A)

The following compounds are prepared analogously to example 10.1:

For the example 10.5 the CDT is added at 0° C. and stirring is continued at 0-5° C. for 15 min before the mixture is warmed to r.t., stirred for additional 5 min and then charged with the dimethylamine.

For the examples 10.6-10.7 a mixture of 1.8 eq NaOMe in 1 mL MeOH is added after the CDT activation.

| Ex. | Starting material | Structure | | Mass spec result | HPLC retention time (method) |
|---|---|---|---|---|---|
| 10.1 | XXXIV | 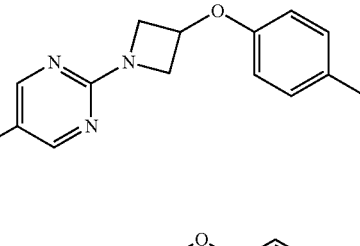 | | 382 [M + H]⁺ | 2.01 (A) |
| 10.2 | XXXIV | 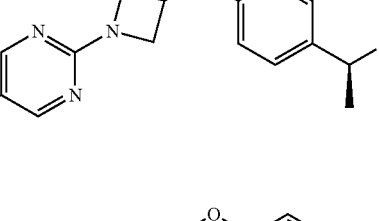 | | 382 [M + H]⁺ | 2.00 (A) |
| 10.3 | XXXVI | 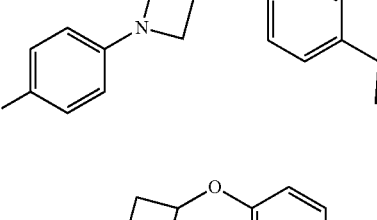 | Chiral | 384 [M + H]⁺ | 2.11 (A) |
| 10.4 | XXXVI | 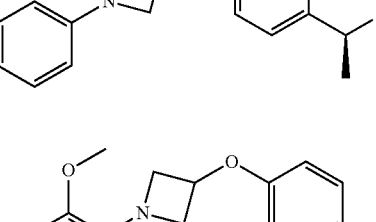 | Chiral | 384 [M + H]⁺ | 2.11 (A) |
| 10.5 | XXXVI | 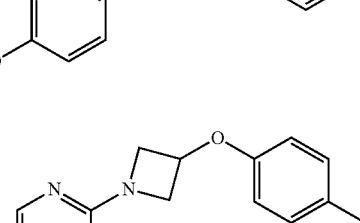 | Chiral | 428 [M + H]⁺ | 2.20 (A) |
| 10.6 | XXXIV | 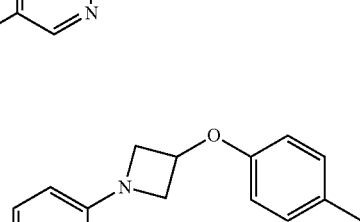 | Chiral | 369 [M + H]⁺ | 2.05 (A) |
| 10.7 | XXXVI | 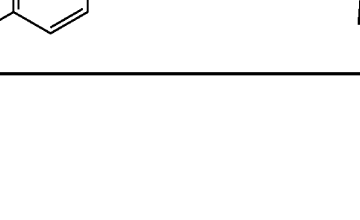 | Chiral | 371 [M + H]⁺ | 1.14 (M) |

Example 11

Example 11.1 (General Route)

(S)—N-(1-(4-(1-(6-Propoxypyrimidin-4-yl)azetidin-3-yloxy)phenyl)ethyl)acetamide

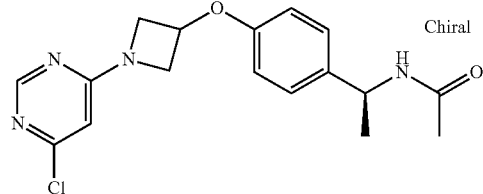

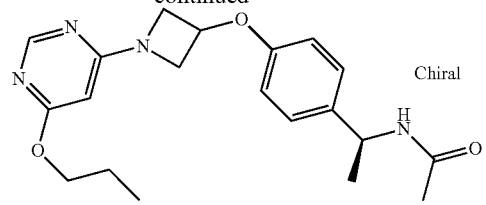

To 20.8 mg (0.35 mmol) 1-propanol in 1 mL THF is added 9.13 mg (0.38 mmol) NaH.

The mixture is stirred at r.t. for 10 min and afterwards charged with 60.0 mg (0.17 mmol) of the chloropyrimidine XXXIX.2. The resulting mixture is stirred at 80° C. over night. Then the mixture is filtered and directly purified by HPLC (MeOH/H$_2$O/NH$_3$).

$C_{20}H_{26}N_4O_3$ (M=370.5 g/mol)

ESI-MS: 371 [M+H]$^+$

R$_t$ (HPLC): 1.04 min (method K)

The following compounds are prepared analogously to example 11.1:

| Ex. | Starting material | Structure | Mass spec result | HPLC retention time (method) |
|---|---|---|---|---|
| 11.1 | XXXIX.2 | 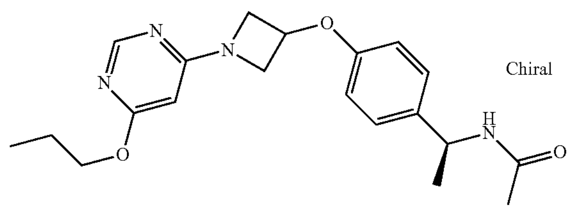 [SMILES: CCCOc1cc(N2CC(Oc3ccc([C@H](C)NC(C)=O)cc3)C2)ncn1] | 371 [M + H]$^+$ | 1.04 (K) |
| 11.2 | XXXIX.2 | 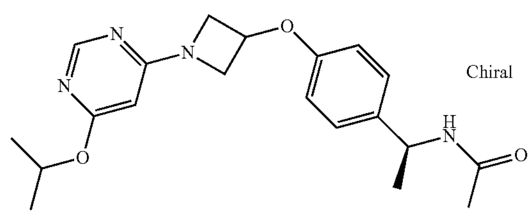 [SMILES: CC(=O)N[C@@H](C)c1ccc(OC2CN(c3cc(OC(C)C)ncn3)C2)cc1] | 371 [M + H]$^+$ | 1.02 (K) |
| 11.3 | XXXIX.2 | 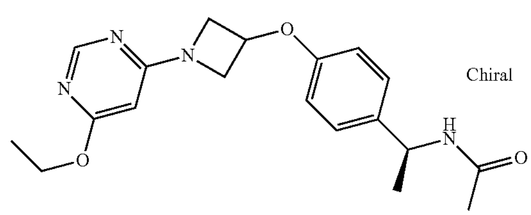 [SMILES: CCOc1cc(N2CC(Oc3ccc([C@H](C)NC(C)=O)cc3)C2)ncn1] | 357 [M + H]$^+$ | 0.95 (K) |
| 11.4 | XXXIX.2 | 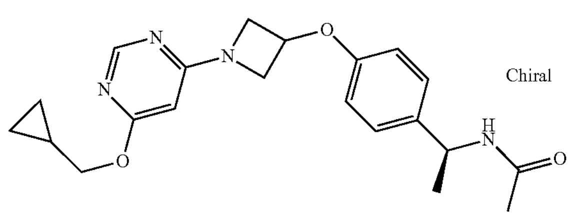 [SMILES: CC(=O)N[C@@H](C)c1ccc(OC2CN(c3cc(OCC4CC4)ncn3)C2)cc1] | 383 [M + H]$^+$ | 1.03 (K) |

The following compounds are prepared analogously to example 11.1:

| Ex. | Starting material | Structure | Mass spec result | HPLC retention time (method) |
|---|---|---|---|---|
| 11.5 | XXXIX.2 | 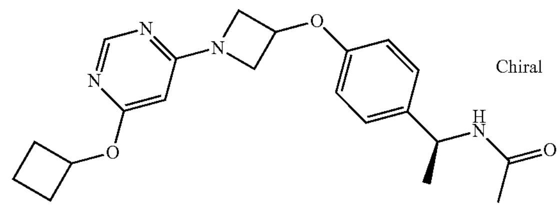 [SMILES: CC(=O)N[C@@H](C)c1ccc(OC2CN(c3cc(OC4CCC4)ncn3)C2)cc1] | 383 [M + H]+ | 1.04 (K) |
| 11.6 | XXXIX.1 | 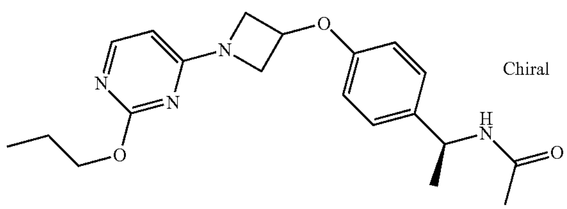 [SMILES: CCCOc1nccc(N2CC(Oc3ccc([C@H](C)NC(C)=O)cc3)C2)n1] | 371 [M + H]+ | 1.01 (K) |

Example 12

Example 12.1 (General Route)

(S)—N-(1-(4-(1-(64(Cyclopropylmethyl)(methyl)amino)pyrimidin-4-yl)azetidin-3-yloxy)phenyl)ethyl)acetamide

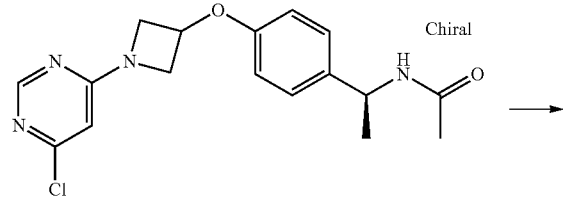

→

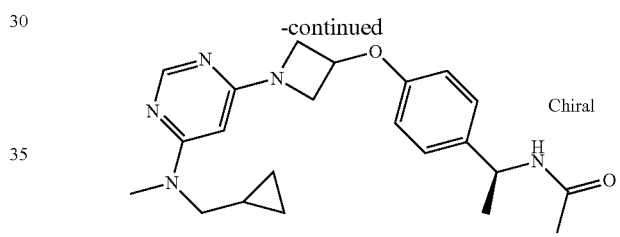

60.0 mg (0.17 mmol) of the chloropyrimidine XXXIX.2, 31.6 mg (0.26 mmol) 1-cyclopropyl-N-methylmethanamine and 150 µl (0.87 mmol) DIPEA are added to 1.5 mL NMP and stirred at 130° C. for 5 h. Then the mixture is filtered and directly purified by HPLC (MeOH/H$_2$O/NH$_3$).

$C_{22}H_{29}N_5O_2$ (M=395.5 g/mol)
ESI-MS: 396 [M+H]+
R$_t$ (HPLC): 1.04 min (method K)

The following compounds are prepared analogously to example 12.1:

| Ex. | Starting material | Structure | Mass spec result | HPLC retention time (method) |
|---|---|---|---|---|
| 12.1 | XXXIX.2 | 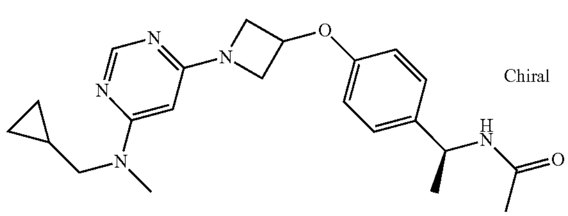 [SMILES: CC(=O)N[C@@H](C)c1ccc(OC2CN(c3cc(N(C)CC4CC4)ncn3)C2)cc1] | 396 [M + H]+ | 1.04 (K) |

| Ex. | Starting material | Structure | Mass spec result | HPLC retention time (method) |
|---|---|---|---|---|
| 12.2 | XXXIX.1 | 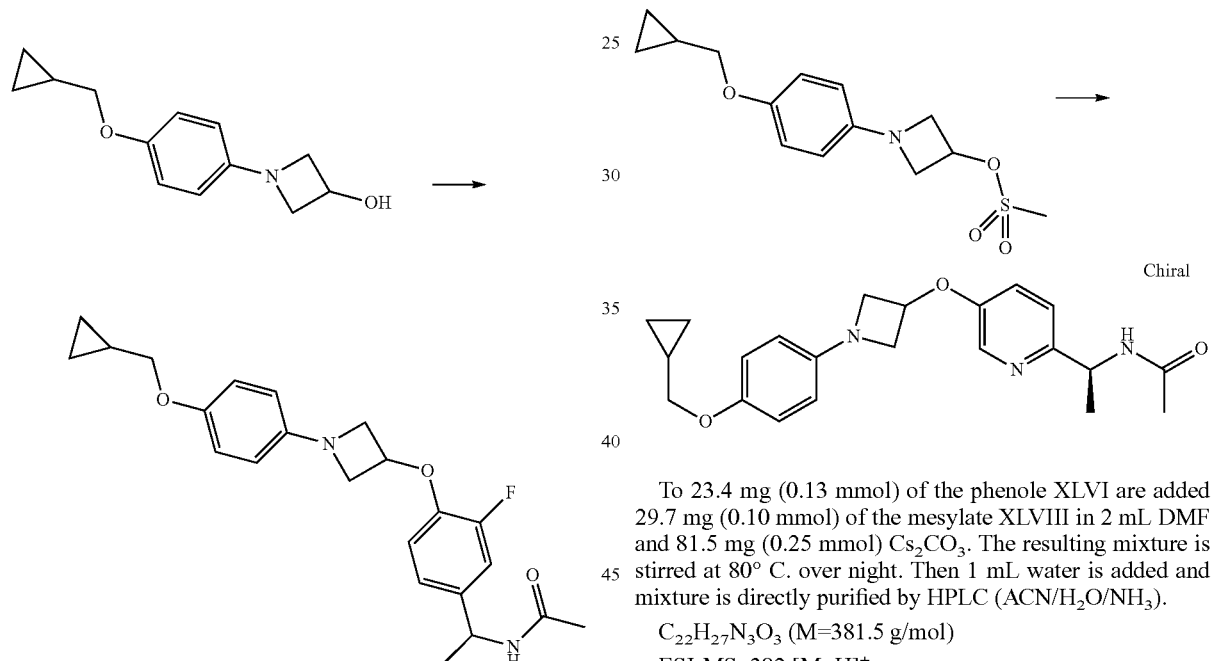 | 396 [M + H]+ | 1.13 (K) |

Example 13

N-(1-(4-(1-(4-(cyclopropylmethoxy)phenyl)azetidin-3-yloxy)-3-fluorophenyl) ethyl)-acetamide To 22.4 mg (0.11 mmol) of the phenole XLV in 2.5 ml THF are added 24.1 mg (0.11 mmol) of intermediate XLVII, 28.9 mg (0.11 mmol) triphenylphosphine and 25.3 mg (0.11 mmol) DBAD. The resulting mixture is stirred at 60° C. over night. To the mixture, 28.9 mg (0.11 mmol) triphenylphosphine and 25.3 mg (0.11 mmol) DBAD were added and the mixture is stirred for further 5 h at 60° C. The solvent is evaporated, the residue is dissolved in 1 ml DMF and the mixture is purified by HPLC (ACN/H$_2$O/NH$_3$).

$C_{23}H_{27}FN_2O_3$ (M=398.5 g/mol)

ESI-MS: 399 [m+H]+

R$_t$ (HPLC): 0.54 (method AC)

Example 14

N-(1-{5-[1-(4-Cyclopropylmethoxy-phenyl)-azetidin-3-yloxy]-pyridin-2-yl}-ethyl)-acetamide To 23.4 mg (0.13 mmol) of the phenole XLVI are added 29.7 mg (0.10 mmol) of the mesylate XLVIII in 2 mL DMF and 81.5 mg (0.25 mmol) Cs$_2$CO$_3$. The resulting mixture is stirred at 80° C. over night. Then 1 mL water is added and mixture is directly purified by HPLC (ACN/H$_2$O/NH$_3$).

$C_{22}H_{27}N_3O_3$ (M=381.5 g/mol)

ESI-MS: 382 [M+H]+

R$_t$ (HPLC): 0.72 (method AD)

Analytic Methods

1 HPLC

| Method A | | |
|---|---|---|
| time (min) | Vol % water (incl. 0.2% NH$_4$OH) | Vol % methanol (incl. 3% water) |
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters); 2.5 µm; 3.0 × 30 mm; column temperature: 40° C.; flow: 1.3 mL/min;

Method B

| time (min) | Vol % water (incl. 0.1% FA) | Vol % acetonitrile (incl. 0.1% FA) |
|---|---|---|
| 0.0 | 95 | 5 |
| 0.1 | 95 | 5 |
| 3.1 | 2 | 98 |
| 4.5 | 2 | 98 |
| 5.0 | 95 | 5 |

Analytical column: X-terra ™ MS C18 (Waters); 2.5 μm; 4.6 × 30 mm; column temperature: r.t.; flow: 1.0 mL/min; detection 210-420 nm.

Method C

| time (min) | Vol % water (incl. 0.1% FA) | Vol % methanol (incl. 0.1% FA) |
|---|---|---|
| 0.0 | 90 | 10 |
| 2.5 | 2 | 98 |
| 6.0 | 2 | 98 |

Analytical column: XBridge C18 (Waters); 3.5 μm; 2.1 × 50 mm; column temperature: 35° C.; flow: 0.8 mL/min; detection 220-320 nm.

Method D

| time (min) | Vol % water (incl. 0.2% FA) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: Zorbax StableBond C18 (Agilent); 1.8 μm; 3.0 × 30 mm; column temperature: 40° C.; flow: 1.3 mL/min;

Method E

| time (min) | Vol % water (incl. 0.1% TFA) | Vol % methanol |
|---|---|---|
| 0.0 | 80 | 20 |
| 1.7 | 0 | 100 |
| 2.5 | 0 | 100 |
| 2.6 | 80 | 20 |

Analytical column: Sunfire C18 (Waters); 3.5 μm; 4.6 × 50 mm; column temperature: 60° C.; flow: 2 mL/min;

Method F

| time (min) | Vol % water (incl. 0.2% NH$_4$OH) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: Gemini C18 (Phenomenex); 2.5 μm; 3.0 × 30 mm; column temperature: 40° C.; flow: 1.3 mL/min

Method G

| time (min) | Vol % water (incl. 0.2% NH$_4$OH) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters); 2.5 μm; 3.0 × 30 mm; column temperature: 60° C.; flow: 1.3 mL/min;

Method H

| time (min) | Vol % water (incl. 0.05% TFA) | Vol % ACN |
|---|---|---|
| 0.0 | 40 | 60 |
| 6 | 10 | 90 |
| 15 | 10 | 90 |
| 15.1 | 40 | 60 |

Analytical column: XBridge C18 (Waters) 3.5 μm; 4.6 × 50 mm; column temperature: r.t.;

Method I

| time (min) | Vol % water (incl. 0.01M NH4OAc) | Vol % ACN |
|---|---|---|
| 0.0 | 50 | 50 |
| 6 | 10 | 90 |
| 15 | 10 | 90 |
| 15.1 | 40 | 60 |

Analytical column: Eclipse-XDB-C18 (Agilent), 5.0 μm; 4.6 × 150 mm; column temperature: r.t.; flow: 1.0 ml/min.

Method J

| time (min) | Vol % water (incl. 0.01M NH4OAc) | Vol % ACN |
|---|---|---|
| 0.0 | 70 | 30 |
| 8 | 10 | 90 |
| 15 | 10 | 90 |
| 15.1 | 70 | 30 |

Analytical column: XBridge C8 (Waters) 5.0 μm; 4.6 × 150 mm; column temperature: r.t.; flow: 1 ml/min.

Method K

| time (min) | Vol % water (incl. 0.2% NH$_4$OH) | Vol % MeOH |
|---|---|---|
| 0.0 | 95 | 5 |
| 0.05 | 95 | 5 |
| 1.40 | 0 | 100 |
| 1.80 | 0 | 100 |

Analytical column: XBridge C18 (Waters) 2.5 μm; 3.0 × 30 mm; column temperature: 60° C.; flow: 2.2 ml/min.

Method L

| time (min) | Vol % water (incl. 0.2% NH$_4$OH) | Vol % MeOH |
|---|---|---|
| 0.0 | 95 | 5 |
| 1.0 | 10 | 90 |
| 2.2 | 10 | 90 |
| 2.3 | 0 | 100 |
| 2.5 | 0 | 100 |

Analytical column: XBridge C18 (Waters) 2.5 µm; 3.0 × 30 mm; column temperature: 40° C.; flow: 1.3 ml/min.

Method M

| time (min) | Vol % water (incl. 0.2% TFA) | Vol % MeOH |
|---|---|---|
| 0.00 | 95 | 5 |
| 0.05 | 95 | 5 |
| 1.40 | 0 | 100 |
| 1.80 | 0 | 100 |

Analytical column: Sunfire C18 (Waters) 2.5 µm 3.0 × 30 mm; column temperature: 60° C.; flow: 2.2 ml/min.

Method N

| time (min) | Vol % water (incl. 0.1% NH$_4$OH) | Vol % MeOH | Flow [ml/min] |
|---|---|---|---|
| 0.0 | 95 | 5 | 2.2 |
| 0.30 | 95 | 5 | 2.2 |
| 1.50 | 0 | 100 | 2.2 |
| 1.55 | 0 | 100 | 2.9 |
| 1.70 | 0 | 100 | 2.9 |

Analytical column: XBridge C18 (Waters) 2.5 µm; 3.0 × 30 mm; column temperature: 60° C.

Method O

| time (min) | Vol % water (incl. 0.1% NH$_4$OH) | Vol % MeOH |
|---|---|---|
| 0.0 | 95 | 5 |
| 0.15 | 95 | 5 |
| 1.70 | 0 | 100 |
| 2.10 | 0 | 100 |

Analytical column: XBridge C18 (Agilent) 3.5 µm; 4.6 × 30 mm; column temperature: 60° C.; flow: 4 ml/min

Method P

| time (min) | Vol % water (incl. 0.15% TFA) | Vol % MeOH |
|---|---|---|
| 0.00 | 95 | 5 |
| 0.25 | 95 | 5 |
| 1.90 | 0 | 100 |
| 2.05 | 0 | 100 |

Analytical column: Microsorb C18 (Waters) 5 µm; 4.6 × 20 mm; column temperature: r.t.; flow: 5.2 ml/min.

Method Q

| time (min) | Vol % water (incl. 0.05% TFA) | Vol % ACN |
|---|---|---|
| 0.0 | 70 | 30 |
| 8 | 10 | 90 |
| 15 | 10 | 90 |
| 15.1 | 70 | 30 |

Analytical column: XBridge C18 (Waters) 3.5 µm; 4.6 × 150 mm; column temperature: r.t.; flow: 1 ml/min.

Method R

| time (min) | Vol % water (incl. 0.1% FA) | Vol % ACN |
|---|---|---|
| 0.0 | 40 | 60 |
| 4 | 10 | 90 |
| 15 | 10 | 90 |
| 15.1 | 10 | 60 |

Analytical column: Symmetry C18 (Waters) 3.5 µm; 4.6 × 75 mm; column temperature: r.t.; flow: 1 ml/min.

Method S

| time (min) | Vol % water (incl. 0.1% TFA) | Vol % ACN (incl. 0.1% TFA) |
|---|---|---|
| 0.0. | 95 | 5 |
| 2.0. | 0 | 100 |
| 2.49 | 0 | 100 |
| 2.50 | 95 | 5 |

Analytical column: Sunfire C18 (Waters) 3.5 µm; 4.6 × 50 mm; column temperature: 40° C.; flow: 1.5 ml/min.

Method T

| time (min) | Vol % water (incl. 0.1% TFA) | Vol % MeOH | Flow [ml/min] |
|---|---|---|---|
| 0.0 | 95 | 5 | 1.5 |
| 0.7 | 1 | 99 | 1.5 |
| 0.8 | 1 | 99 | 1.5 |
| 0.81 | 95 | 5 | 1.5 |

Analytical column: Ascentis Express C18 (Supelco) 2.7 µm; 2.1 × 50 mm; column temperature: 60° C.;

Method U

| time (min) | Vol % water (incl. 0.1% FA) | Vol % MeOH | Flow [ml/min] |
|---|---|---|---|
| 0.0 | 95 | 5 | 2.2 |
| 0.05 | 95 | 5 | 2.2 |
| 1.40 | 0 | 100 | 2.2 |
| 1.80 | 0 | 100 | 2.2 |

Analytical column: Sunfire C18 (Waters) 2.5 µm; 3 × 30 mm; column temperature: 60° C.;

| Method V | | | |
|---|---|---|---|
| time (min) | Vol % water (incl. 0.1% TFA) | Vol % MeOH (incl. 0.1% TFA) | Flow [ml/min] |
| 0.0 | 95 | 5 | 4.0 |
| 0.15 | 95 | 5 | 4.0 |
| 1.70 | 0 | 100 | 4.0 |
| 2.25 | 0 | 100 | 4.0 |

Analytical column: Sunfire C18 (Waters) 3.5 µm; 4.6 × 30 mm; column temperature: 60° C.

| Method W | | | |
|---|---|---|---|
| time (min) | Vol % water (incl. 0.1% FA) | Vol % MeOH | Flow [ml/min] |
| 0.0 | 40 | 60 | 1.0 |
| 6 | 10 | 90 | 1.0 |
| 16 | 10 | 90 | 1.0 |
| 18 | 40 | 60 | 1.0 |
| 20 | 40 | 60 | 1.0 |

Analytical column: Kromasil C18 100 (Akzo Nobel) 5.0 µm; 4.6 × 250 mm; column temperature: r.t.;

| Method X | | | |
|---|---|---|---|
| time (min) | Vol % water (incl. 0.1% TFA) | Vol % MeOH | Flow [ml/min] |
| 0.0 | 95 | 5 | 2.2 |
| 0.30 | 95 | 5 | 2.2 |
| 1.50 | 0 | 100 | 2.2 |
| 1.55 | 0 | 100 | 2.9 |
| 1.65 | 0 | 100 | 2.9 |

Analytical column: Sunfire C18 (Waters) 2.5 µm; 3 × 30 mm; column temperature: 60° C.

| Method Y | | |
|---|---|---|
| time (min) | Vol % water (incl. 0.1% FA) | Vol % ACN (incl. 0.1% FA) |
| 0.0 | 95 | 5 |
| 3.50 | 2 | 98 |
| 6.00 | 2 | 98 |

Analytical column: X-Bridge C18 (Waters) 3.5 µm; 2.1 × 50 mm; column temperature: 35° C.; flow: 0.8 ml/min.

| Method Z | | |
|---|---|---|
| time (min) | Vol % water (incl. 0.1% TFA) | Vol % MeOH |
| 0.0 | 95 | 5 |
| 0.05 | 95 | 5 |
| 1.40 | 0 | 100 |
| 1.80 | 0 | 100 |

Analytical column: StableBond C18 (Waters) 1.8 µm; 3.0 × 30 mm; column temperature: 60° C.; flow: 2.2 ml/min.

| Method AA | | | |
|---|---|---|---|
| time (min) | Vol % water (incl. 0.1% TFA) | Vol % ACN | Flow [mL/min] |
| 0.00 | 97 | 3 | 2.2 |
| 0.20 | 97 | 3 | 2.2 |
| 1.20 | 0 | 100 | 2.2 |
| 1.25 | 0 | 100 | 3 |
| 1.40 | 0 | 100 | 3 |

Analytical column: Sunfire C18 (Waters) 2.5 µm; 3.0 × 30 mm; column temperature: 60° C.

| Method AB | | | |
|---|---|---|---|
| time (min) | Vol % water (incl. 0.1% NH$_4$OH) | Vol % MeOH | Flow [ml/min] |
| 0.0 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: XBridge C18 (Waters) 2.5 µm; 3.0 × 30 mm; column temperature: 60° C.

| Method AC | | |
|---|---|---|
| time (min) | Vol % water (incl. 0.1% TFA) | Vol % ACN (incl. 0.08% TFA) |
| 0.0 | 95.0 | 5.0 |
| 0.75 | 0.0 | 100.0 |
| 0.85 | 0.0 | 100.0 |

Analytical column: Sunfire C18 (Waters) 2.5 µm; 2.1 × 50 mm; column temperature: 60° C.; flow: 1.5 ml/min.

| Method AD | | | |
|---|---|---|---|
| time (min) | Vol % water (incl. 0.1% NH$_4$OH) | Vol % ACN | Flow [ml/min] |
| 0.0 | 98 | 3 | 2.0 |
| 1.20 | 0 | 100 | 2.0 |
| 1.40 | 0 | 100 | 2.0 |

Analytical column: XBridge C18 (Waters) 2.5 µm; 3.0 × 30 mm; column temperature: 60° C.

2 GC

Method AAA

Analytical column: SLB-5MS15 m, ID 100 df 0.10

Average velocity 45 cm/s, carrier gas:He, split ratio: 300:1, injector temp: 250° C., injection volume: 14.

Initial temp: 60° C., initial time: 1.0 min, solvent delay: 0.6 min, rate: 50° C./min, final temp: 250° C., final time: 1.0 min.

The invention claimed is:
1. A compound of the formula I

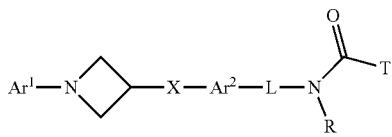

wherein
Ar$^1$ is selected from the group consisting of:
6- to 10-membered aryl and 5- to 10-membered heteroaryl, which may each be substituted with one or more substituents R$^1$,
wherein two substituents R$^1$ linked to adjacent C-atoms of Ar$^1$ together may form a C$_{3-5}$-alkylene bridge in which 1, 2 or 3 CH$_2$-groups may be replaced independently of each other by O, C(=O), S, S(=O), S(=O)$_2$, NH or N(C$_{1-4}$-alkyl)-, wherein the alkylene bridge may optionally be substituted by one or two F atoms or one or two C$_{1-3}$-alkyl groups; and
R$^1$ is selected from the group consisting of:
H, F, Cl, Br, I, CN, OH, —NO$_2$, C$_{1-6}$-alkyl, C$_{2-6}$-alkenyl, C$_{2-6}$-alkynyl, C$_{3-10}$-carbocyclyl, C$_{3-10}$-carbocyclyl-C$_{1-3}$-alkyl, C$_{1-6}$-alkyl-O—, C$_{3-6}$-alkenyl-O—, C$_{3-6}$-alkynyl-O—, C$_{3-10}$-carbocyclyl-O—, C$_{3-10}$-carbocyclyl-C$_{1-3}$-alkyl-O—, C$_{1-6}$-alkyl-S—, C$_{1-6}$-alkyl-S(=O)—, C$_{1-6}$-alkyl-S(=O)$_2$—, C$_{3-10}$-carbocyclyl-S—, C$_{3-10}$-carbocyclyl-C$_{1-3}$-alkyl-S—, C$_{1-4}$-alkyl-C(=O)—, C$_{3-10}$-carbocyclyl-C(=O)—, R$^{N1}$R$^{N2}$N—, R$^{N1}$R$^{N2}$N—C$_{2-3}$-alkyl-O—, R$^{N1}$R$^{N2}$N—C(=O)—, R$^{N1}$R$^{N2}$N—S(=O)$_2$—, C$_{1-6}$-alkyl-C(=O)—NR$^{N1}$—, C$_{1-6}$-alkyl-S(=O)$_2$—NR$^{N1}$—, C$_{1-6}$-alkyl-C(=O)—NR$^{N1}$—C$_{1-3}$-alkyl-, HO—C(=O)—, C$_{1-6}$-alkyl-O—C(=O)—, heterocyclyl, heterocyclyl-O—, heterocyclyl-C$_{1-3}$-alkyl, heterocyclyl-C$_{1-3}$-alkyl-O—, heterocyclyl-C(=O)—, aryl, aryl-C$_{1-3}$-alkyl, aryl-O—, aryl-C$_{1-3}$-alkyl-O—, heteroaryl, heteroaryl-C$_{1-3}$-alkyl, heteroaryl-O— and heteroaryl-C$_{1-3}$-alkyl-O—,
wherein in each carbocyclyl and heterocyclyl a CH$_2$-group may optionally be replaced by —C(=O)— or —C(=CR$^{N2}$$_2$)—, and
wherein each carbocyclyl and heterocyclyl may be optionally substituted with one or more C$_{1-4}$-alkyl, which may be optionally substituted with one or more substituents R$^C$, and
wherein each alkyl, carbocyclyl and heterocyclyl may be optionally substituted with one or more substituents R$^C$, and
wherein each heterocyclyl may be optionally substituted with aryl or heteroaryl, and
wherein each aryl and heteroaryl group may be optionally substituted with one or more substituents R$^2$,
R$^C$ is selected from the group consisting of:
F, Cl, Br, CN, OH, C$_{1-4}$-alkyl-O—, C$_{3-7}$-cycloalkyl-O—, C$_{3-7}$-cycloalkyl-C$_{1-3}$-alkyl-O—, H$_2$N—, (C$_{1-4}$-alkyl)NH—, (C$_{1-4}$-alkyl)$_2$N—, C$_{1-4}$-alkyl-C(=O)—, C$_{1-4}$-alkyl-S(=O)$_2$—, HO—C(=O)— and C$_{1-4}$-alkyl-O—C(=O)—, wherein each alkyl or cycloalkyl may be optionally substituted with one or more substituents selected from F and OH, and
R$^{N1}$ is selected from the group consisting of:
H, C$_{1-6}$-alkyl, C$_{3-10}$-carbocyclyl, C$_{3-10}$-carbocyclyl-C$_{1-3}$-alkyl, C$_{3-6}$-alkenyl, C$_{3-6}$-alkynyl, heterocyclyl, heterocyclyl-C$_{1-3}$-alkyl, aryl, aryl-C$_{1-3}$-alkyl, heteroaryl and heteroaryl-C$_{1-3}$-alkyl,
wherein each carbocyclyl and heterocyclyl may be optionally substituted with one or more C$_{1-4}$-alkyl, and
wherein in each carbocyclyl and heterocyclyl a CH$_2$-group may optionally be replaced by —C(=O)—, and
wherein each alkyl, carbocyclyl and heterocyclyl may be optionally substituted with one or more substituents R$^C$, and
wherein each aryl and heteroaryl group may be optionally substituted with one or more substituents R$^2$,
R$^{N2}$ is selected from the group consisting of: H and C$_{1-6}$-alkyl, and
Ar$^2$ is selected from the group consisting of:
phenylene and a 5- or 6-membered monocyclic heteroaryl group containing 1, 2 or 3 heteroatoms selected from N, O, or S, wherein Ar$^2$ may be optionally substituted with one or more substituents R$^2$, and
R$^2$ is selected from the group consisting of:
F, Cl, Br, CN, OH, C$_{1-4}$-alkyl-, C$_{1-4}$-alkyl-O—, C$_{1-4}$-alkyl-S—, C$_{1-4}$-alkyl-S(=O)$_2$—, H$_2$N—, (C$_{1-4}$-alkyl)NH—, (C$_{1-4}$-alkyl)$_2$N—, C$_{1-4}$-alkyl-C(=O)—NH— and heterocyclyl,
wherein each alkyl may be optionally substituted with one or more F-atoms and/or with a substituent selected from OH, C$_{1-3}$-alkyl-O— and CN; and
wherein two substituents R$^2$ attached to an aryl or heteroaryl group may be linked to each other and form a C$_{2-5}$-alkylene bridging group in which 1 or 2-CH$_2$-groups may be replaced by a group independently of each other selected from O, S, NH and N(C$_{1-4}$-alkyl)-, wherein the C$_{2-5}$-alkylene bridging group is optionally be substituted by 1 or 2 C$_{1-3}$-alkyl groups;
L is selected from the group consisting of:
a C$_{1-4}$-alkylene group that is optionally substituted by one or two CH$_3$;
X is selected from the group consisting of: O and S;
R is selected from the group consisting of: H and C$_{1-3}$-alkyl; and
T is selected from the group consisting of:
C$_{1-6}$-alkyl, C$_{2-6}$-alkenyl, C$_{2-6}$-alkynyl, C$_{3-10}$-carbocyclyl, C$_{3-10}$-carbocyclyl-C$_{1-3}$-alkyl, C$_{1-6}$-alkyl-O—, C$_{3-10}$-carbocyclyl-O—, C$_{3-10}$-carbocyclyl-C$_{1-3}$-alkyl-O—, C$_{1-6}$-alkyl-S—, C$_{3-10}$-carbocyclyl-S—, C$_{3-10}$-carbocyclyl-C$_{1-3}$-alkyl-S—, C$_{1-4}$-alkyl-C(=O)—, C$_{1-4}$-alkyl-S(=O)$_2$—, R$^{N1}$R$^{N2}$—N—, R$^{N1}$R$^{N2}$—N—C$_{1-3}$-alkyl-, R$^{N1}$R$^{N2}$—N—CO—, C$_{1-4}$-alkyl-C(=O)—R$^{N2}$N—C$_{1-3}$-alkyl, heterocyclyl, aryl and heteroaryl,
wherein in each carbocyclyl and heterocyclyl a CH$_2$-group may optionally be replaced by —C(=O)—, and
wherein each carbocyclyl and heterocyclyl may be optionally substituted with one or more C$_{1-4}$-alkyl, which may be optionally substituted with one or more substituents R$^C$, and
wherein each alkyl, carbocyclyl and heterocyclyl may be optionally substituted with one or more substituents R$^C$, and
wherein each alkyl may optionally be substituted with a heteroaryl group; and
wherein each aryl and heteroaryl group may be optionally substituted with one or more substituents R$^2$;
or a tautomer or pharmaceutically acceptable salt thereof.

2. A compound according to claim 1 wherein
X is O, and
R is H or CH$_3$.

3. A compound according to claim 1 wherein Ar¹ is selected from a group consisting of:
phenyl, pyridinyl, pyrimidinyl, benzoxazolyl, benzoisoxalyl, benzthiazolyl, quinolinyl, isoquinolinyl, quinoxalinyl and oxazolopyrimidinyl,
  wherein the above-mentioned phenyl, pyridinyl and pyrimidinyl are each substituted with one to three groups independently selected from R¹, and/or
  wherein two adjacent carbon atoms of a phenyl group may be linked to each other via a —O—CH₂—O—, —O—CF₂—O—, —O—CH₂—CH₂—O—, —O—CH₂—CH₂—CH₂—CH₂—, —O—CH₂—CH₂—CH₂—C(CH₃)₂—, —O—CH₂—CH₂—CH₂—O— or —O—CH₂—C(CH₃)₂—CH₂—O— bridge, and
  wherein the above-mentioned benzoxazolyl, benzoisoxalyl, benzthiazolyl, quinolinyl, isoquinolinyl, quinoxalinyl and oxazolopyrimidinyl groups are each optionally substituted with Cl, CH₃ or phenyl.

4. A compound according to claim 1 wherein R¹ is selected from the group consisting of:
H, F, Cl, Br, CN, OH, C₁₋₄-alkyl, C₂₋₄-alkenyl, C₃₋₇-cycloalkyl, C₃₋₇-cycloalkyl-CH₂—, C₁₋₄-alkyl-O—, C₃₋₇-cycloalkyl-O—, C₃₋₇-cycloalkyl-C₁₋₃-alkyl-O—, C₁₋₄-alkyl-S(=O)₂, R^{N1}R^{N2}N—, HO—C(=O)—, C₁₋₄-alkyl-O—C(=O)—, phenyl, phenyl-O—, phenyl-CH₂—O—, and pyridinyl
  wherein each alkyl and cycloalkyl may be optionally substituted with one to three substituents independently selected from the group consisting of F and CN, and
  wherein each phenyl and pyridinyl group may be optionally substituted with one F or —OCH₃.

5. A compound according to claim 1 wherein Ar² is selected from the group consisting of:
phenylene and pyridylene, wherein Ar² may be optionally substituted with one to three substituents R²,
  wherein R² is F, Cl, C₁₋₂-alkyl-, C₁₋₂-alkyl-O—, C₁₋₃-alkyl-C(=O)—NH or HO—CH₂—C(=O)—NH—.

6. A compound according to claim 1 wherein L is a linear C₁₋₂-alkylene group that is optionally substituted with one CH₃.

7. A compound according to claim 1 wherein T is selected from the group consisting of:
C₁₋₄-alkyl, C₂₋₄-alkenyl, C₃₋₆-cycloalkyl, C₃₋₇-cycloalkenyl, C₃₋₆-cycloalkyl-C₁₋₃-alkyl-, heteroaryl-C₁₋₃-alkyl-, C₁₋₃-alkyl-O—, R^{T1}R^{T2}—N—, C₁₋₃-alkyl-C(=O)—R^{T2}N—C₁₋₃-alkyl-, heterocyclyl, phenyl and heteroaryl,
wherein in each heterocyclyl, a CH₂-group may optionally be replaced by —C(=O)—; and
wherein each cycloalkyl and heterocyclyl may be optionally substituted with one or more C₁₋₃-alkyl, which may be optionally substituted with one or more substituents R^C; and
wherein each alkyl, cycloalkyl and heterocyclyl may be optionally substituted with one or more F; and
wherein heterocyclyl is selected from the group consisting of

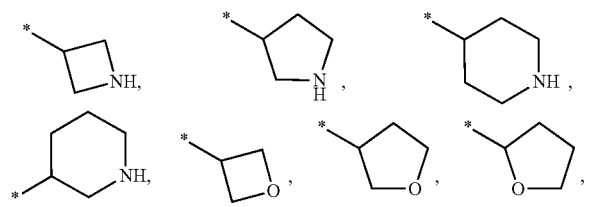

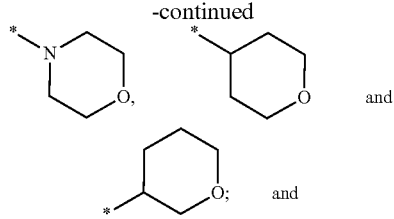

wherein heteroaryl is selected from the group consisting of pyridyl, pyrimidinyl, pyridazinyl, pyrazinyl, furanyl, thienyl, pyrrolyl, imidazolyl, pyrazolyl, triazolyl, oxazolyl, isoxazolyl, thiazolyl and isothiazolyl; and
wherein each phenyl and heteroaryl group may be optionally substituted with one or more substitutents selected from the group consisting of CH₃, CH₃—C(=O)—NH— and HO—CH₂—C(=O)—NH—; and
wherein R^C is selected from the group consisting of F, Cl, CN, OH and C₁₋₃-alkyl-; and
wherein R^{T1} is selected from the group consisting of H, methyl and ethyl; and
wherein R^{T2} is H or methyl.

8. A compound according to claim 1, wherein
Ar¹ is selected from the group consisting of phenyl, pyridinyl and pyrimidinyl,
  wherein the above-mentioned phenyl and pyridinyl groups are each substituted with one to three groups independently selected from R¹, and
  wherein the above-mentioned pyrimidinyl groups is substituted with one or two R¹, and
  wherein two adjacent carbon atoms of a phenyl group may be linked to each other via a —O—CH₂—CH₂—O—, —O—CH₂—CH₂—CH₂—C(CH₃)₂—, —O—CH₂—CH₂—CH₂—O—, or —O—CH₂—C(CH₃)₂—CH₂—O— bridge;
R¹ is selected from the group consisting of F, Cl, Br, CN, OF₃, C₁₋₄ alkyl, —O—C₁₋₄ alkyl, cyclopropyl, —O—C₃₋₅ cycloalkyl, —O—CH₂— cyclopropyl, and

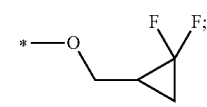

Ar² is phenylene;
L is a linear C₁₋₂-alkylene group that is optionally substituted with one CH₃,
X is O;
R is H; and
T is selected from the group consisting of: C₁₋₄-alkyl, C₂₋₄-alkenyl, C₃₋₅-cycloalkyl, C₅₋₆-cycloalkenyl, cyclopropyl-CH₂—, CH₃O—, R^{T1}R^{T2}—N—, CH₃—C(=O)—NH—C₁₋₃-alkyl, heterocyclyl, phenyl and heteroaryl,
  wherein R^{T1} is H, CH₃ or CH₂CH₃; and
  R^{T2} is H or CH₃; and
  wherein each alkyl, cycloalkyl and heterocyclyl may be optionally substituted with one F, CN, CH₃, CF₃, cyclopropyl, —N(CH₃)₂, pyridinyl, OH or —OCH₃; and wherein heterocyclyl is selected from the group consisting of:

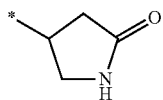 and 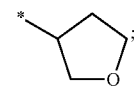 ; and wherein heteroaryl is selected from the group consisting of pyridyl, pyrimidinyl, pyridazinyl, furanyl, pyrazolyl, oxazolyl, isoxazolyl, thiazolyl and isothiazolyl; and
wherein each phenyl and heteroaryl group may be optionally substituted with one or two substituents independently selected from the group consisting of CH$_3$, —NH—CO—CH$_3$, and —NH—CO—CH$_2$—OH.

9. A compound according to claim 1, which is:

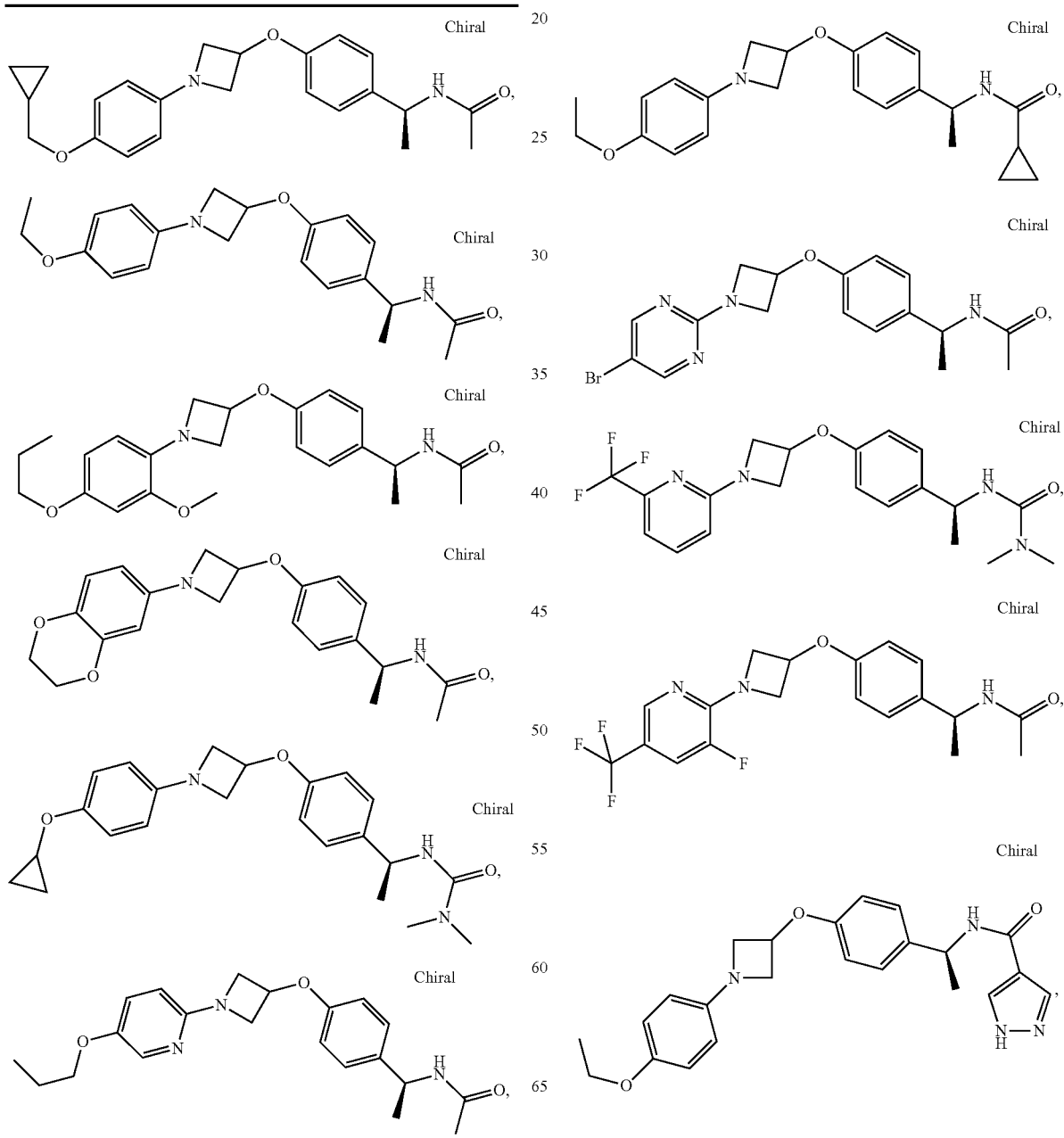
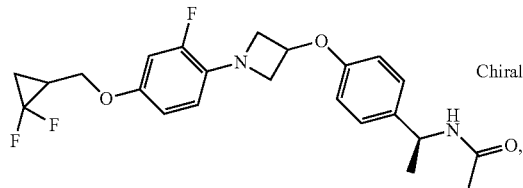 [SMILES: CC(=O)N[C@@H](C)c1ccc(OC2CN(c3ccc(OCC4CC4(F)F)cc3F)C2)cc1]

175
-continued

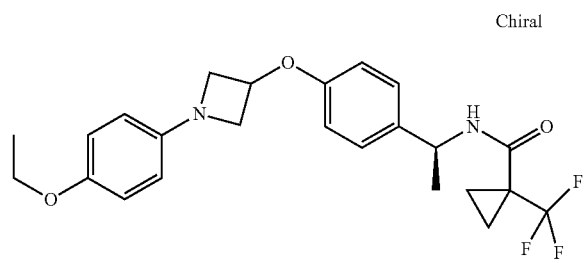 [SMILES: CCOc1ccc(N2CC(Oc3ccc([C@H](C)NC(=O)C4(C(F)(F)F)CC4)cc3)C2)cc1]

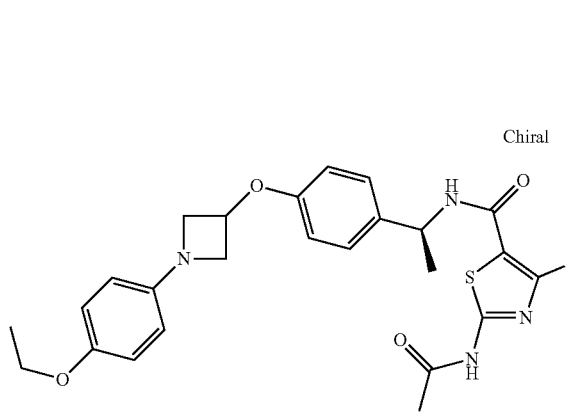

176
-continued

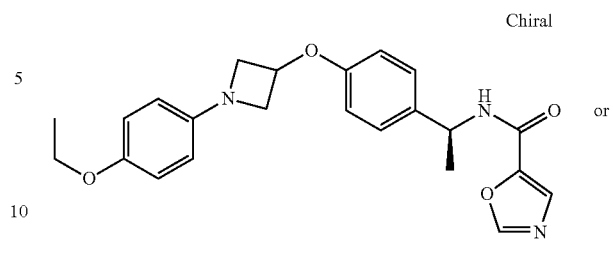

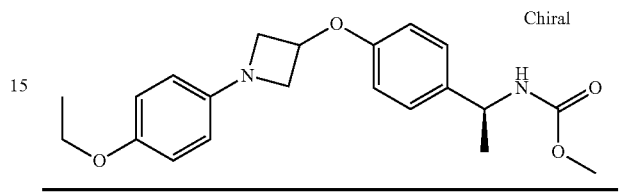

or a pharmaceutically acceptable salt thereof.

10. A pharmaceutical composition comprising a compound according to claim 1 and a pharmaceutically acceptable carrier or diluent.

11. A method for treating obesity, diabetes or dyslipidemia in a patient suffering from one of said conditions which method comprises administering to said patient a therapeutically effective amount of a compound according to claim 1.

* * * * *